United States Patent
Mujica-Fernaud et al.

(10) Patent No.: US 10,727,413 B2
(45) Date of Patent: Jul. 28, 2020

(54) MATERIALS FOR ELECTRONIC DEVICES

(71) Applicant: Merck Patent GmbH, Darmstadt (DE)

(72) Inventors: Teresa Mujica-Fernaud, Darmstadt (DE); Elvira Montenegro, Weinheim (DE); Jochen Pfister, Alsbach-Haehnlein (DE)

(73) Assignee: Merck Patent GmbH, Darmstadt (DE)

( * ) Notice: Subject to any disclaimer, the term of this patent is extended or adjusted under 35 U.S.C. 154(b) by 270 days.

(21) Appl. No.: 15/123,765

(22) PCT Filed: Feb. 9, 2015

(86) PCT No.: PCT/EP2015/000271
§ 371 (c)(1),
(2) Date: Sep. 6, 2016

(87) PCT Pub. No.: WO2015/131976
PCT Pub. Date: Sep. 11, 2015

(65) Prior Publication Data
US 2017/0018710 A1 Jan. 19, 2017

(30) Foreign Application Priority Data
Mar. 7, 2014 (EP) .................................. 14000814

(51) Int. Cl.
| | |
|---|---|
| *H01L 51/00* | (2006.01) |
| *C07C 211/61* | (2006.01) |
| *C07C 209/60* | (2006.01) |
| *C07C 209/68* | (2006.01) |
| *C07C 211/54* | (2006.01) |
| *C09K 11/06* | (2006.01) |
| *H01L 51/50* | (2006.01) |
| *C07D 209/86* | (2006.01) |
| *C07D 307/91* | (2006.01) |
| *C07D 333/76* | (2006.01) |

(52) U.S. Cl.
CPC .......... *H01L 51/006* (2013.01); *C07C 209/60* (2013.01); *C07C 209/68* (2013.01); *C07C 211/54* (2013.01); *C07C 211/61* (2013.01); *C07D 209/86* (2013.01); *C07D 307/91* (2013.01); *C07D 333/76* (2013.01); *H01L 51/0058* (2013.01); *H01L 51/0061* (2013.01); *H01L 51/0073* (2013.01); *H01L 51/0074* (2013.01); *C07C 2603/18* (2017.05); *C07C 2603/26* (2017.05); *C07C 2603/97* (2017.05); *C09K 11/06* (2013.01); *C09K 2211/1022* (2013.01); *C09K 2211/1029* (2013.01); *C09K 2211/1033* (2013.01); *C09K 2211/1037* (2013.01); *C09K 2211/1044* (2013.01); *C09K 2211/1092* (2013.01); *C09K 2211/185* (2013.01); *H01L 51/0052* (2013.01); *H01L 51/0056* (2013.01); *H01L 51/0072* (2013.01); *H01L 51/0085* (2013.01); *H01L 51/0087* (2013.01); *H01L 51/5056* (2013.01); *H01L 51/5088* (2013.01); *H01L 51/5096* (2013.01)

(58) Field of Classification Search
CPC ... C07C 209/60; C07C 209/68; C07C 211/54; C07C 211/61; C07C 2603/18; C07C 2603/26; C07C 2603/97; C07D 209/86; C07D 307/91; C07D 333/76; C09K 11/06; C09K 2211/1022; C09K 2211/1029; C09K 2211/1033; C09K 2211/1037; C09K 2211/1044; C09K 2211/1092; C09K 2211/185; H01L 51/0052; H01L 51/0056; H01L 51/0058; H01L 51/006; H01L 51/0061; H01L 51/0072; H01L 51/0073; H01L 51/0074; H01L 51/0085; H01L 51/0087; H01L 51/5056; H01L 51/5088; H01L 51/5096; Y02E 10/549
See application file for complete search history.

(56) References Cited

U.S. PATENT DOCUMENTS

| | | | |
|---|---|---|---|
| 7,947,382 B2 | 5/2011 | Büsing et al. | |
| 8,344,365 B2 | 1/2013 | Kim et al. | |
| 8,968,887 B2 * | 3/2015 | Ma .......................... | C09K 11/06 428/690 |
| 9,972,787 B2 | 5/2018 | Miyake et al. | |
| 2003/0091862 A1 * | 5/2003 | Tokito ..................... | C08G 61/02 428/690 |
| 2003/0118866 A1 * | 6/2003 | Oh ......................... | H01L 51/0058 428/690 |
| 2003/0219625 A1 * | 11/2003 | Wolk ...................... | C09K 11/06 428/690 |
| 2005/0258400 A1 | 11/2005 | Wingen et al. | |
| 2008/0124572 A1 | 5/2008 | Mizuki et al. | |

(Continued)

FOREIGN PATENT DOCUMENTS

| | | |
|---|---|---|
| CN | 101987822 A | 3/2011 |
| CN | 101993409 A | 3/2011 |

(Continued)

OTHER PUBLICATIONS

Machine translation of JP 2004-087245 A (publication date: Mar. 2004). (Year: 2004).*

(Continued)

*Primary Examiner* — Dawn L Garrett

(74) *Attorney, Agent, or Firm* — Faegre Drinker Biddle & Reath LLP

(57) ABSTRACT

The invention relates to phenanthrene compounds comprising one or more arylamino groups. Said compounds can be used in electronic devices, in particular OLED's.

13 Claims, No Drawings

(56) References Cited

U.S. PATENT DOCUMENTS

| | | |
|---|---|---|
| 2009/0230846 A1* | 9/2009 | Yabe .................. C07C 211/54 |
| | | 313/504 |
| 2010/0109555 A1 | 5/2010 | Ichimura et al. |
| 2012/0068121 A1 | 3/2012 | Sparrowe et al. |
| 2012/0199820 A1 | 8/2012 | Ito et al. |
| 2014/0138627 A1* | 5/2014 | Kwong ............... H01L 51/5004 |
| | | 257/40 |
| 2015/0137094 A1 | 5/2015 | Itoi et al. |
| 2015/0155491 A1 | 6/2015 | Mujica-Fernaud et al. |
| 2016/0072078 A1 | 3/2016 | Lee et al. |

FOREIGN PATENT DOCUMENTS

| | | | |
|---|---|---|---|
| CN | 103553936 A | | 2/2014 |
| DE | 10109463 A1 | | 10/2002 |
| EP | 866110 A1 | * | 9/1998 |
| EP | 0866110 A1 | | 9/1998 |
| EP | 1191821 A1 | | 3/2002 |
| JP | 2000012229 A | | 1/2000 |
| JP | 2004-087245 A | * | 3/2004 |
| JP | 2004-253298 | * | 9/2004 |
| JP | 2004253298 A | | 9/2004 |
| JP | 2005325113 A | | 11/2005 |
| JP | 2007-123713 A | * | 5/2007 |
| JP | 2007123713 A | | 5/2007 |
| JP | 2012528210 A | | 11/2012 |
| JP | 2015103583 A | | 6/2015 |
| JP | 2016051901 A | | 4/2016 |
| JP | 2016066723 A | | 4/2016 |
| KR | 20110011562 A | | 2/2011 |
| KR | 10-1347519 B1 | | 1/2014 |
| KR | 20140021293 A | | 2/2014 |
| WO | WO-2005104264 A1 | | 11/2005 |
| WO | WO-2011136482 A1 | | 11/2011 |
| WO | WO-2011136484 A1 | | 11/2011 |
| WO | WO-2013182263 A1 | | 12/2013 |

OTHER PUBLICATIONS

Machine translation for KR 2014-021293 (publication date: Feb. 2014). (Year: 2014).*

Machine translation for JP 2004-253298 (publication date: Sep. 2004). (Year: 2004).*

Newman et al., "The Synthesis of 4-Bromophenanthrene", *J. Amer. Chem. Soc.*, vol. 78, 4765 (3 pages) (1956).

International Search Report for PCT/EP2015/000271 dated Apr. 14, 2015.

Jwo-Huei, J., et al., "Artificial Dusk-Light Based on Organic Light Emitting Diodes", ACS Photonics, 2014, vol. 1, No. 1, pp. 27-31.

STN Registry Database: 936355-00-9 and 1509851-35-7, Jan. 22, 2019.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2015/000271, filed Feb. 9, 2015, which claims benefit of European Application No. 14000814.5, filed Mar. 7, 2014, both of which are incorporated herein by reference in their entirety.

The present application relates to a phenanthrenyl-arylamino compound of a formula (I) defined in detail below. The compound is preferably used in an electronic device, more preferably in an organic electroluminescent device (OLED).

Electronic devices in the context of this application are understood to mean what are called organic electronic devices, which contain organic semiconductor materials as functional materials. More particularly, these are understood to mean OLEDs.

The structure of OLEDs in which organic compounds are used as functional materials is described, for example, in U.S. Pat. Nos. 4,539,507, 5,151,629, EP 0676461 and WO 98/27136. In general, the term OLEDs is understood to mean electronic devices which have one or more layers comprising organic compounds and emit light on application of electrical voltage.

A great influence on the performance data of electronic devices is possessed by layers having a hole-transporting function, for example hole injection layers, hole transport layers, electron blocker layers and emitting layers.

It is known in the prior art that triarylamines can be used in the abovementioned layers as materials having hole-transporting properties. These may be monotriarylamines as described, for example, in JP 1995/053955, WO 2006/123667 and JP 2010/222268, or bis- or other oligoamines, as described, for example, in U.S. Pat. No. 7,504,163 or US 2005/0184657. Known examples of triarylamine compounds as materials having hole-transporting properties for OLEDs include tris-p-biphenylamine, N,N'-di-1-naphthyl-N,N'-diphenyl-1,1'-biphenyl-4,4'-diamine (NPB) and 4,4',4"-tris(3-methylphenylphenylamino)triphenylamine (MT-DATA).

Additionally known in the prior art is the use of phenanthrenyl-arylamino compounds in OLEDs, including as hole transport materials (WO 2013/182263 and C. Schmitz et al., Advanced Materials 2011, 11, 821). The phenanthrene derivatives disclosed in the documents cited are all substituted by an arylamino group in the 3 position of the phenanthrene.

Even though the compounds disclosed in the documents cited above are of good suitability for use in electronic devices, there is still a need for novel compounds for this use. More particularly, there is a need for compounds which lead to an improvement in the performance data of the electronic device, especially to an improvement of lifetime, efficiency and operating voltage. Especially for use in hole-transporting layers of the electronic devices, there is a continuous search for new materials having corresponding properties.

In the course of studies relating to novel materials for this use, it has now been found that, surprisingly, phenanthrene derivatives which have at least one arylamino group in the 1 or 4 position of the phenanthrene base skeleton and are defined in detail in the formula (I) below are of excellent suitability for use in OLEDs, especially in a hole-transporting layer.

The compounds found have one or more properties selected from very good hole-conducting properties, very good electron-blocking properties, high glass transition temperature, high oxidation stability, good solubility, low crystallinity and high thermal stability.

The present invention provides a compound of the formula (I)

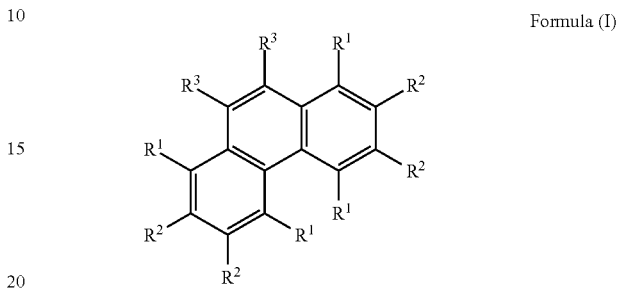

Formula (I)

where the symbols that occur are as follows:
$R^1$ is the same or different at each instance and is selected from H, D, F, C(=O)R$^6$, CN, Si(R$^6$)$_3$, N(R$^6$)$_2$, P(=O)(R$^6$)$_2$, OR$^6$, S(=O)R$^6$, S(=O)$_2$R$^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more R$^6$ radicals, heteroaromatic ring systems which have 5 to 40 aromatic ring atoms and may be substituted by one or more R$^6$ radicals, groups of the formula (A)

Formula (A)

and groups of the formula (B)

Formula (B)

where the alkyl, alkoxy, alkenyl and alkynyl groups mentioned may each be substituted by one or more R$^6$ radicals, and where one or more CH$_2$ groups in the alkyl, alkoxy, alkenyl and alkynyl groups mentioned may be replaced by —R$^6$C=CR$^6$—, —C≡C—, Si(R$^6$)$_2$, C=O, C=NR$^6$, —C(=O)O—, —C(=O)NR$^6$—, NR$^6$, P(=O)(R$^6$), —O—, —S—, SO or SO$_2$, and where the bond marked with * in each of formula (A) and formula (B) denotes the bond to the phenanthrene unit;
$R^2$, $R^3$ are the same or different at each instance and are selected from H, D, F, C(=O)R$^6$, CN, Si(R$^6$)$_3$, P(=O)(R$^6$)$_2$, OR$^6$, S(=O)R$^6$, S(=O)$_2$R$^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals, where the alkyl, alkoxy, alkenyl and alkynyl groups mentioned may each be substituted by one or more $R^6$ radicals, and where one or more $CH_2$ groups in the alkyl, alkoxy, alkenyl and alkynyl groups mentioned may be replaced by —$R^6C$=$CR^6$—, —C≡C—, $Si(R^6)_2$, C=O, C=$NR^6$, —C(=O)O—, —C(=O)$NR^6$—, $NR^6$, P(=O)($R^6$), —O—, —S—, SO or $SO_2$;

$R^6$ is the same or different at each instance and is selected from H, D, F, C(=O)$R^7$, CN, $Si(R^7)_3$, $N(R^7)_2$, P(=O)($R^7)_2$, $OR^7$, S(=O)$R^7$, S(=O)$_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more $R^7$ radicals, and heteroaromatic ring systems which have 5 to 40 aromatic ring atoms and may be substituted by one or more $R^7$ radicals, where the alkyl, alkoxy, alkenyl and alkynyl groups mentioned may each be substituted by one or more $R^7$ radicals, where one or more $CH_2$ groups in the alkyl, alkoxy, alkenyl and alkynyl groups mentioned may be replaced by —$R^7C$=$CR^7$—, —C≡C—, $Si(R^7)_2$, C=O, C=$NR^7$, —C(=O)O—, —C(=O)$NR^7$—, $NR^7$, P(=O)($R^7$), —O—, —S—, SO or $SO_2$, and where two or more $R^6$ substituents may be joined to one another and may form a ring;

$R^7$ is the same or different at each instance and is selected from H, D, F, CN and aliphatic, aromatic or heteroaromatic organic radicals having 1 to 20 carbon atoms, in which one or more hydrogen atoms may also be replaced by D, F or CN;

$Ar^1$ is the same or different at each instance and is selected from aromatic ring systems which have 6 to 40 aromatic ring atoms and may be substituted by one or more $R^4$ radicals, and heteroaromatic ring systems which have 5 to 40 aromatic ring atoms and may be substituted by one or more $R^4$ radicals;

$Ar^2$ is the same or different at each instance and is selected from aromatic ring systems which have 6 to 40 aromatic ring atoms and may be substituted by one or more $R^4$ radicals, and heteroaromatic ring systems which have 5 to 40 aromatic ring atoms and may be substituted by one or more $R^4$ radicals;

$R^4$ is the same or different at each instance and is selected from H, D, F, C(=O)$R^6$, CN, $Si(R^6)_3$, $N(R^6)_2$, P(=O)($R^6)_2$, $OR^6$, S(=O)$R^6$, S(=O)$_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals, where the alkyl, alkoxy, alkenyl and alkynyl groups mentioned may each be substituted by one or more $R^6$ radicals, where one or more $CH_2$ groups in the alkyl, alkoxy, alkenyl and alkynyl groups mentioned may be replaced by —$R^6C$=$CR^6$—, —C≡C—, $Si(R^6)_2$, C=O, C=$NR^6$, —C(=O)O—, —C(=O)$NR^6$—, $NR^6$, P(=O)($R^6$), —O—, —S—, SO or $SO_2$, and where two or more $R^4$ substituents may be joined to one another and may form a ring;

X is the same or different at each instance and is selected from single bonds, $BR^5$, $C(R^5)_2$, —$C(R^5)_2$—$C(R^5)_2$—, —$C(R^6)$=$C(R^6)$—, —$C(R^5)_2$—O—, —$C(R^5)_2$—$NR^5$—, $Si(R^5)_2$, C=O, $NR^6$, $PR^5$, P(=O)$R^5$, O, S, S=O, $SO_2$ and ortho-phenylene optionally substituted by $R^5$ radicals;

$R^5$ is the same or different at each instance and is selected from H, D, F, C(=O)$R^6$, CN, $Si(R^6)_3$, $N(R^6)_2$, P(=O)($R^6)_2$, $OR^6$, S(=O)$R^6$, S(=O)$_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more $R^6$ radicals, and heteroaromatic ring systems which have 5 to 40 aromatic ring atoms and may be substituted by one or more $R^6$ radicals, where the alkyl, alkoxy, alkenyl and alkynyl groups mentioned may each be substituted by one or more $R^6$ radicals, where one or more $CH_2$ groups in the alkyl, alkoxy, alkenyl and alkynyl groups mentioned may be replaced by —$R^6C$=$CR^6$—, —C≡C—, $Si(R^6)_2$, C=O, C=$NR^6$, —C(=O)O—, —C(=O)$NR^6$—, $NR^6$, P(=O)($R^6$), —O—, —S—, SO or $SO_2$, and where two or more $R^5$ substituents may be joined to one another and may form a ring;

i is the same or different at each instance and is 0 or 1, where at least one $R^1$ radical in the compound of the formula (I) is selected from groups of the formula (A) and groups of the formula (B).

An aryl group in the context of this invention contains 6 to 60 aromatic ring atoms; a heteroaryl group in the context of this invention contains 5 to 60 aromatic ring atoms, at least one of which is a heteroatom. The heteroatoms are preferably selected from N, O and S. This is the fundamental definition. If other preferences are stated in the description of the present invention, for example with regard to the number of aromatic ring atoms or of heteroatoms present, these are applicable.

An aryl group or heteroaryl group is understood here to mean either a simple aromatic cycle, i.e. benzene, or a simple heteroaromatic cycle, for example pyridine, pyrimidine or thiophene, or a fused (annelated) aromatic or heteroaromatic polycycle, for example naphthalene, phenanthrene, quinoline or carbazole.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 60 carbon atoms in the ring system. A heteroaromatic ring system in the context of this invention contains 5 to 60 aromatic ring atoms, at least one of which is a heteroatom. The heteroatoms are preferably selected from N, O and/or S. An aromatic or heteroaromatic ring system in the context of this invention shall be understood to mean a system which does not necessarily contain only aryl or heteroaryl groups but in which it is also possible for a plurality of aryl or heteroaryl groups to be bonded by a single bond or by a non-aromatic unit, for example one or more optionally substituted C, Si, N, O or S atoms. In this case, the non-aromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene shall also be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl or heteroaryl groups are joined to one another via single bonds are also regarded as aromatic or heteroaromatic ring systems in the context of this invention, for example systems such as biphenyl, terphenyl or diphenyltriazine.

An aromatic or heteroaromatic ring system which has 5-60 aromatic ring atoms and may also be substituted in each case by radicals as defined above and which may be joined to the aromatic or heteroaromatic system via any desired positions is especially understood to mean groups derived from the groups mentioned above under aryl and heteroaryl groups, and also from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole or combinations of these groups.

In the context of the present invention, a straight-chain alkyl group having 1 to 40 carbon atoms and a branched or cyclic alkyl group having 3 to 40 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals. An alkoxy or thioalkyl group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

It is preferable that the compound of the formula (I), aside from the phenanthrene group, does not contain any further fused aryl group having more than 10 aromatic ring atoms. More preferably, the compound of the formula (I), aside from the phenanthrene group, does not contain any further fused aryl group having more than 10 aromatic ring atoms or any fused heteroaryl group having more than 12 aromatic ring atoms.

The term "fused aryl or heteroaryl group" in the context of the present application is understood to mean a group consisting of two or more simple aromatic or heteroaromatic rings fused to one another. Examples of a fused aryl group are naphthalene, anthracene and phenanthrene. Examples of a fused heteroaryl group are acridine and phenanthridine.

It is preferable that at least one $R^1$ radical in the compound of the formula (I) is selected from groups of the formula (A). More preferably, exactly one $R^1$ radical in the compound of the formula (I) is selected from groups of the formula (A), or exactly two $R^1$ radicals in the compound of the formula (I) are selected from groups of the formula (A).

It is preferable that exactly one $R^1$ radical in the compound of the formula (I) is selected from groups of the formula (A) and groups of the formula (B), or that exactly two $R^1$ radicals in the compound of the formula (I) are selected from groups of the formula (A) and groups of the formula (B).

If exactly two $R^1$ radicals in the compound of the formula (I) are selected from groups of the formula (A) and groups of the formula (B), it is preferable that exactly one of these $R^1$ radicals is bonded in the 1 position of the phenanthrene and exactly one of these $R^1$ radicals is bonded in the 4 position of the phenanthrene.

It is additionally preferable that the case in which both one $R^1$ radical in the 4 position of the phenanthrene and one $R^1$ radical in the 5 position of the phenanthrene are selected from groups of the formula (A) and groups of the formula (B) is ruled out.

It is additionally preferable that the case in which both one $R^1$ radical in the 1 position of the phenanthrene and one $R^1$ radical in the 8 position of the phenanthrene are selected from groups of the formula (A) and groups of the formula (B) is ruled out.

The numbering of the positions in the phenanthrene base skeleton in the context of the present application is as follows:

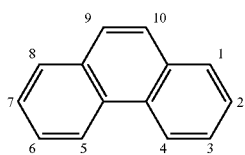

It is preferable that one or two indices i per group of the formula (B) are 1, and it is particularly preferable that exactly one index i per group of the formula (B) is 1.

Most preferably, the index i at each instance is 0.

Preferred embodiments of the (A) group are selected from the following formulae (A-1) to (A-7):

Formula (A-1)

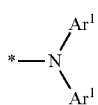

Formula (A-2)

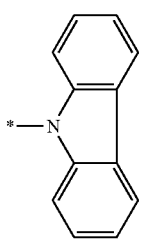

Formula (A-3)

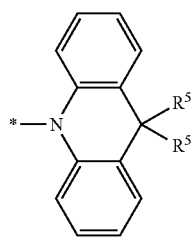

Formula (A-4)

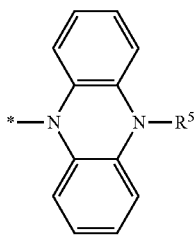

Formula (A-5)

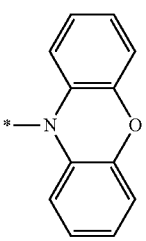

Formula (A-6)

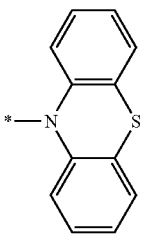

Formula (A-7)

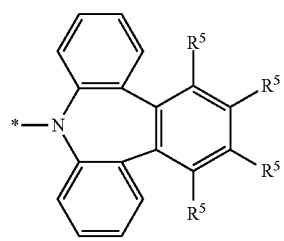

which may each be substituted by $R^4$ radicals at the unoccupied positions, and where the bond marked with * represents the position of attachment to the phenanthrenyl base skeleton.

Among these, particular preference is given to the formula (A-1).

Preferred embodiments of the (B) group are selected from the following formulae (B-1) to (B-15):

Formula (B-1)

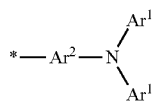

Formula (B-2)

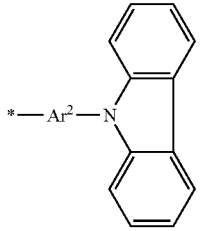

Formula (B-3)

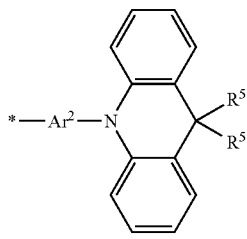

Formula (B-4)

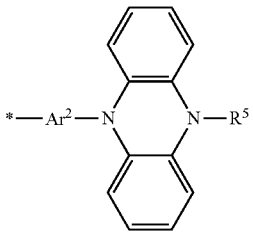

-continued

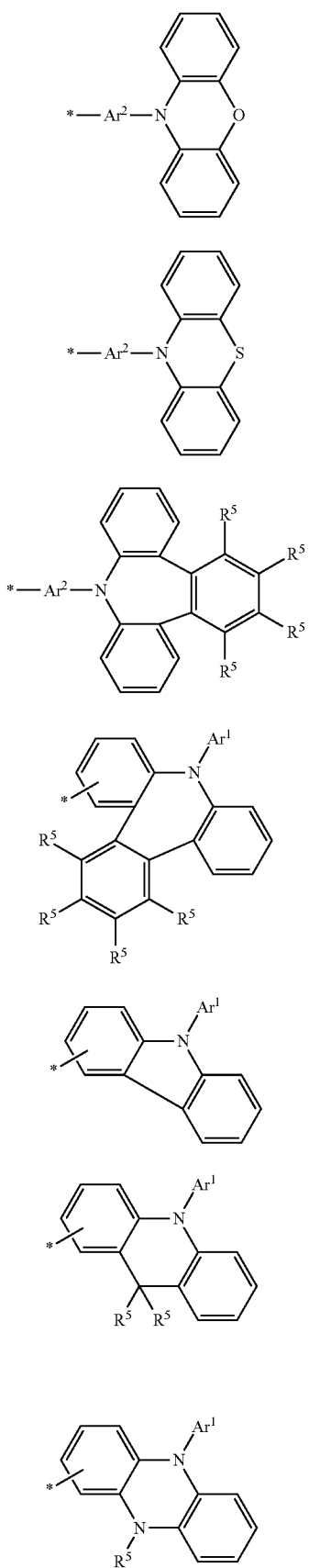

Formula (B-5)

Formula (B-6)

Formula (B-7)

Formula (B-8)

Formula (B-9)

Formula (B-10)

Formula (B-11)

-continued

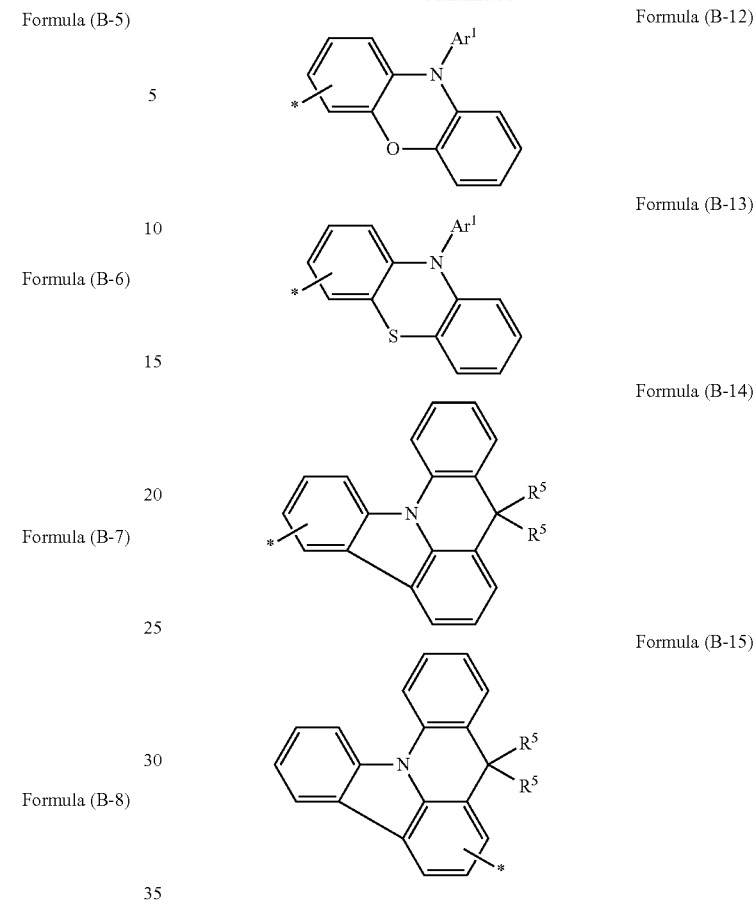

Formula (B-12)

Formula (B-13)

Formula (B-14)

Formula (B-15)

which may each be substituted by $R^4$ radicals at the unoccupied positions, and where the bond marked with * represents the position of attachment to the phenanthrenyl base skeleton.

Among these, particular preference is given to the formula (B-1).

It is preferable that $Ar^1$ is the same or different at each instance and is selected from aromatic ring systems which have 6 to 24 aromatic ring atoms and may be substituted by one or more $R^4$ radicals, and heteroaromatic ring systems which have 5 to 24 aromatic ring atoms and may be substituted by one or more $R^4$ radicals. More preferably, $Ar^1$ is the same or different at each instance and is selected from aromatic ring systems which have 12 to 24 aromatic ring atoms and may be substituted by one or more $R^4$ radicals.

Preferably, two $Ar^1$ groups in formula (A) or (B) bonded to the same nitrogen atom are not the same.

Preferably, the $Ar^1$ groups each contain at least one group selected from benzene, naphthalene, phenanthrene, fluoranthene, biphenyl, terphenyl, quaterphenyl, fluorene, spirobifluorene, furan, benzofuran, isobenzofuran, dibenzofuran, thiophene, benzothiophene, isobenzothiophene, dibenzothiophene, indole, isoindole, carbazole, indolocarbazole, indenocarbazole, pyridine, quinoline, isoquinoline, acridine, phenanthridine, benzimidazole, pyrimidine, pyrazine and triazine, where the groups mentioned may each be substituted by one or more $R^4$ radicals.

Preferably, $Ar^1$ is selected from groups of the following formulae ($Ar^1$-1) to ($Ar^1$-59):

-continued
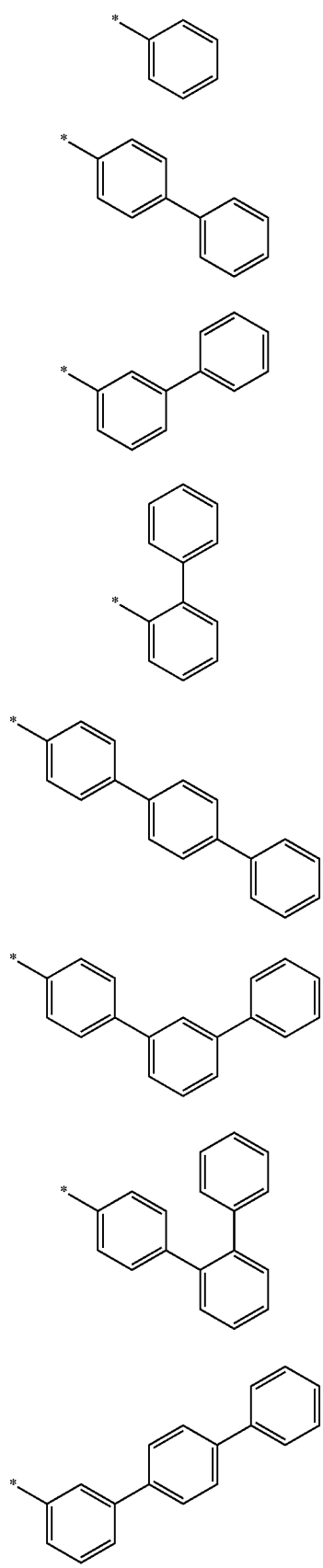
Formula (Ar¹-1)
Formula (Ar¹-2)
Formula (Ar¹-3)
Formula (Ar¹-4)
Formula (Ar¹-5)
Formula (Ar¹-6)
Formula (Ar¹-7)
Formula (Ar¹-8)
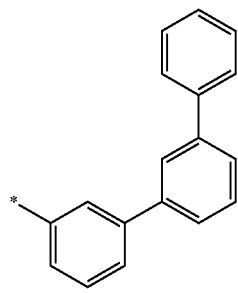
Formula (Ar¹-9)
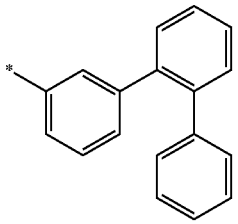
Formula (Ar¹-10)
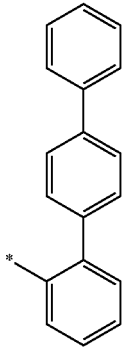
Formula (Ar¹-11)
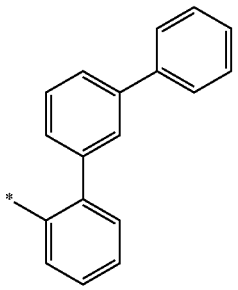
Formula (Ar¹-12)
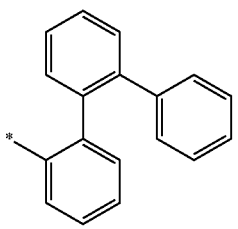
Formula (Ar¹-13)

Formula (Ar¹-14)
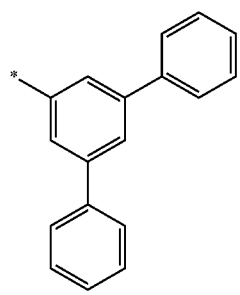
Formula (Ar¹-15)
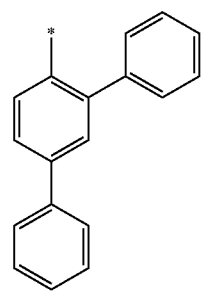
Formula (Ar¹-16)
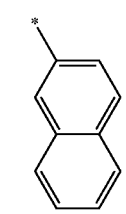
Formula (Ar¹-17)
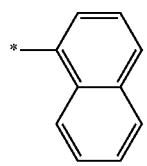
Formula (Ar¹-18)
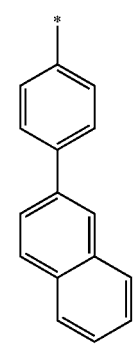
Formula (Ar¹-19)
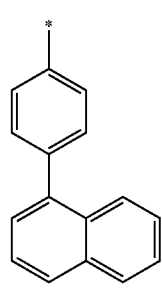
Formula (Ar¹-20)
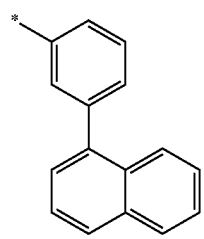
Formula (Ar¹-21)
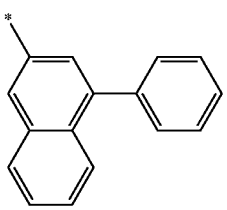
Formula (Ar¹-22)
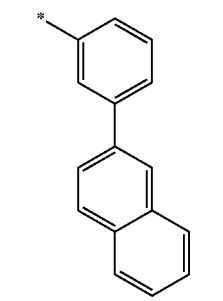
Formula (Ar¹-23)
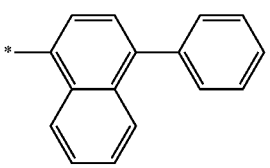
Formula (Ar¹-24)
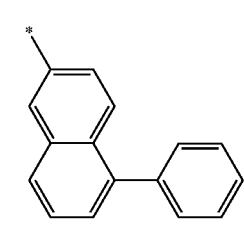
Formula (Ar¹-25)
Formula (Ar¹-26)
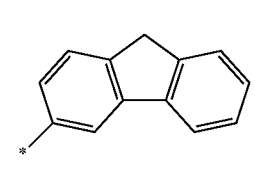
Formula (Ar¹-27)

Formula (Ar¹-28)
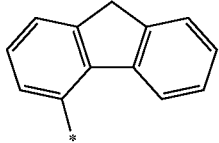
Formula (Ar¹-29)
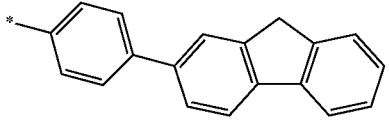
Formula (Ar¹-30)
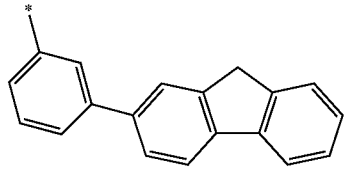
Formula (Ar¹-31)
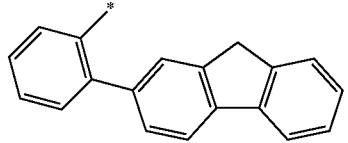
Formula (Ar¹-32)
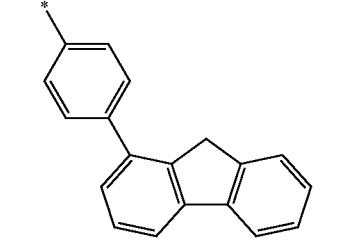
Formula (Ar¹-33)
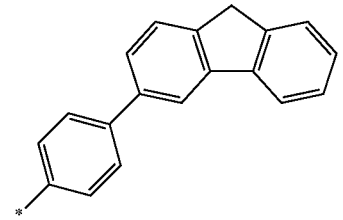
Formula (Ar¹-34)
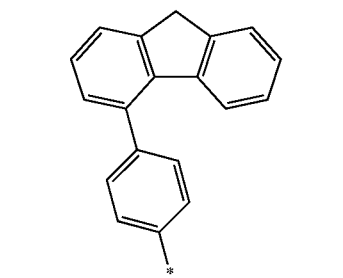
Formula (Ar¹-35)
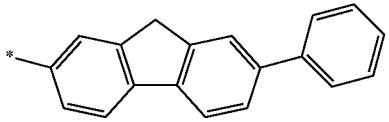
Formula (Ar¹-36)
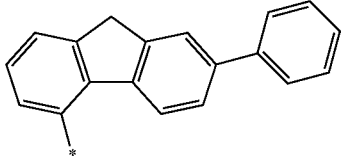
Formula (Ar¹-37)
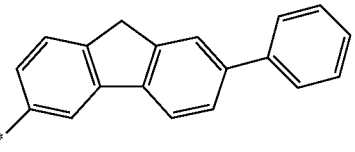
Formula (Ar¹-38)
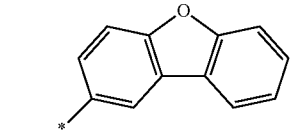
Formula (Ar¹-39)
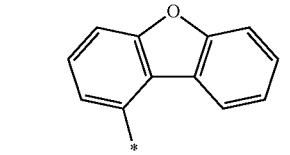
Formula (Ar¹-40)
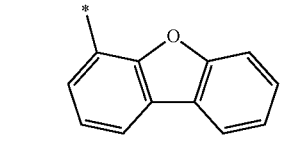
Formula (Ar¹-41)
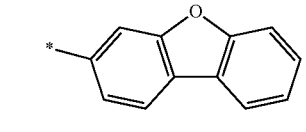
Formula (Ar¹-42)
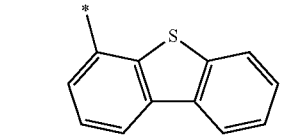
Formula (Ar¹-43)
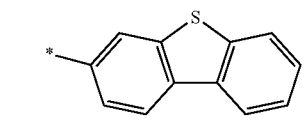
Formula (Ar¹-44)
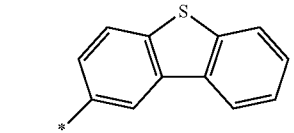
Formula (Ar¹-45)
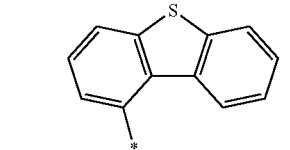

Formula (Ar¹-46)
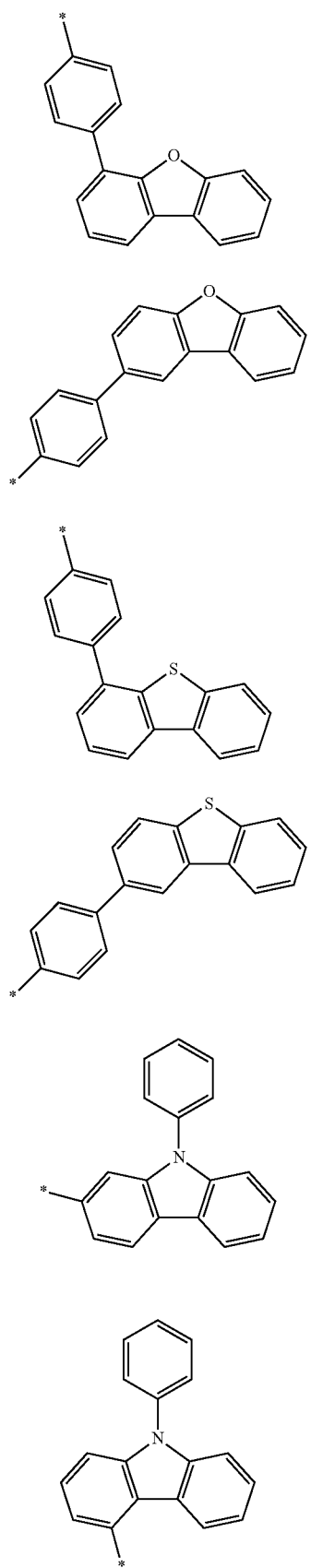
Formula (Ar¹-47)
Formula (Ar¹-48)
Formula (Ar¹-49)
Formula (Ar¹-50)
Formula (Ar¹-51)
Formula (Ar¹-52)
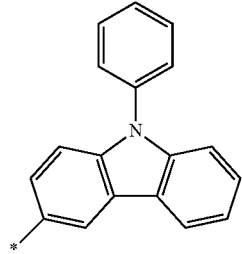
Formula (Ar¹-53)
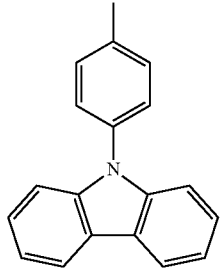
Formula (Ar¹-54)
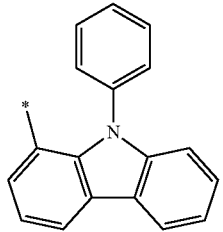
Formula (Ar¹-55)
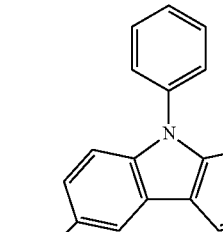
Formula (Ar¹-56)
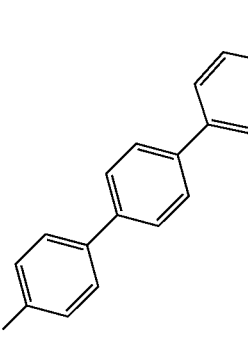

-continued

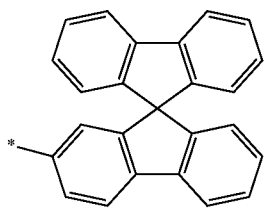
Formula (Ar¹-57)

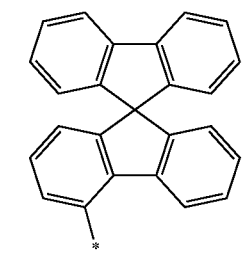
Formula (Ar¹-58)

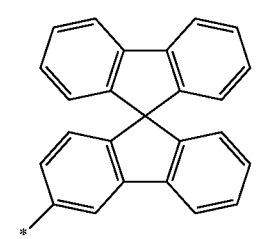
Formula (Ar¹-59)

where the bond marked with * in each case represents the bond to the nitrogen atom, and where the groups may bear $R^4$ radicals at their unoccupied positions.

It is preferable that $Ar^2$ is the same or different at each instance and is selected from aromatic ring systems which have 6 to 24 aromatic ring atoms and may be substituted by one or more $R^4$ radicals, and heteroaromatic ring systems which have 5 to 24 aromatic ring atoms and may be substituted by one or more $R^4$ radicals. More preferably, $Ar^2$ is the same or different at each instance and is selected from aromatic ring systems which have 6 to 13 aromatic ring atoms and may be substituted by one or more $R^4$ radicals.

Preferably, $Ar^2$ is selected from groups of the following formulae (Ar²-1) to (Ar²-14):

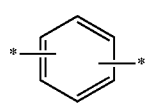
Formula (Ar²-1)

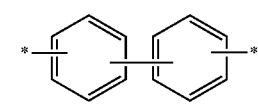
Formula (Ar²-2)

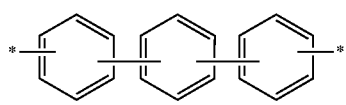
Formula (Ar²-3)

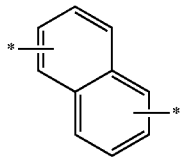
Formula (Ar²-4)

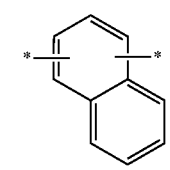
Formula (Ar²-5)

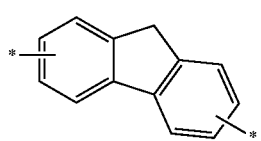
Formula (Ar²-6)

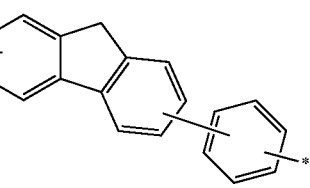
Formula (Ar²-7)

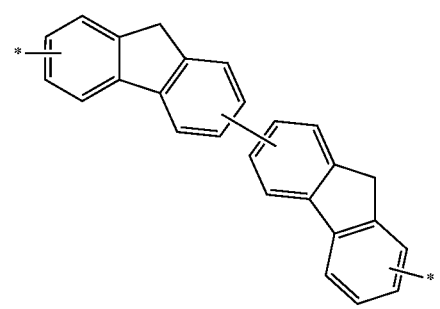
Formula (Ar²-8)

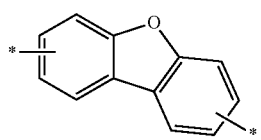
Formula (Ar²-9)

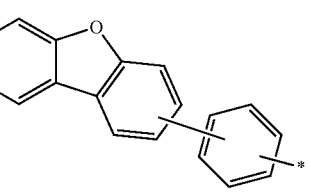
Formula (Ar²-10)

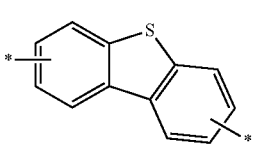
Formula (Ar²-11)

-continued

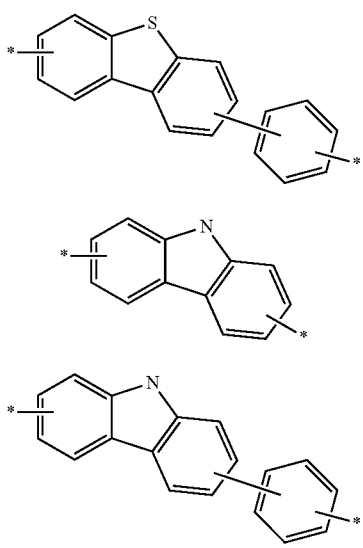

Formula (Ar²-12)

Formula (Ar²-13)

Formula (Ar²-14)

where the groups may each be substituted by $R^4$ radicals at the unoccupied positions and where the bonds marked with * each indicate the bonds to the rest of the compound.

X groups are preferably selected from single bonds, $C(R^5)_2$, —$C(R^5)_2$—$C(R^5)_2$—, —$C(R^5)$=$C(R^5)$—, $Si(R^5)_2$, C=O, $NR^5$, O, S, S=O, $SO_2$ and ortho-phenylene optionally substituted by $R^6$ radicals.

$R^1$ is preferably the same or different at each instance and is selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^6$ radicals, heteroaromatic ring systems which have 5 to 24 aromatic ring atoms and may be substituted by one or more $R^6$ radicals, groups of the formula (A), as defined above, and groups of the formula (B), where the alkyl and alkoxy groups mentioned may each be substituted by one or more $R^6$ radicals and where one or more $CH_2$ groups in the alkyl and alkoxy groups mentioned may be replaced by —C≡C—, —$R^6C$=$CR^6$—, $Si(R^6)_2$, C=O, C=$NR^6$, —$NR^6$—, —O—, —S—, —C(=O)O— or —C(=O)$NR^6$—.

$R^2$, $R^3$ are preferably the same or different at each instance and are selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^6$ radicals, and heteroaromatic ring systems which have 5 to 24 aromatic ring atoms and may be substituted by one or more $R^6$ radicals, where the alkyl and alkoxy groups mentioned may each be substituted by one or more $R^6$ radicals and where one or more $CH_2$ groups in the alkyl and alkoxy groups mentioned may be replaced by —C≡C—, —$R^6C$=$CR^6$—, $Si(R^6)_2$, C=O, C=$NR^6$, —$NR^6$—, —O—, —S—, —C(=O)O— or —C(=O)$NR^6$—.

$R^4$ and $R^5$ are preferably the same or different at each instance and are selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^6$ radicals, and heteroaromatic ring systems which have 5 to 24 aromatic ring atoms and may be substituted by one or more $R^6$ radicals, where the alkyl and alkoxy groups mentioned may each be substituted by one or more $R^6$ radicals and where one or more $CH_2$ groups in the alkyl and alkoxy groups mentioned may be replaced by —C≡C—, —$R^6C$=$CR^6$—, $Si(R^6)_2$, C=O, C=$NR^6$, —$NR^6$—, —O—, —S—, —C(=O)O— or —C(=O)$NR^6$—.

$R^5$ groups which are constituents of a $C(R^5)_2$, —$C(R^5)_2$—$C(R^5)_2$—, —$C(R^5)$=$C(R^5)$—, $Si(R^5)_2$ and $NR^5$ group are preferably selected from straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^6$ radicals, and heteroaromatic ring systems which have 5 to 24 aromatic ring atoms and may be substituted by one or more $R^6$ radicals.

$R^6$ is preferably the same or different at each instance and is selected from H, D, F, CN, $Si(R^7)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^7$ radicals, and heteroaromatic ring systems which have 5 to 24 aromatic ring atoms and may be substituted by one or more $R^7$ radicals, where the alkyl and alkoxy groups mentioned may each be substituted by one or more $R^7$ radicals and where one or more $CH_2$ groups in the alkyl and alkoxy groups mentioned may be replaced by —C≡C—, —$R^7C$=$CR^7$—, $Si(R^7)_2$, C=O, C=$NR^7$, —$NR^7$—, —O—, —S—, —C(=O)O— or —C(=O)$NR^7$—.

Preferred embodiments of the compound of the formula (I) correspond to the following formulae (I-1) to (I-24):

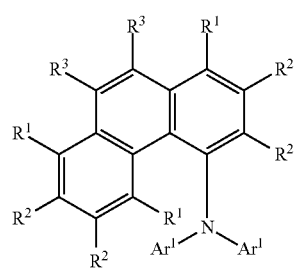

Formula (I-1)

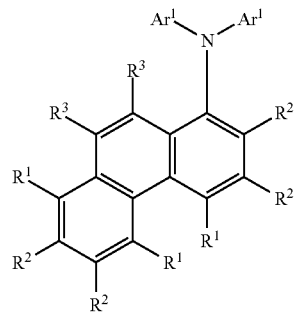

Formula (I-2)

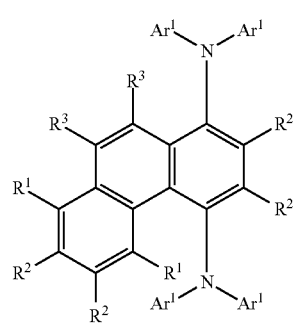
Formula (I-3)
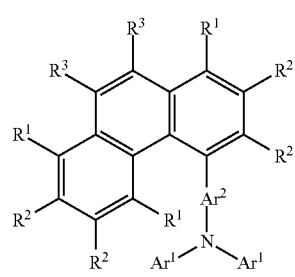
Formula (I-4)
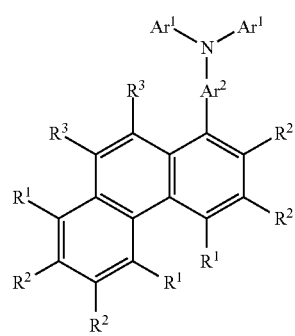
Formula (I-5)
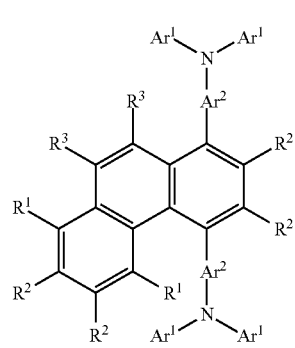
Formula (I-6)
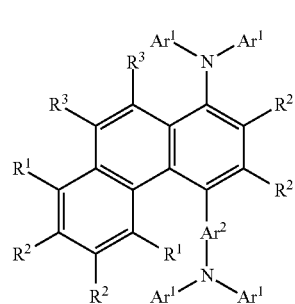
Formula (I-7)
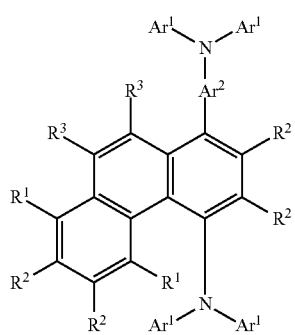
Formula (I-8)
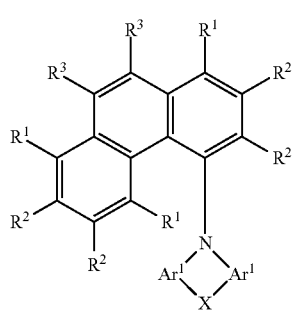
Formula (I-9)
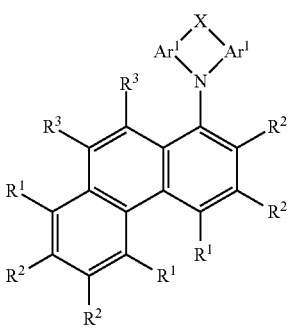
Formula (I-10)
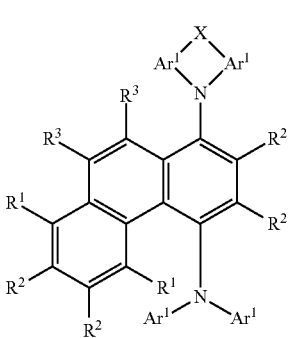
Formula (I-11)
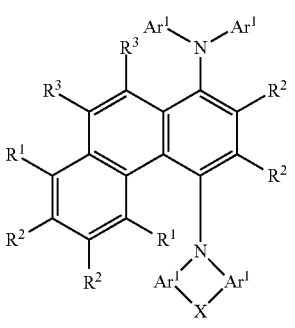
Formula (I-12)

Formula (I-13)
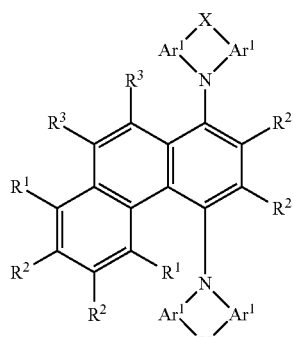
Formula (I-14)
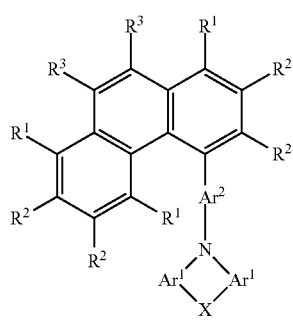
Formula (I-15)
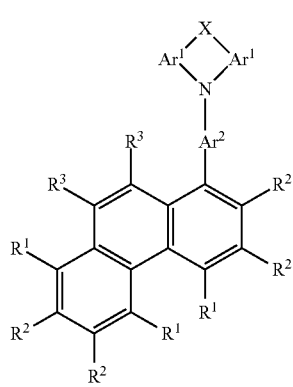
Formula (I-16)
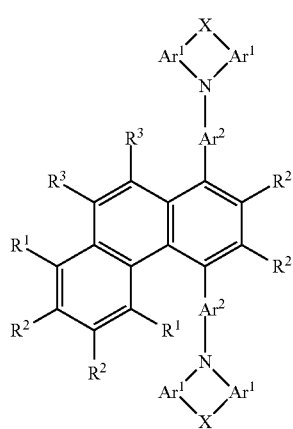
Formula (I-17)
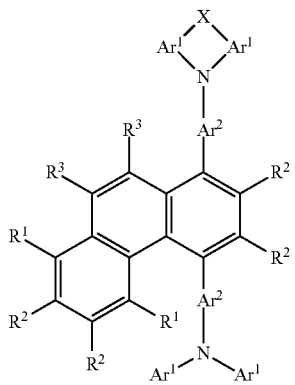
Formula (I-18)
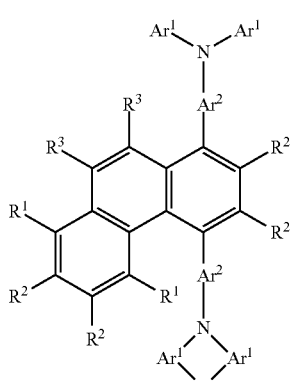
Formula (I-19)
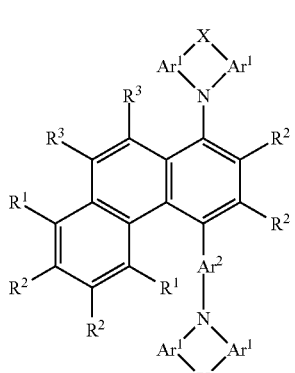
Formula (I-20)
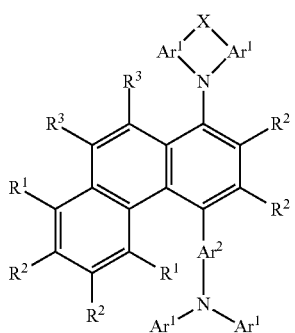

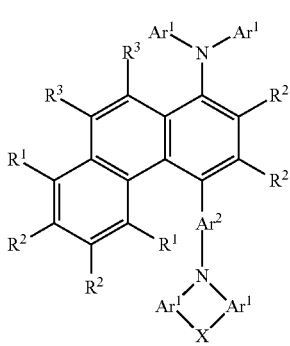

Formula (I-21)

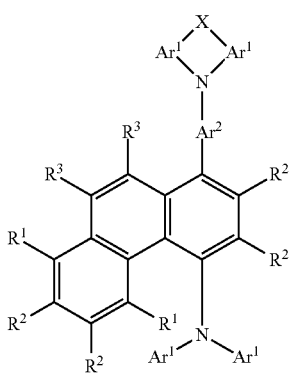

Formula (I-22)

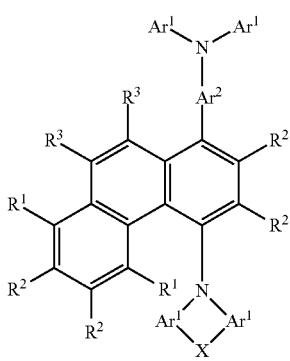

Formula (I-23)

Formula (I-24)

where the groups that occur are as defined above, and R¹ is the same or different at each instance and is selected from H, D, F, C(=O)R⁶, CN, Si(R⁶)₃, N(R⁶)₂, P(=O)(R⁶)₂, OR⁶, S(=O)R⁶, S(=O)₂R⁶, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more R⁶ radicals, and heteroaromatic ring systems which have 5 to 40 aromatic ring atoms and may be substituted by one or more R⁶ radicals, where the alkyl, alkoxy, alkenyl and alkynyl groups mentioned may each be substituted by one or more R⁶ radicals and where one or more CH₂ groups in the alkyl, alkoxy, alkenyl and alkynyl groups mentioned may be replaced by —R⁶C=CR⁶—, —C≡C—, Si(R⁶)₂, C=O, C=NR⁶, —C(=O)O—, —C(=O)NR⁶—, NR⁶, P(=O)(R⁶), —O—, —S—, SO or SO₂.

Among the formulae (I-1) to (I-24), preference is given to the formulae (I-1), (I-2), (I-9) and (I-10), particular preference to the formulae (I-1) and (I-2).

The combination of the preferred formulae (I-1) to (I-24) with the preferred embodiments of the Ar¹, Ar², X, R¹ to R⁶ groups is particularly preferred.

For the formulae (I-1) to (I-24), it is particularly preferable that the R¹, R² and R³ groups are the same or different at each instance and are selected from H, D, F, CN, Si(R⁶)₃, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more R⁶ radicals, and heteroaromatic ring systems which have 5 to 24 aromatic ring atoms and may be substituted by one or more R⁶ radicals, where the alkyl and alkoxy groups mentioned may each be substituted by one or more R⁶ radicals and where one or more CH₂ groups in the alkyl or alkoxy groups mentioned may be replaced by —C≡C—, —R⁶C=CR⁶—, Si(R⁶)₂, C=O, C=NR⁶, —NR⁶—, —O—, —S—, —C(=O)O— or —C(=O)NR⁶—. It is very particularly preferable that the R¹, R² and R³ groups are the same or different at each instance and are selected from H, F, CN, Si(R⁶)₃, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more R⁶ radicals, and heteroaromatic ring systems which have 5 to 24 aromatic ring atoms and may be substituted by one or more R⁶ radicals.

Examples of compounds of formula (I) are depicted below:

1

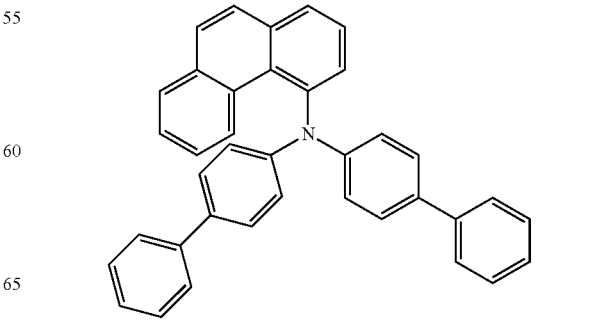

2
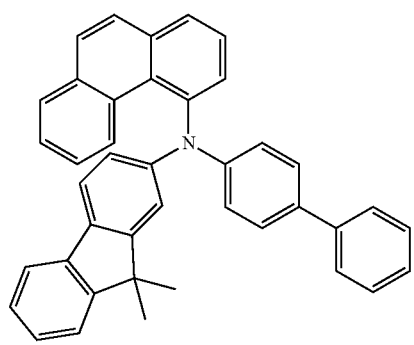
3
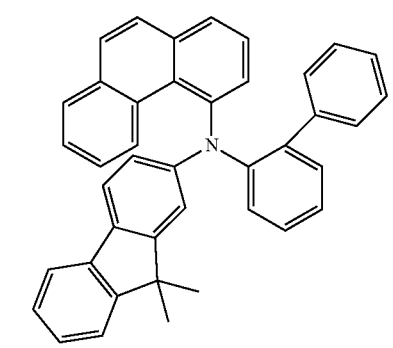
4
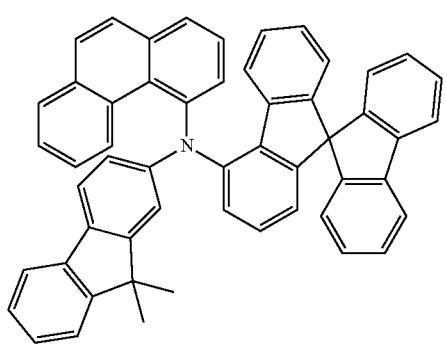
5
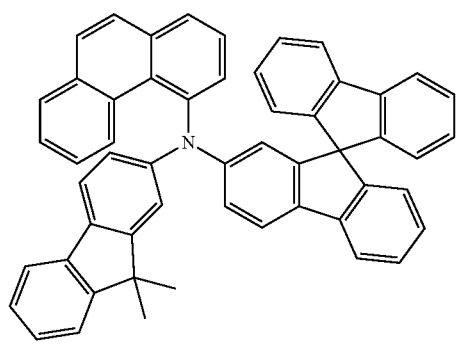
6
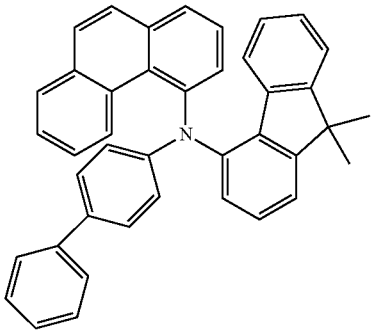
7
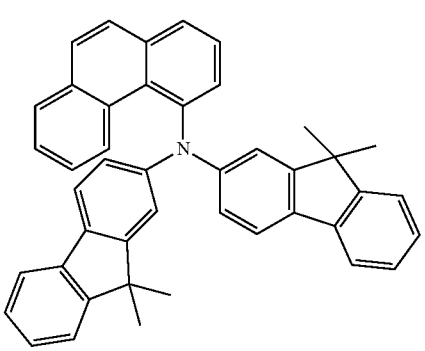
8
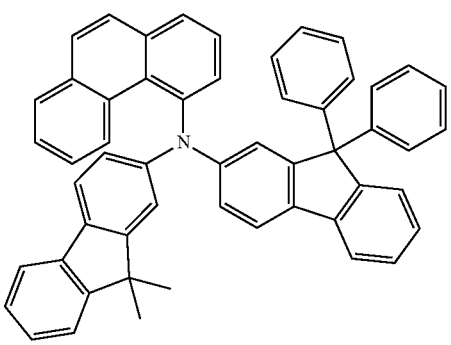
9
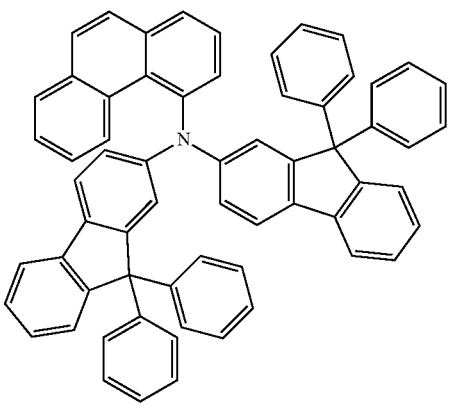

10
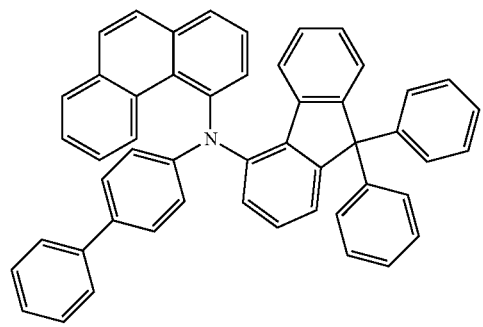
11
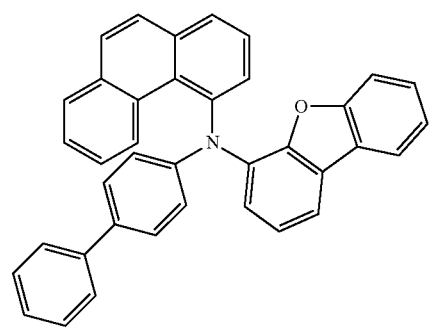
12
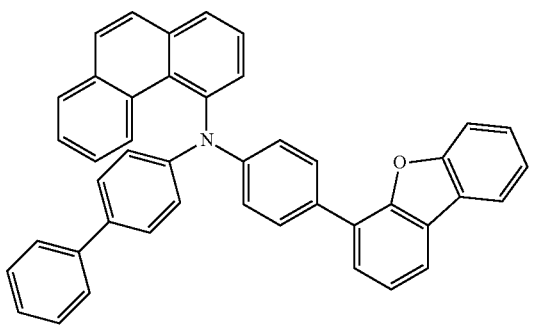
13
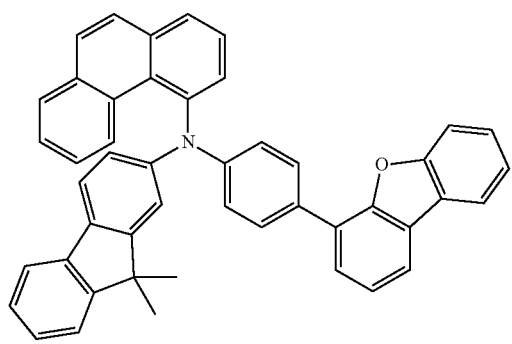
14
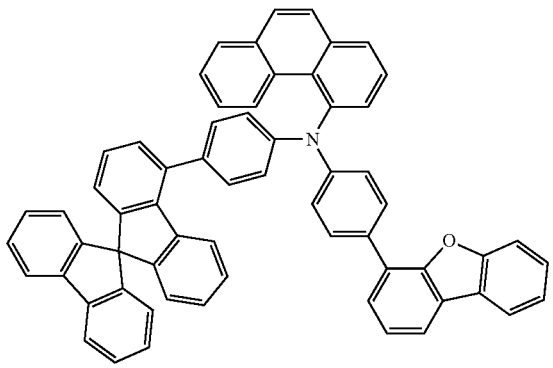
15
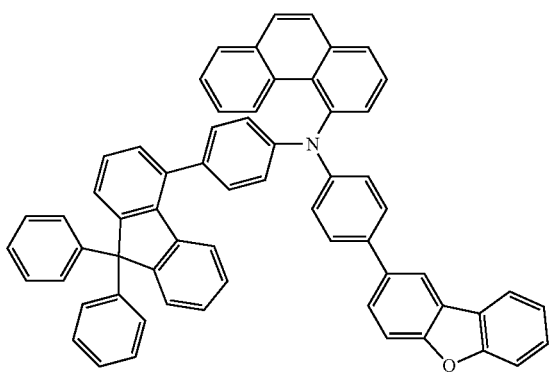
16
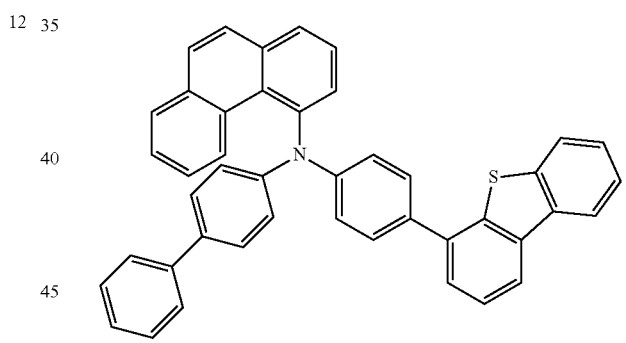
17
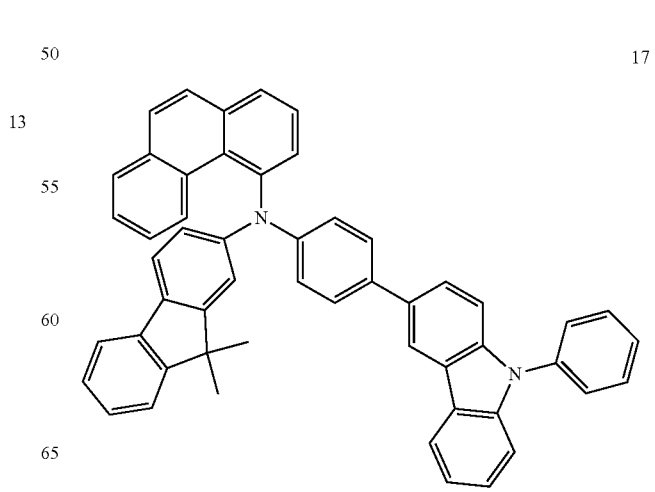

18
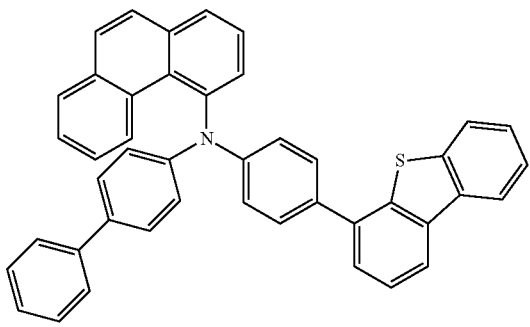
19
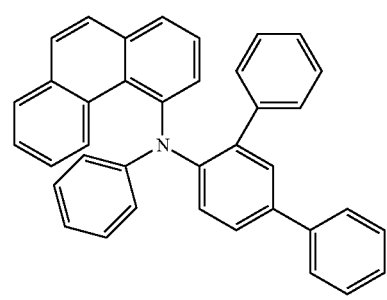
20
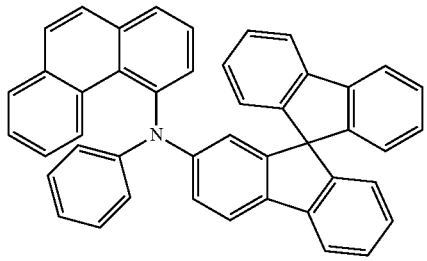
21
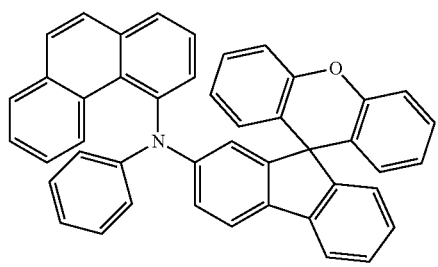
22
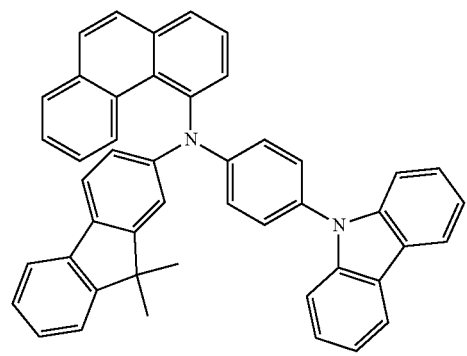
23
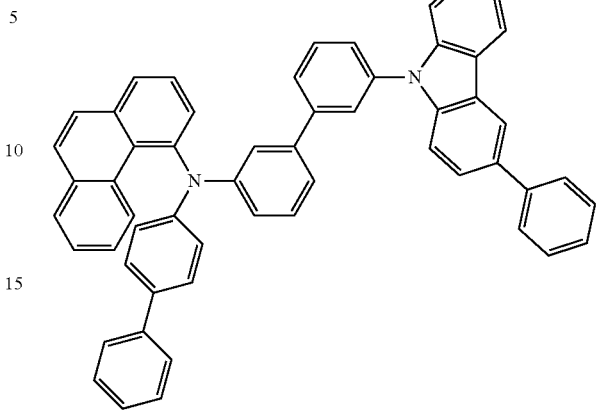
24
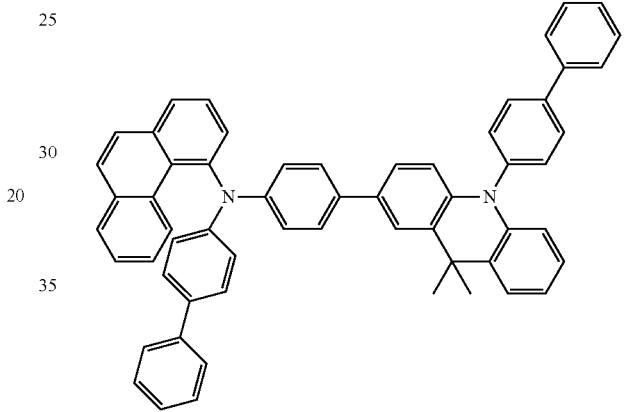
25
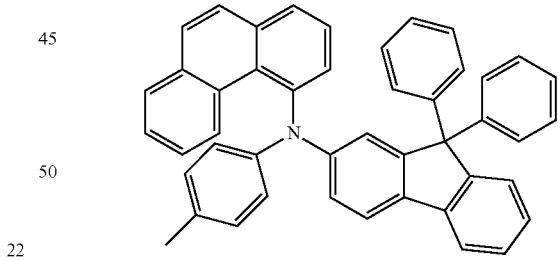
26
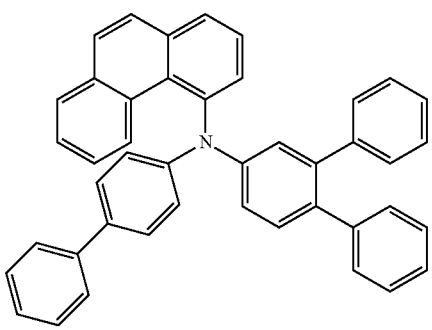

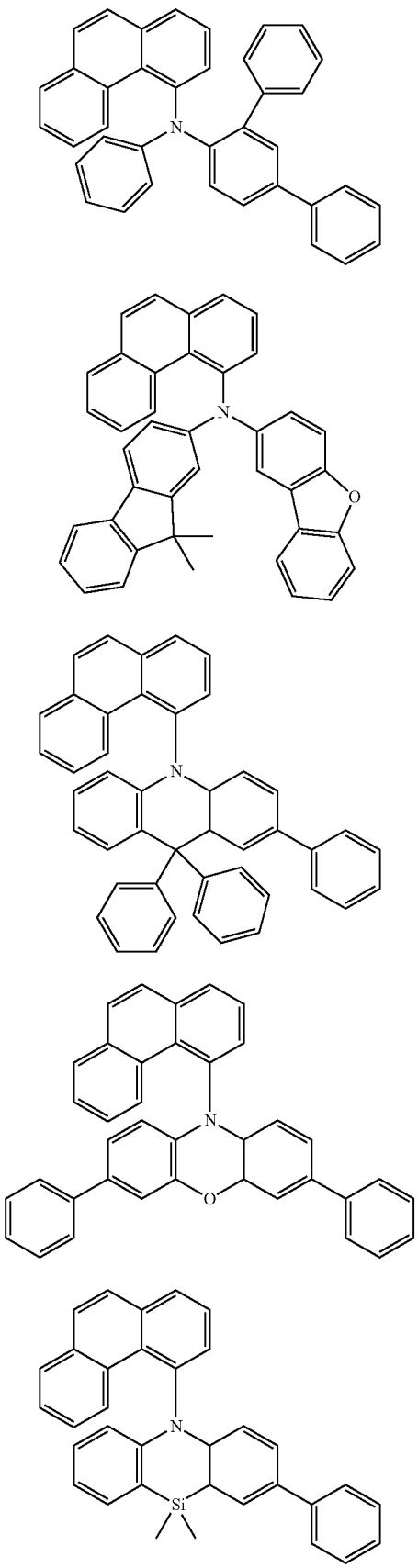
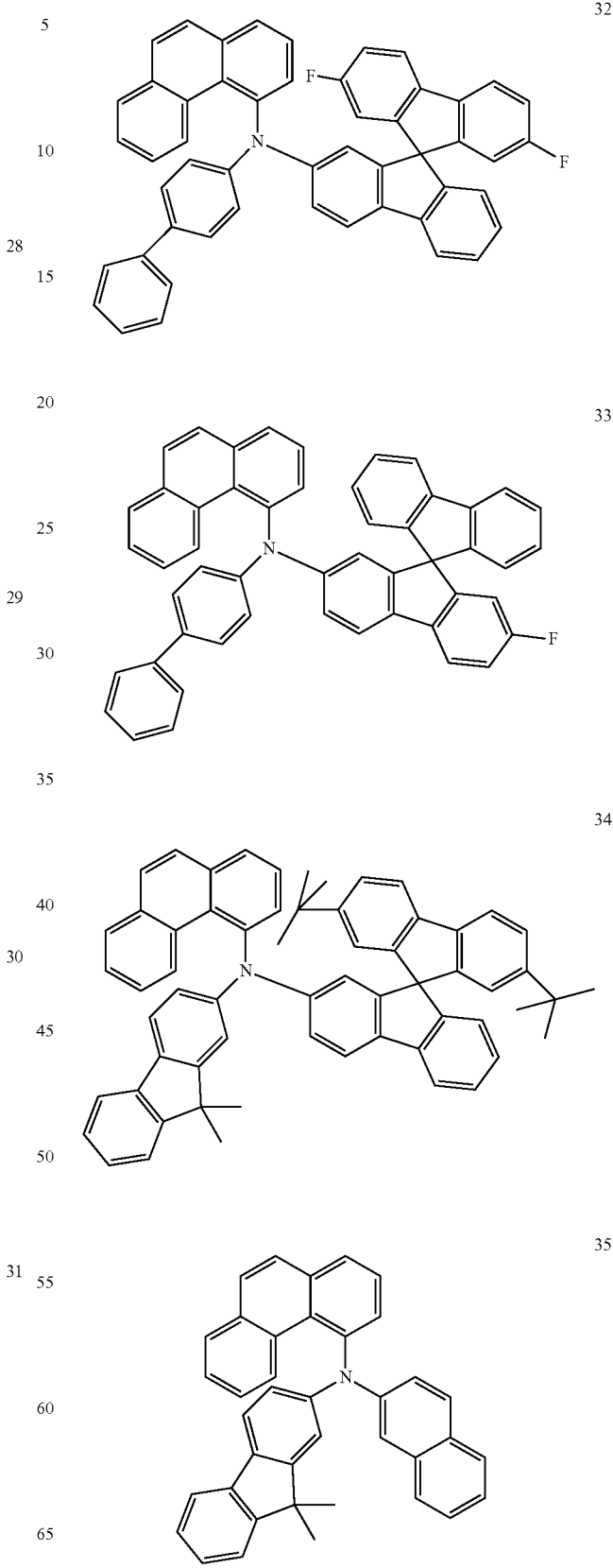

36
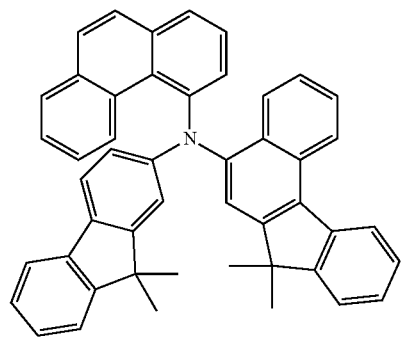
37
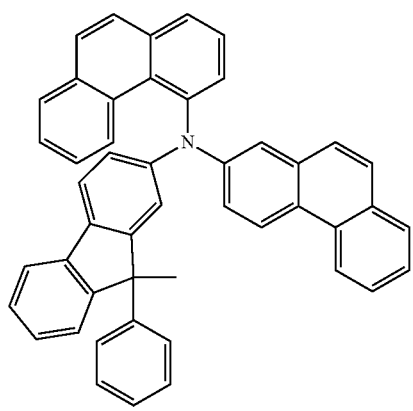
38
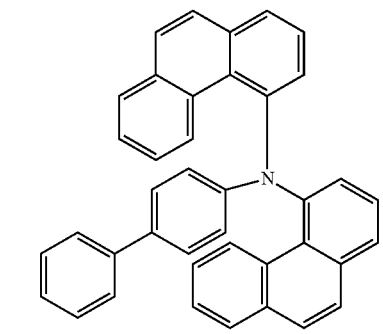
39
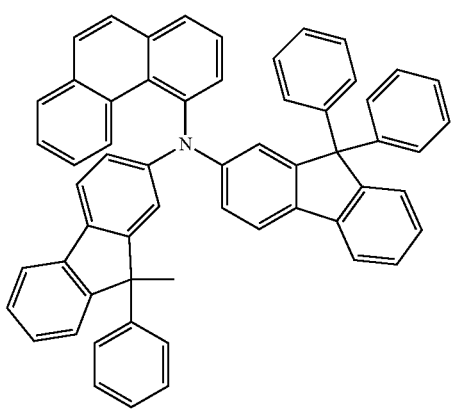
40
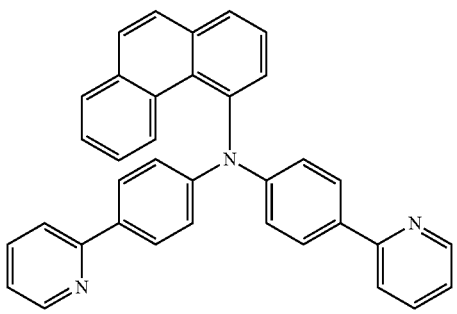
41
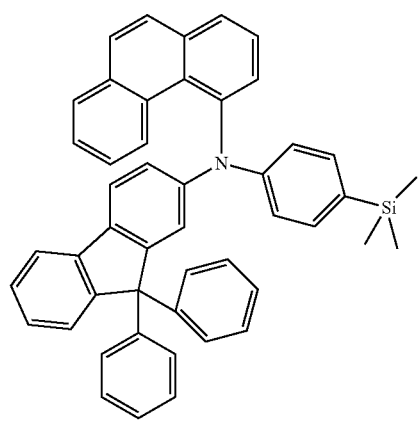
42
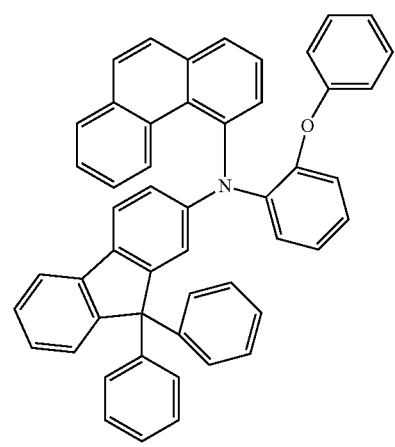
43
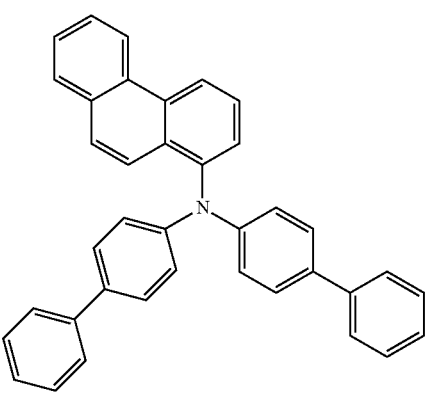

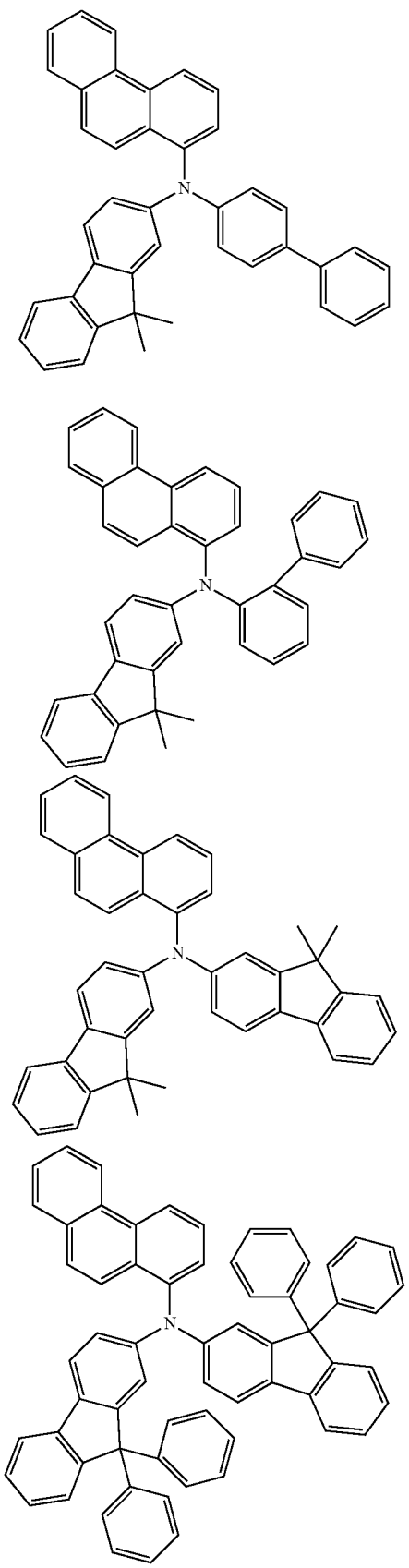
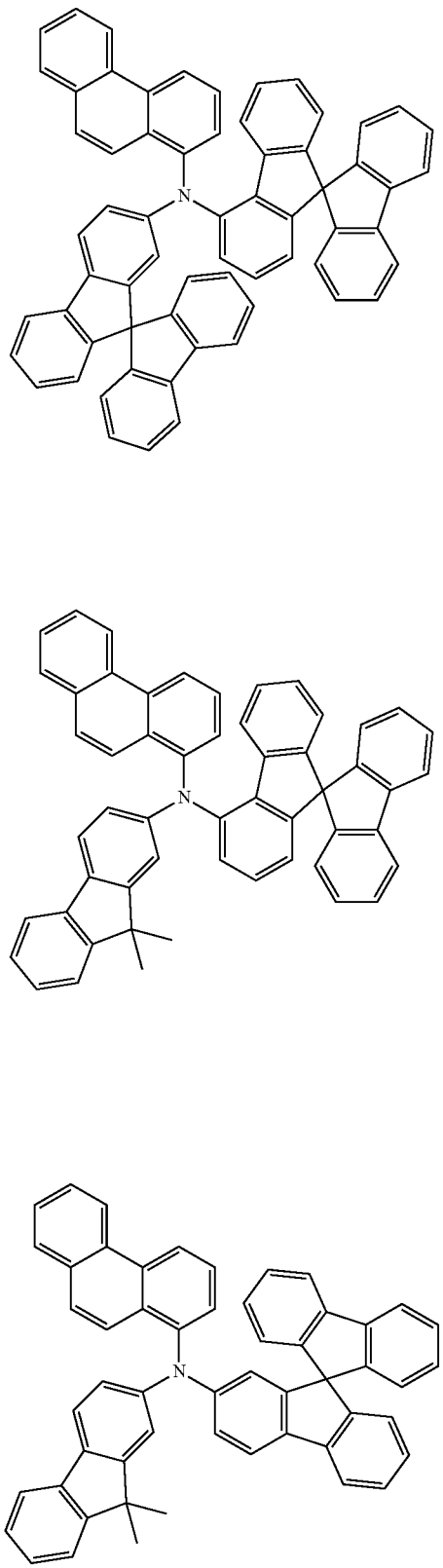
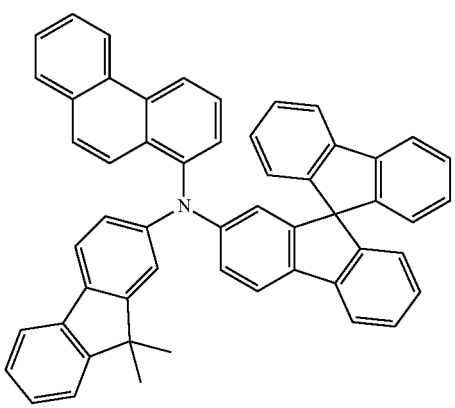

51
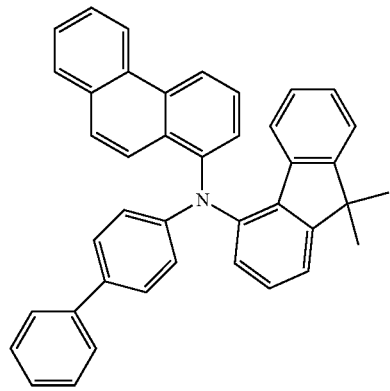
52
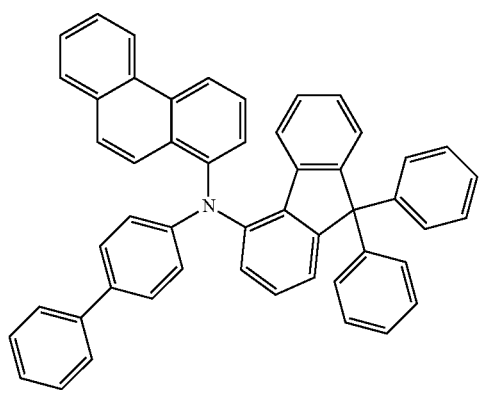
53
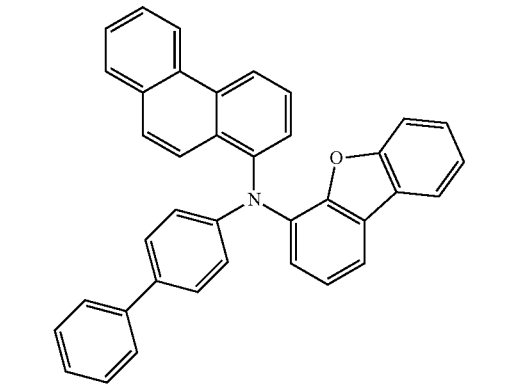
54
55
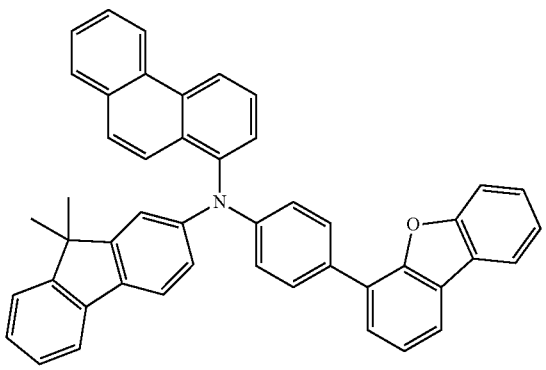
56
57
58
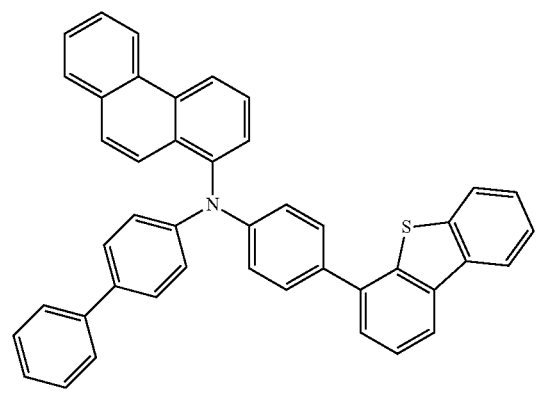

59
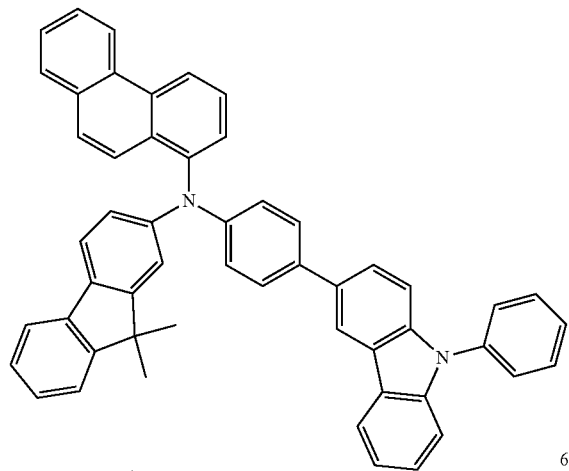
60
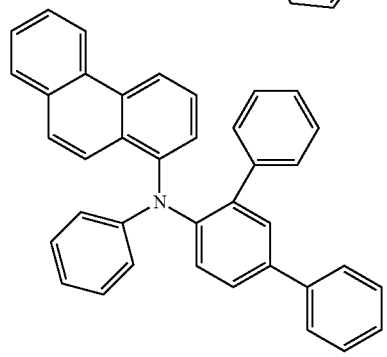
61
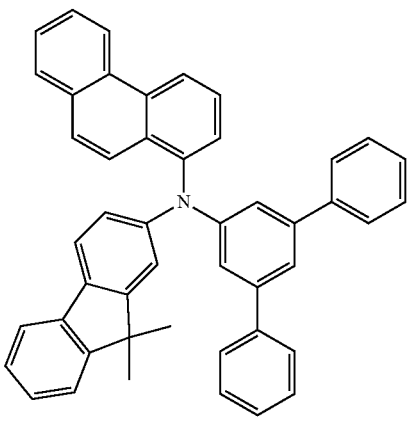
62
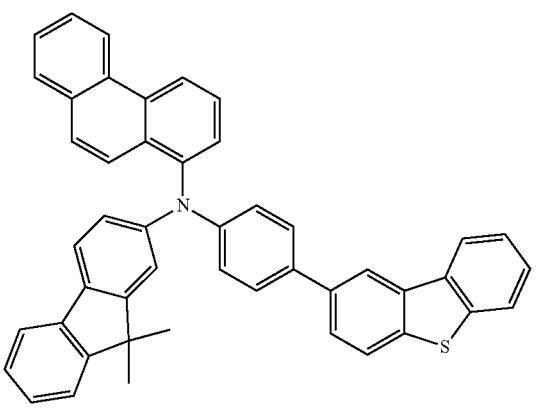
63
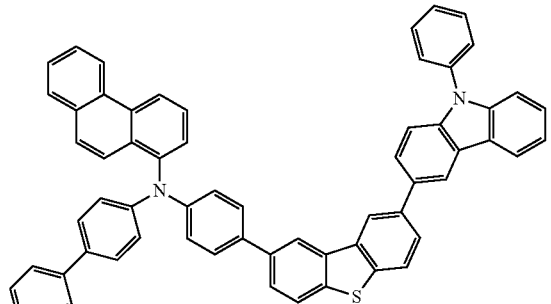
64
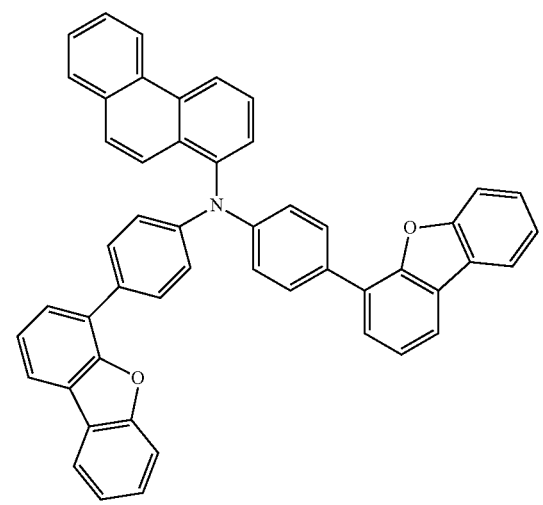
65
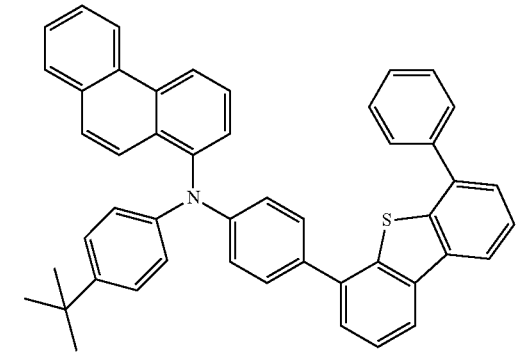
66
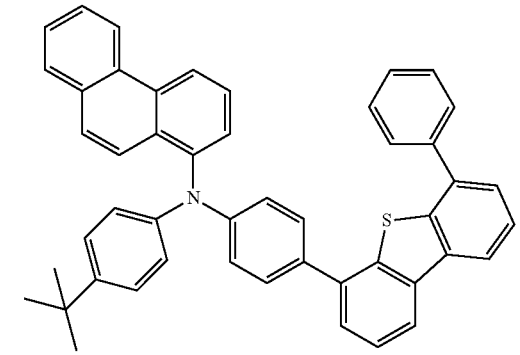

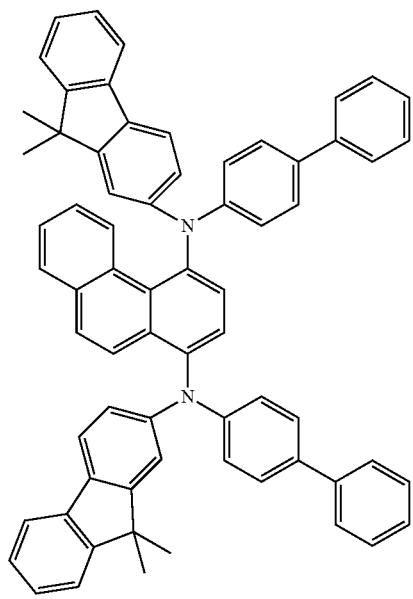
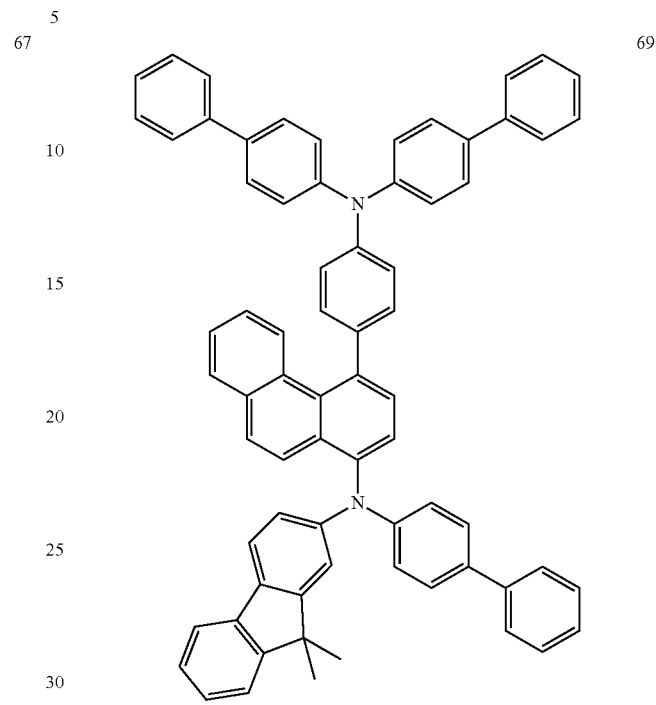
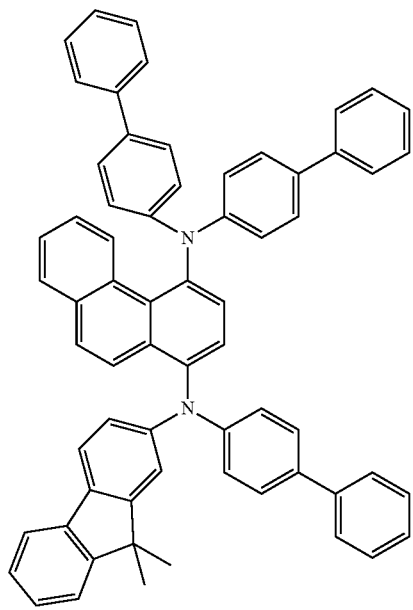
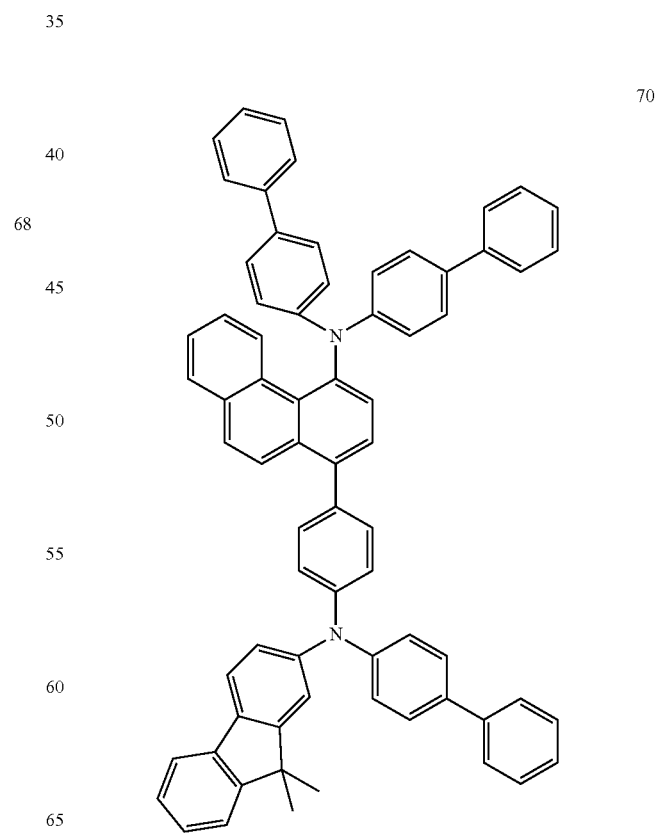

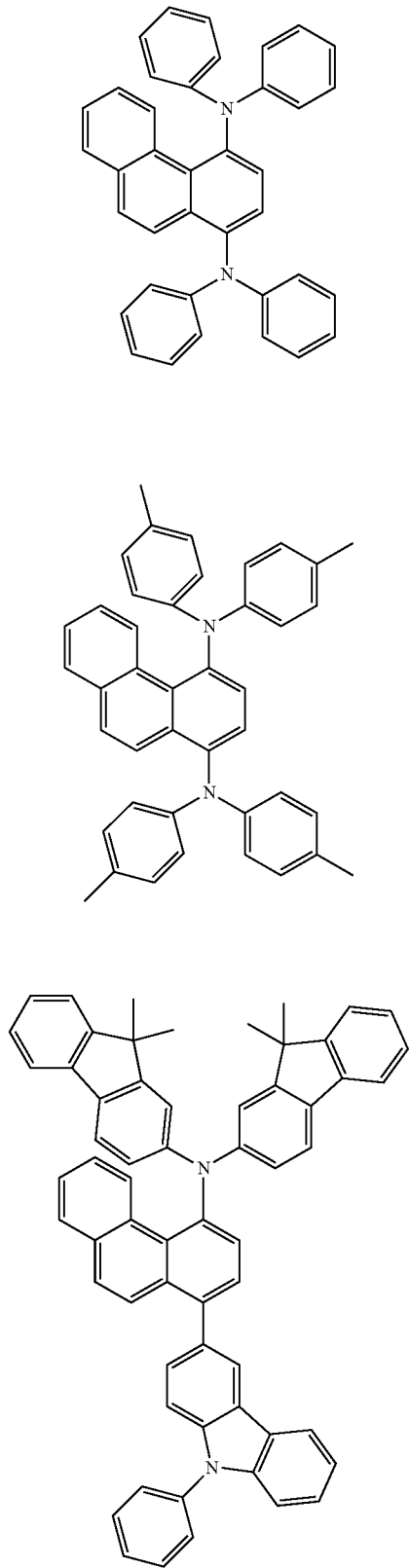
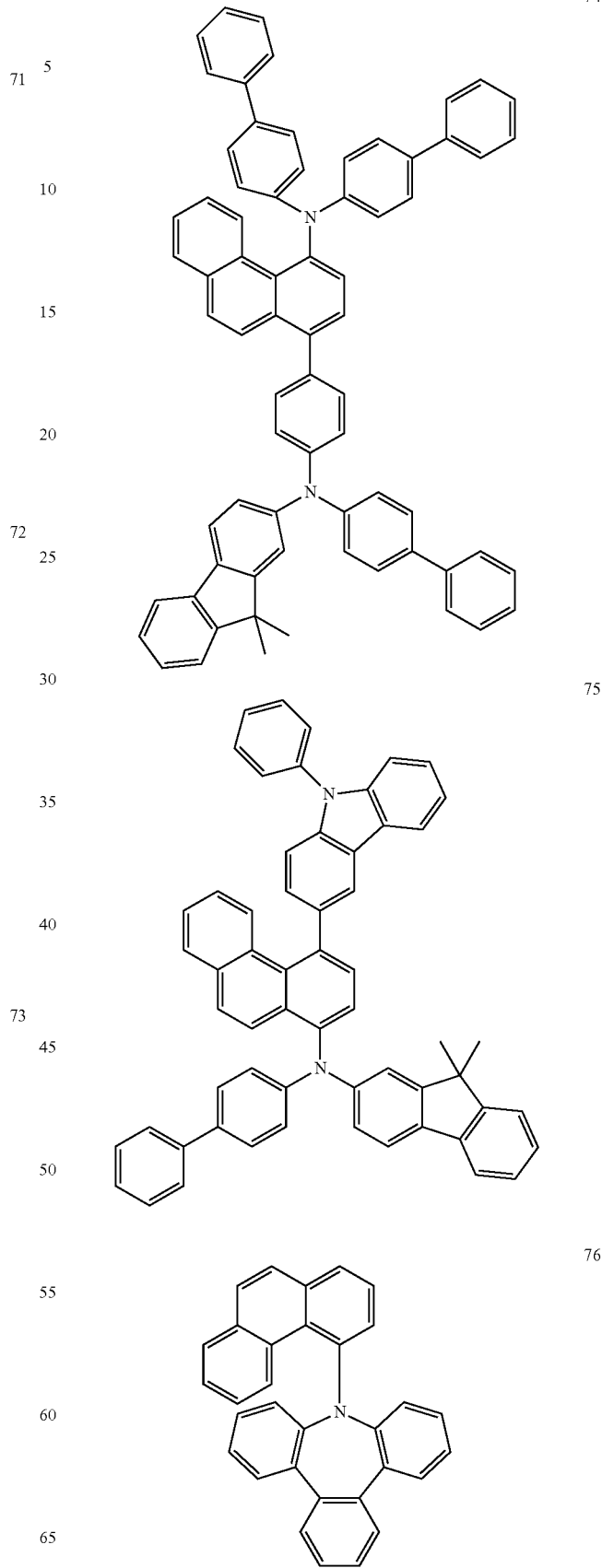

77
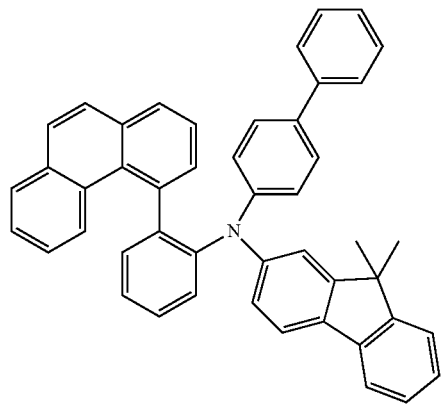
78
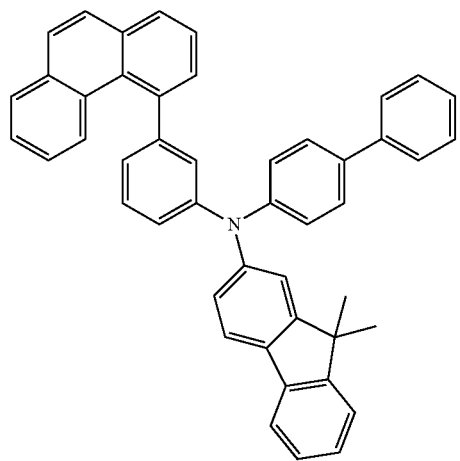
79
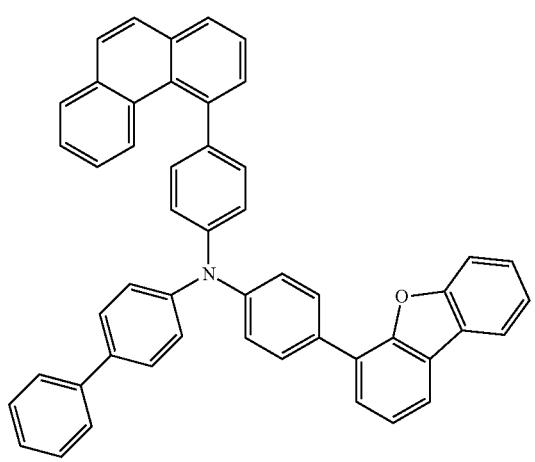
80
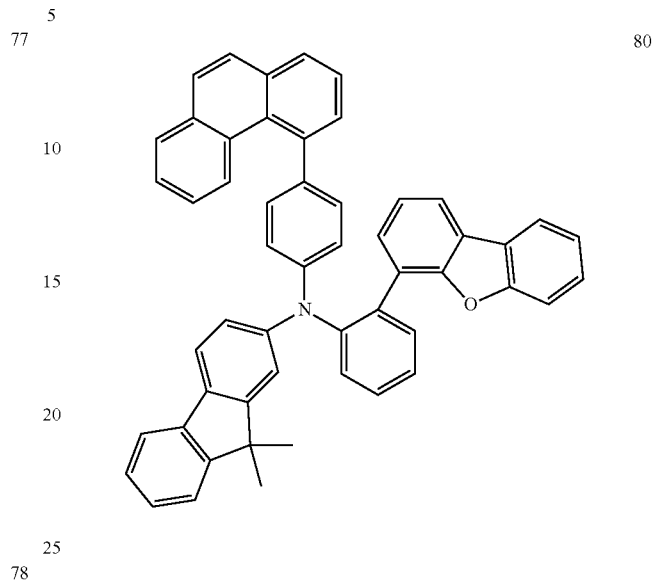
81
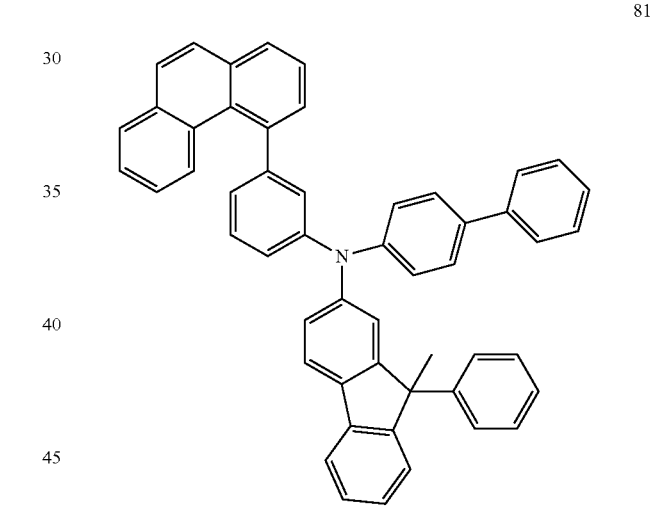
82
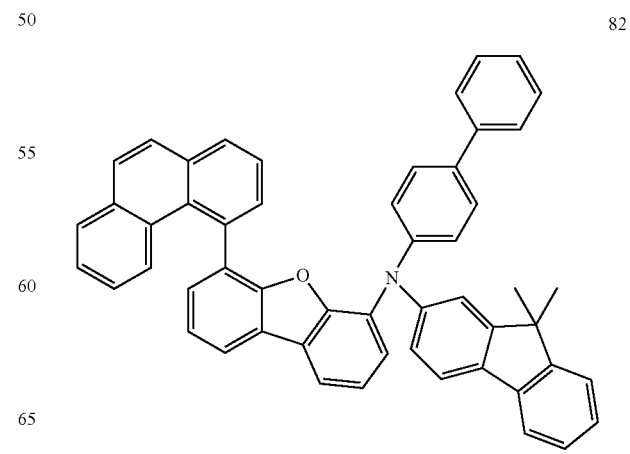

51 -continued

83

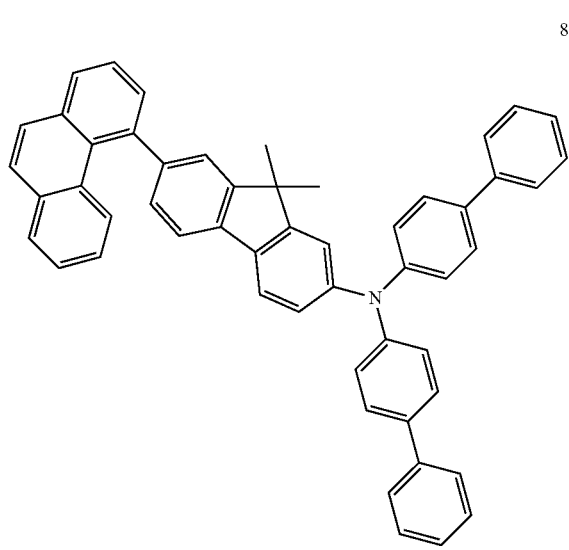

84

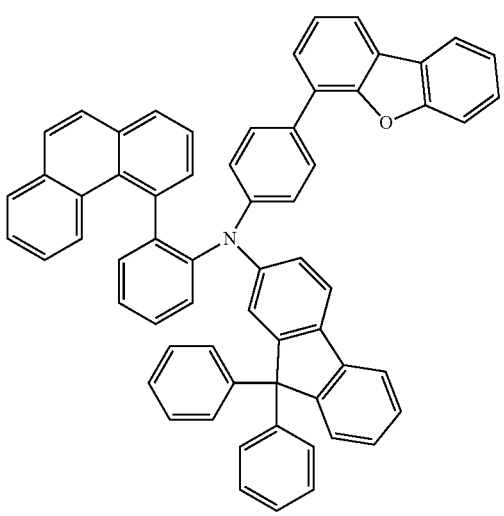

The synthesis of the compounds of the invention can be conducted by the methods and reaction types known in the prior art, for example halogenation, Buchwald coupling, Ullmann coupling and Suzuki coupling.

Scheme 1 shows a preferred synthesis route for preparation of the compounds of the invention. For this purpose, the phenanthrene compound A is reacted in a Buchwald coupling with an amine B of the formula Ar—NH—Ar, or it is reacted in a Suzuki coupling with a boronic acid derivative C of the formula Ar₂N—Ar—B(OR)₃.

Scheme 1

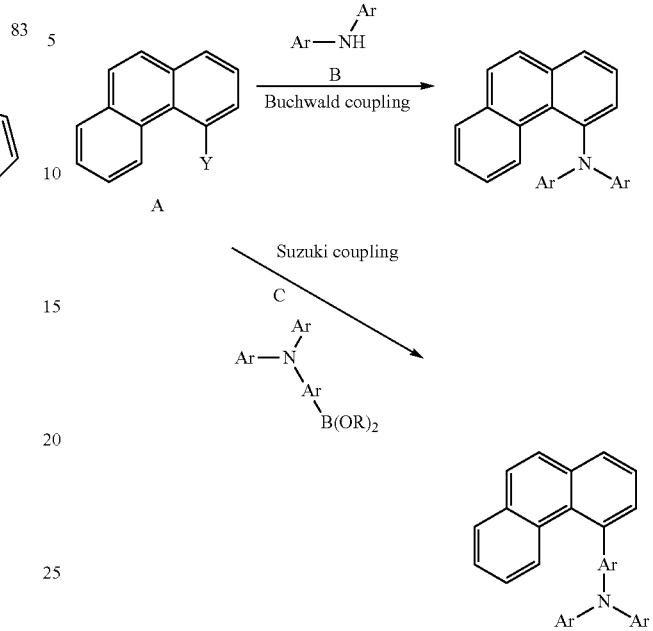

Y = leaving group, for example halogen, triflate
Ar = aromatic or heteroaromatic ring system
R = organic radical By an analogous route (scheme 2), it is possible to prepare compounds of the invention that are substituted in the 1 position of the phenanthrene by an arylamino group or that are substituted in this position by an aryl group bearing an arylamino group. For this purpose, the starting material is a phenanthrene derivative D substituted by a leaving group in the 1 position.

Scheme 2

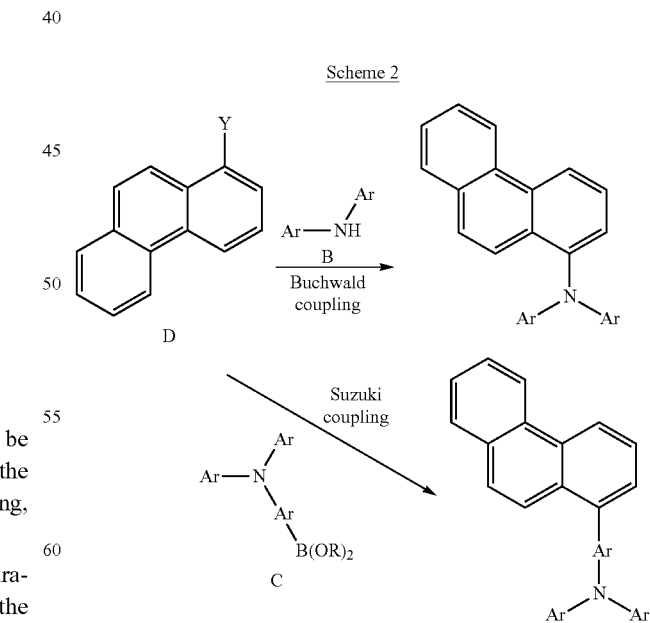

Y = leaving group, for example halogen, triflate
Ar = aromatic or heteroaromatic ring system
R = organic radical Synthesis routes for the starting compounds A and D which are used in the synthesis of the compounds of the invention are known to those skilled in the art. In addition, in the working examples, some explicit synthesis methods are illustrated in detail.

As shown in the working examples, it is possible by use of two leaving groups, one in the 1 position and one in the 4 position of the phenanthrene, to prepare compounds of the formula (I) having two arylamino groups. By use of two different leaving groups, it is possible, as likewise shown in the working examples, to prepare compounds of the formula (I) having two different arylamino groups in the 1 and 4 positions.

The invention thus further provides a process for preparing a compound of the formula (I), characterized in that a phenanthrene compound substituted by a leaving group in the 1 and/or 4 position is reacted in a coupling reaction with a diarylamino compound or with a triarylamino compound substituted by a leaving group.

The leaving groups are preferably selected from halide, preferably Br or I, boronic acid groups, boronic ester groups and sulfonic ester groups, preferably trifluorosulfonic ester groups. Boronic acid groups and boronic ester groups are particularly preferred in the reaction of phenanthrene compound with triarylamino compound.

The coupling reaction in the reaction of the phenanthrene compound with a diarylamino compound is preferably selected from Buchwald coupling reactions. The coupling reaction in the reaction of the phenanthrene compound with a triarylamino compound is preferably selected from Suzuki reactions.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$, $R^4$, $R^5$, $R^6$ or $R^7$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers, oligomers and dendrimers of the invention have advantageous properties, especially high lifetimes, high efficiencies and good color coordinates.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to C—C and C—N bonds are as follows:

(A) SUZUKI polymerization;
(B) YAMAMOTO polymerization;
(C) STILLE polymerization; and
(D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) or at least one polymer, oligomer or dendrimer containing at least one unit of formula (I) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

It is more preferably an organic electroluminescent device (OLED) comprising anode, cathode and at least one emitting layer, characterized in that at least one organic layer, which may be an emitting layer, a hole transport layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably as follows: anode-hole injection layer-hole transport layer-optionally further hole transport layer-optionally electron blocker layer-emitting layer-electron transport layer-electron injection layer-cathode.

However, it is not necessary for all the layers mentioned to be present, and further layers may additionally be present.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue or yellow or orange or red light are used in the emitting layers. Especially preferred are three-layer systems, i.e. systems having three emitting layers, where the three layers show blue, green and orange or red emission (for the basic construction see, for example, WO 2005/011013). The compounds of the invention are preferably present in the hole transport layer, hole injection layer or electron blocker layer.

It is preferable in accordance with the invention when the compound of formula (I) is used in an electronic device comprising one or more phosphorescent emitting compounds. In this case, the compound may be present in different layers, preferably in a hole transport layer, an electron blocker layer, a hole injection layer or in an emitting layer.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in a table which follows.

It is also possible in accordance with the invention to use the compound of formula (I) in an electronic device comprising one or more fluorescent emitting compounds.

In a preferred embodiment of the invention, the compounds of formula (I) are used as hole transport material. In that case, the compounds are preferably present in a hole transport layer, an electron blocker layer or a hole injection layer.

A hole transport layer according to the present application is a layer having a hole-transporting function between the anode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side.

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the formula (I) then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

Particularly preferred p-dopants are quinodimethane compounds, azaindenofluorenediones, azaphenalenes, azatriphenylenes, I$_2$, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably Re$_2$O$_7$, MoO$_3$, WO$_3$ and ReO$_3$.

The p-dopants are preferably in substantially homogeneous distribution in the p-doped layers. This can be achieved, for example, by coevaporation of the p-dopant and the hole transport material matrix.

Preferred p-dopants are especially the following compounds:

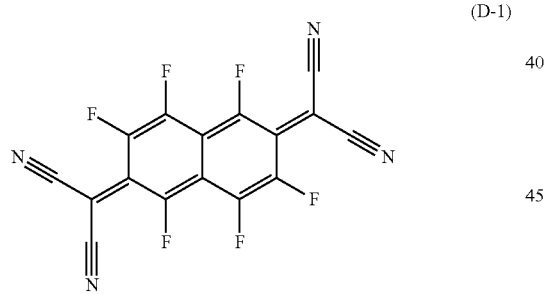
(D-1)

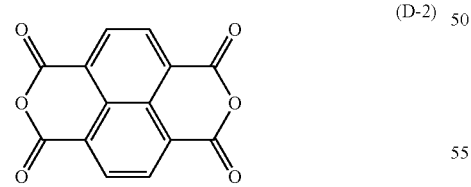
(D-2)

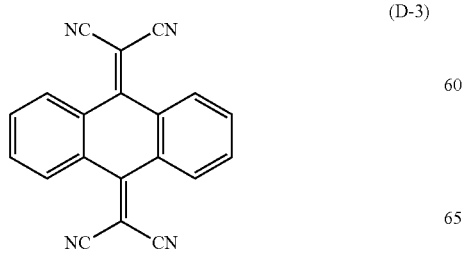
(D-3)

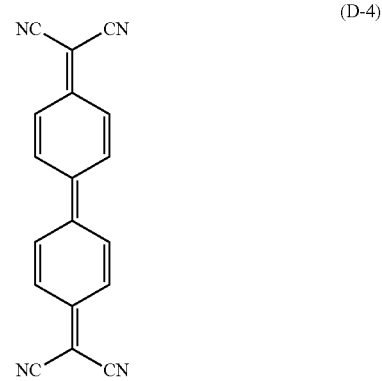
(D-4)

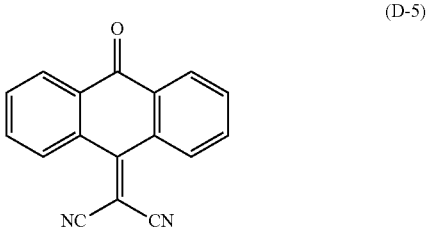
(D-5)

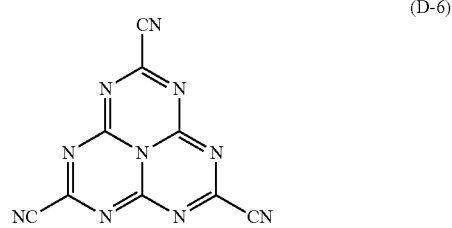
(D-6)

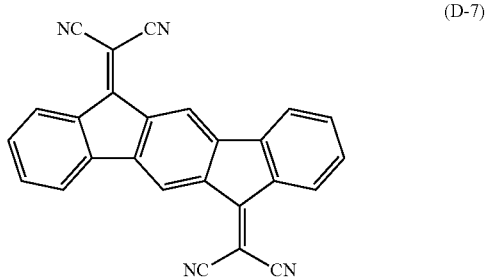
(D-7)

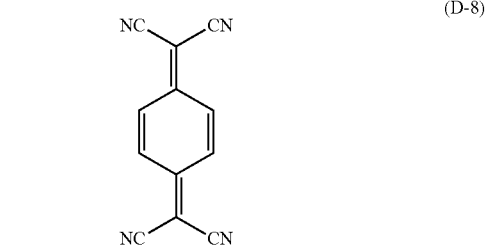
(D-8)

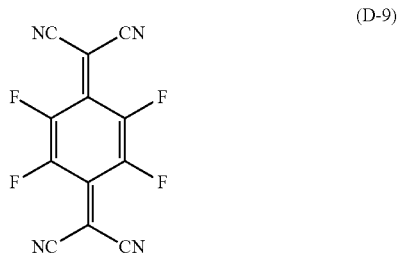
(D-9)

-continued

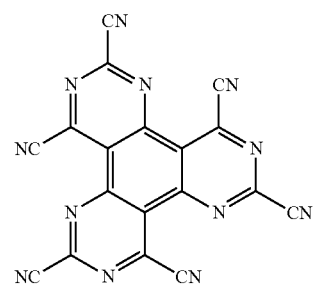
(D-10)

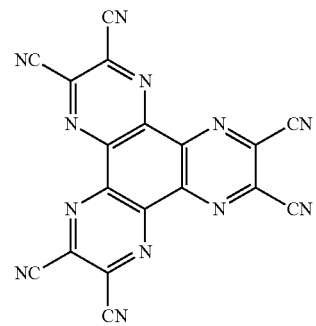
(D-11)

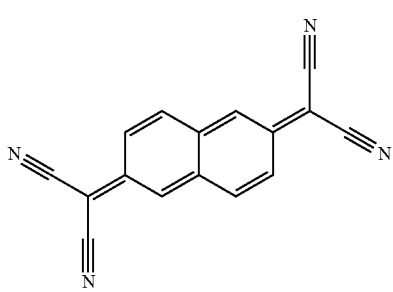
(D-12)

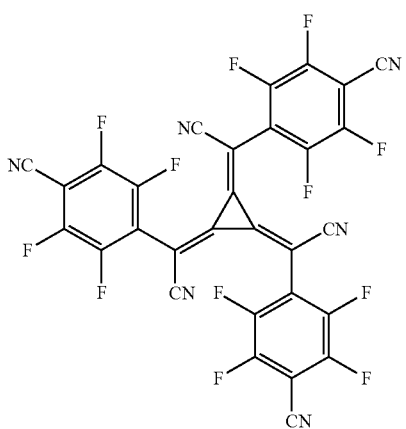
(D-13)

In a further preferred embodiment of the invention, the compound of formula (I) is used as hole transport material in combination with a hexaazatriphenylene derivative as described in US 2007/0092755. Particular preference is given here to using the hexaazatriphenylene derivative in a separate layer.

In a further embodiment of the present invention, the compound of the formula (I) is used as matrix material in combination with one or more emitting compounds, preferably phosphorescent emitting compounds.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the emitting compound is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the compounds of the invention as matrix components of a mixed matrix system are selected from the preferred matrix materials specified below for phosphorescent emitting compounds or the preferred matrix materials for fluorescent emitting compounds, according to what type of emitting compound is used in the mixed matrix system.

Preferred phosphorescent emitting compounds for use in mixed matrix systems are listed in a table which follows.

In a further embodiment of the present invention, the compound of the formula (I) is used as emitting compound in an emitting layer of an OLED. In this case, it is preferably a fluorescent emitting compound, more preferably a blue-fluorescing emitting compound.

When the compound of the formula (I) is used as emitting compound in an emitting layer of an OLED, it is preferably used in combination with one or more matrix materials, more preferably with the abovementioned preferred proportions of emitting compound and matrix material. Preferred matrix materials in this case are the compounds typically used by the person skilled in the art as matrix materials for fluorescent emitting compounds. Examples of preferred compound classes are listed in the sections which follow.

Preferred embodiments of the different functional materials in the electronic device are listed hereinafter.

Preferred phosphorescent emitting compounds are the abovementioned compounds and the compounds shown in the following table:

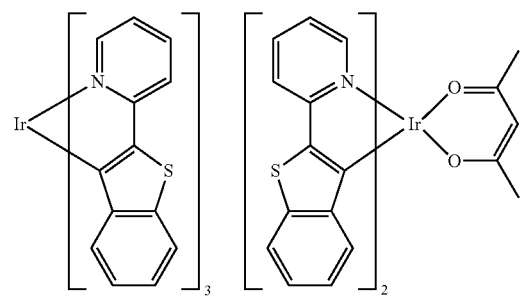

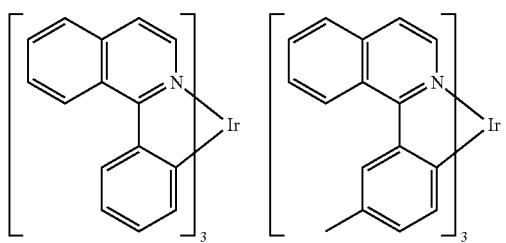

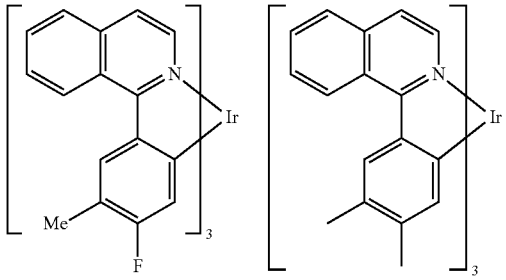

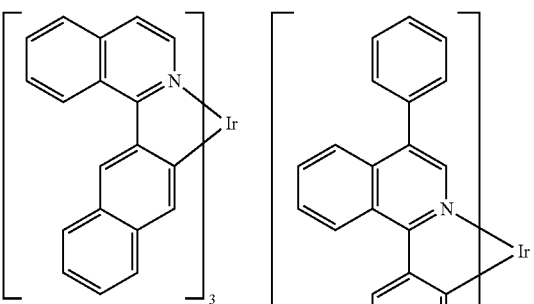

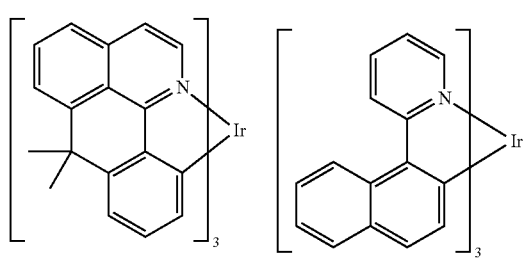

-continued

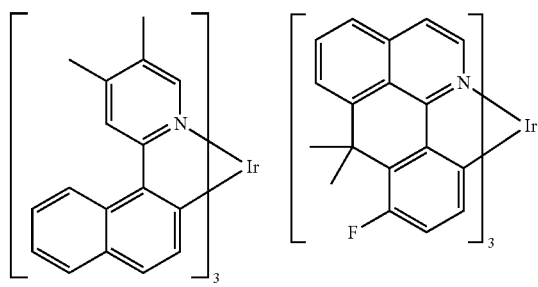

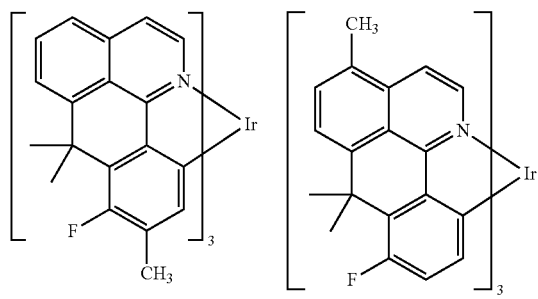

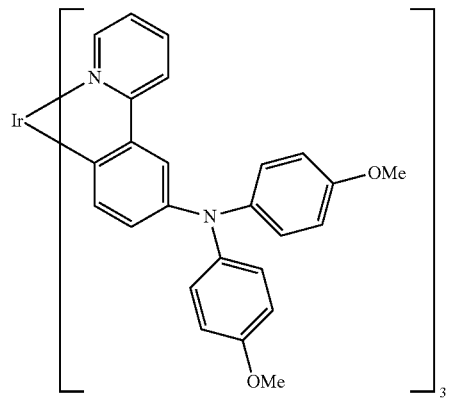

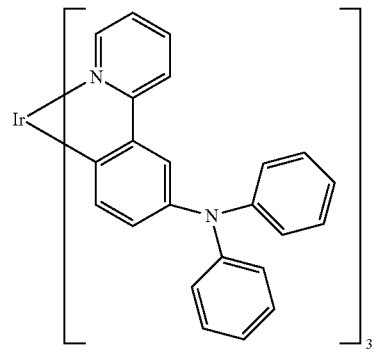

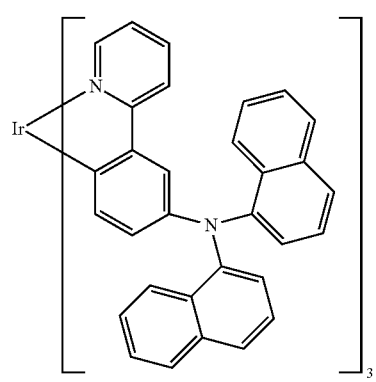

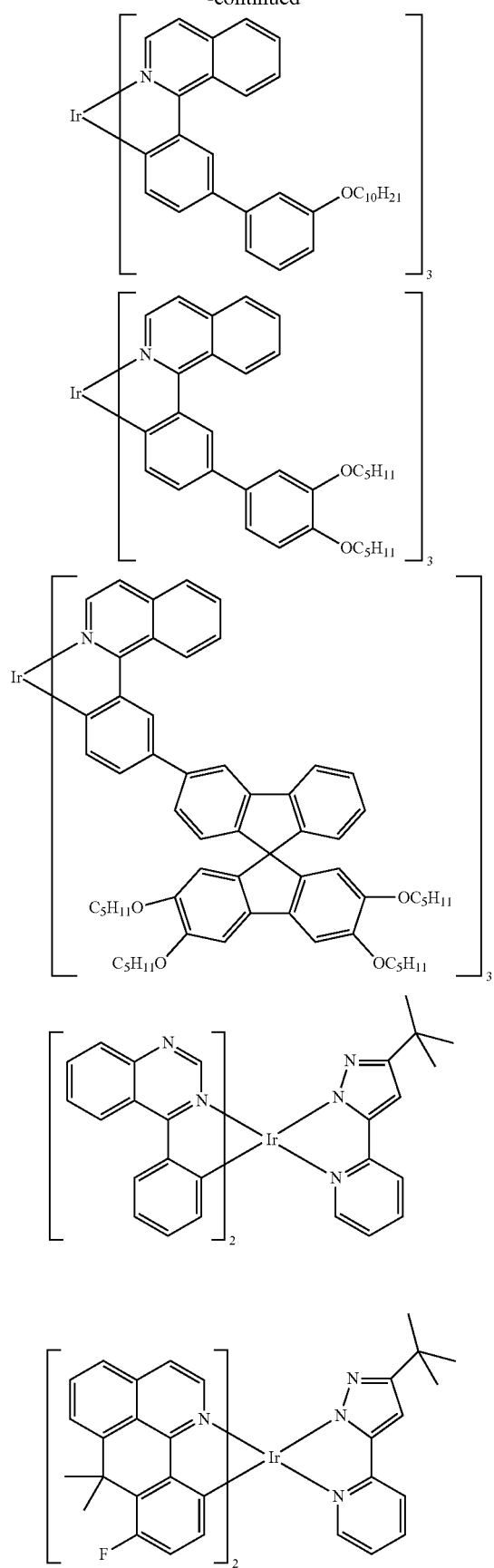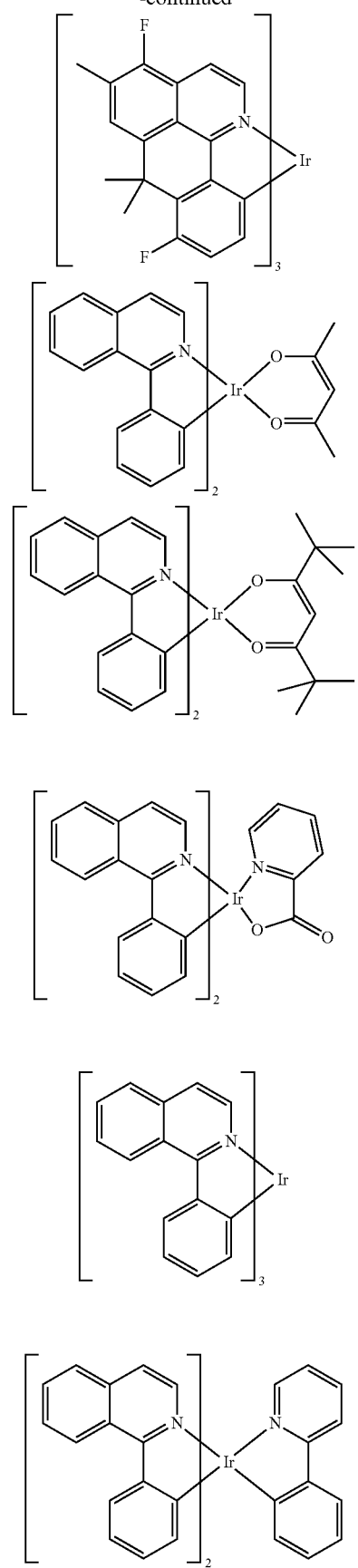

-continued
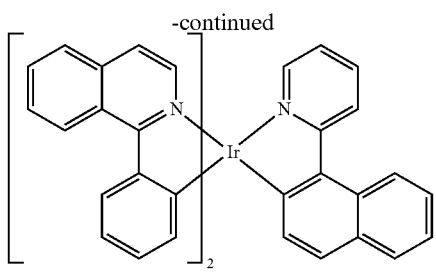
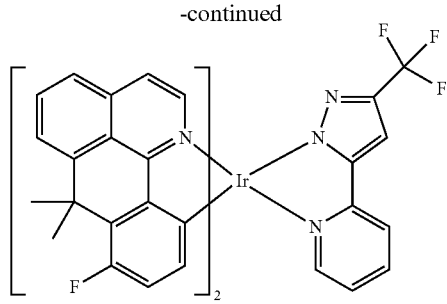
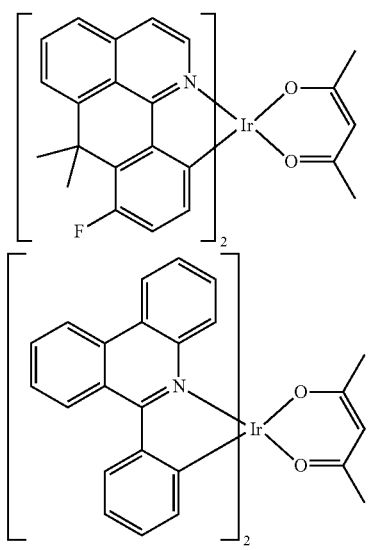
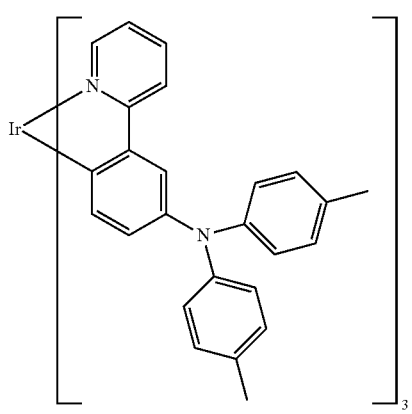
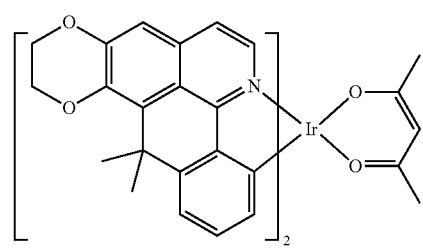
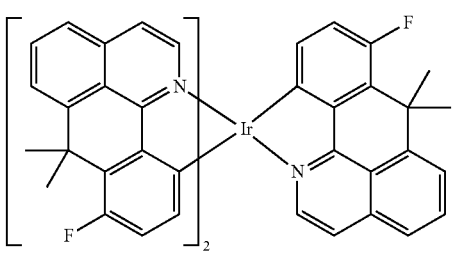
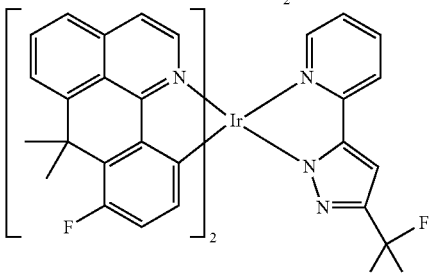
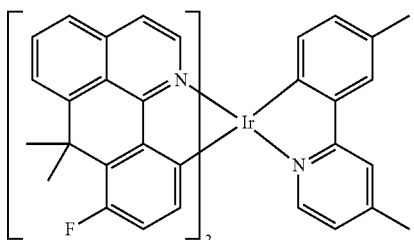
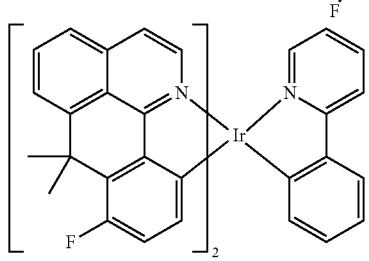
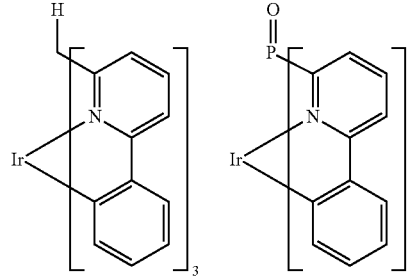

-continued
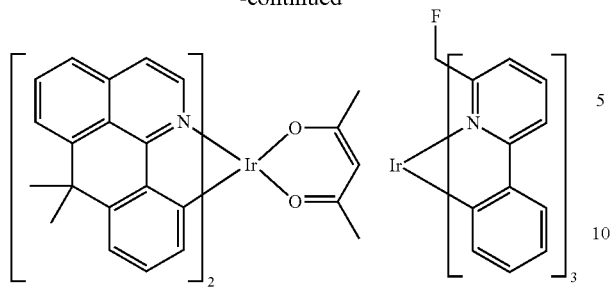
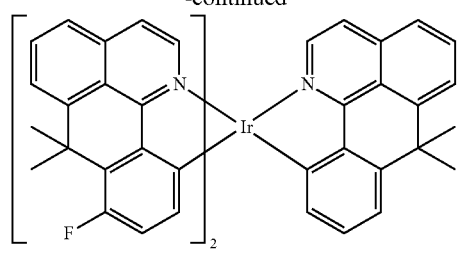
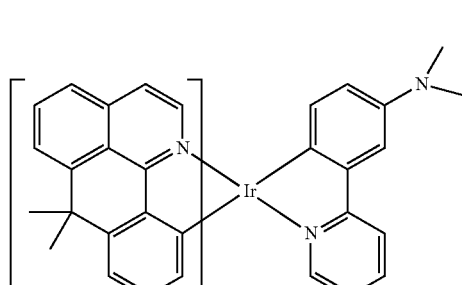
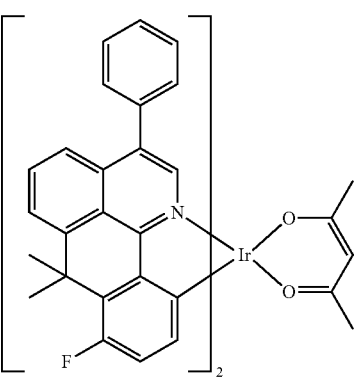
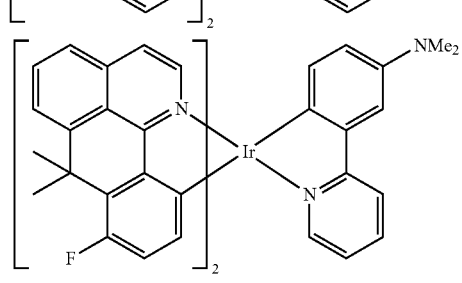
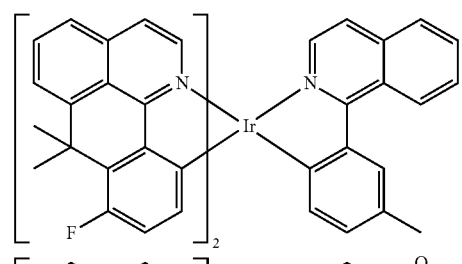
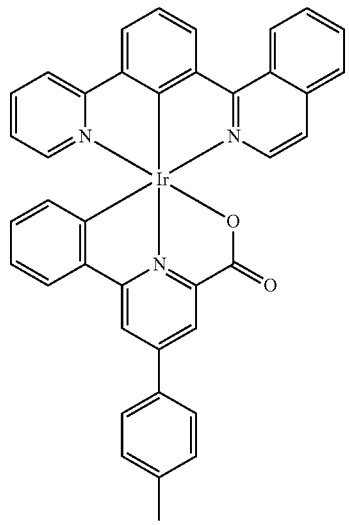
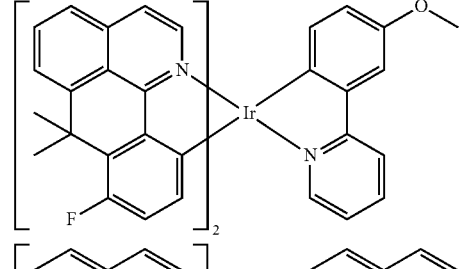
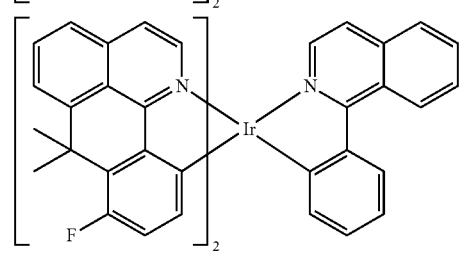
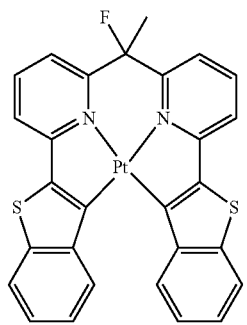

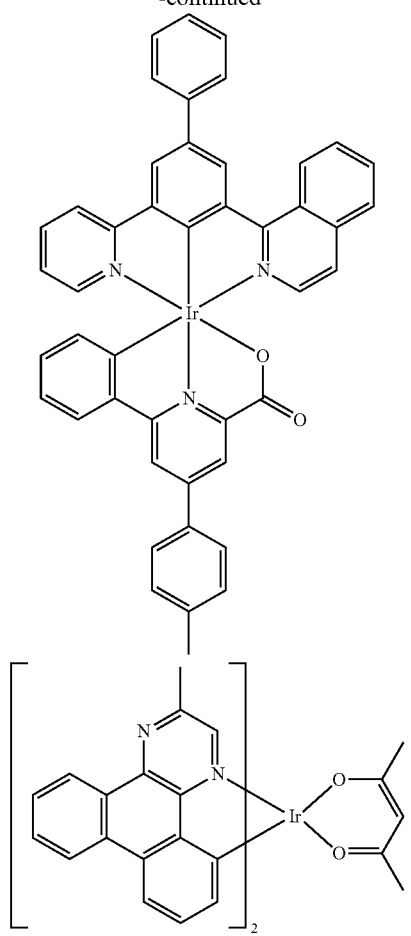
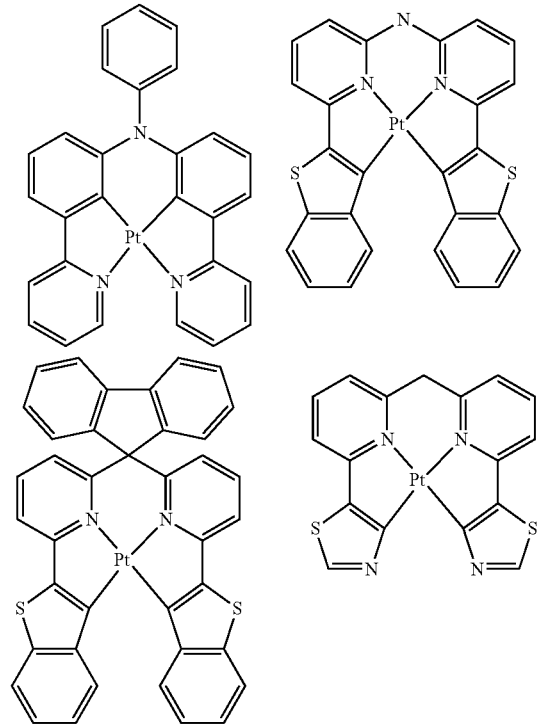
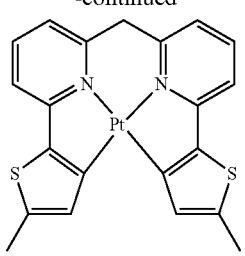
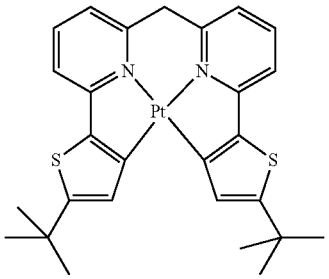
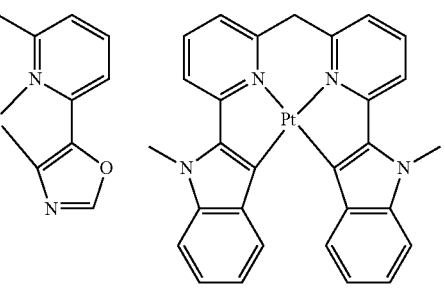
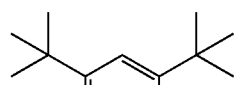
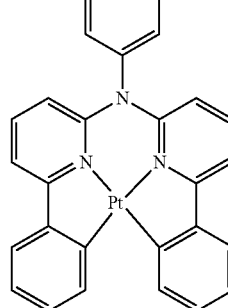
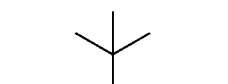
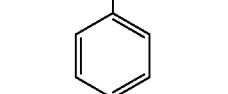
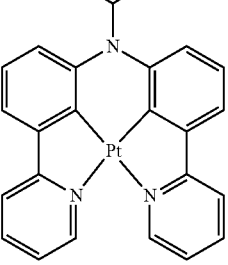

71
-continued
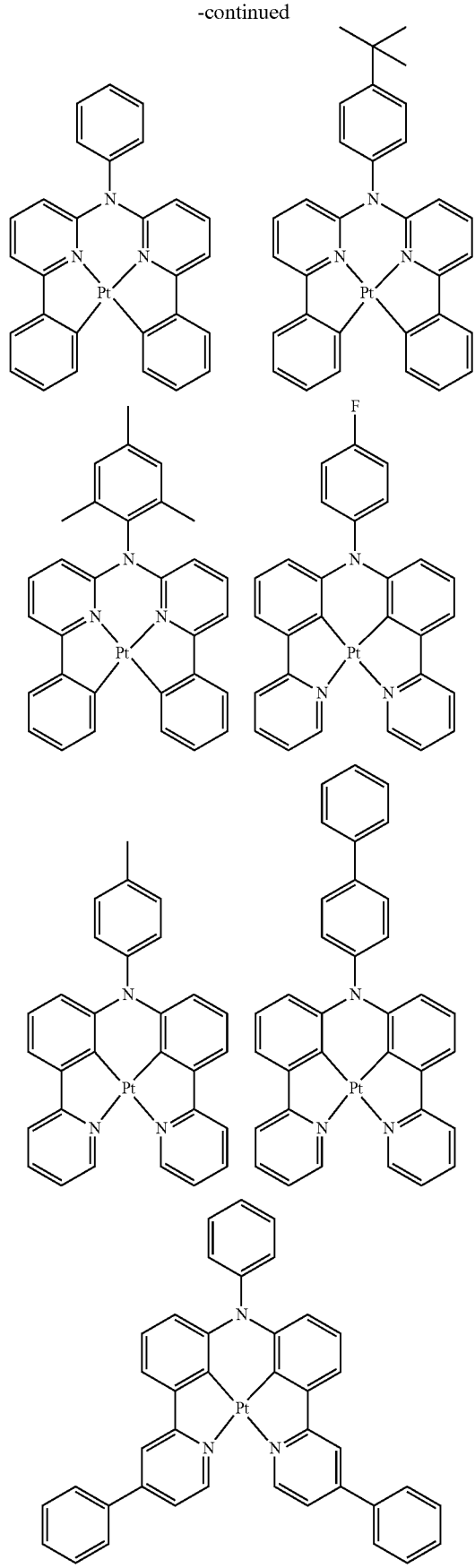
72
-continued
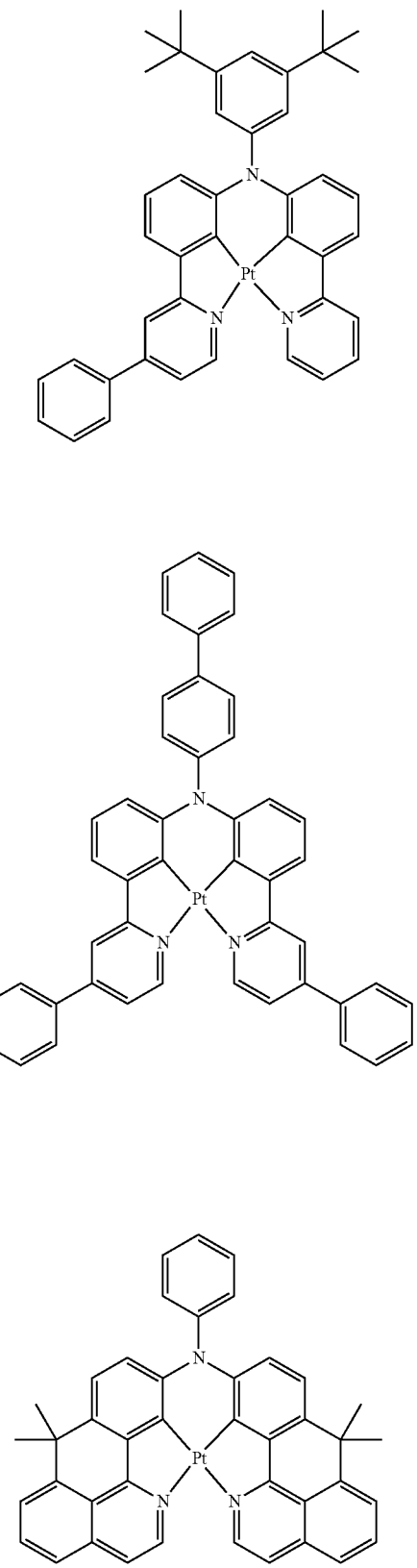

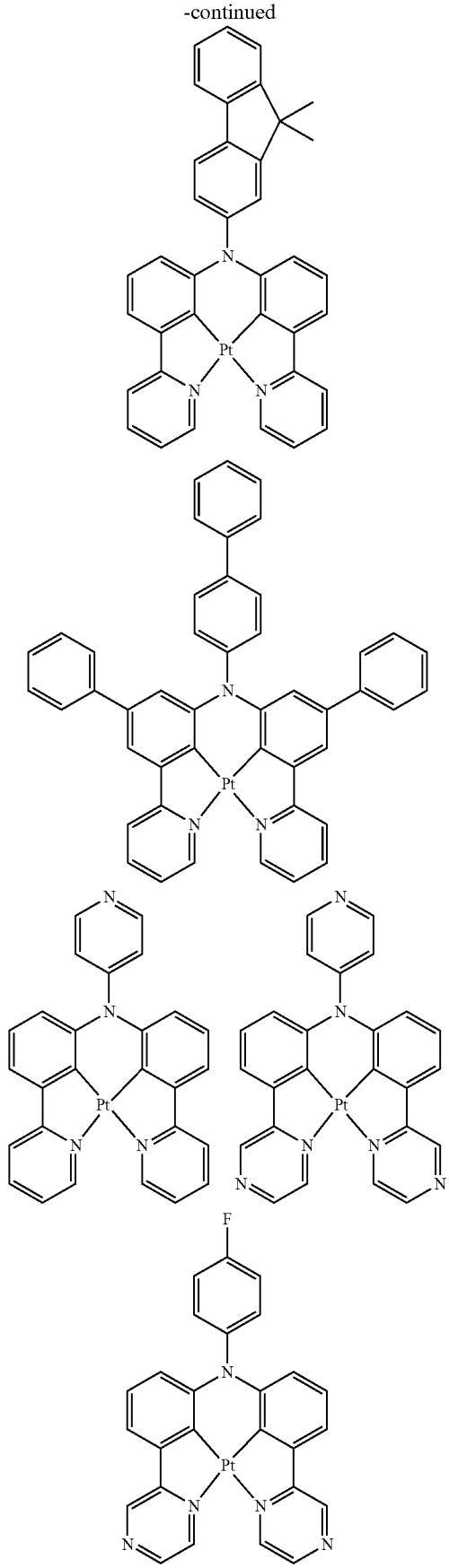

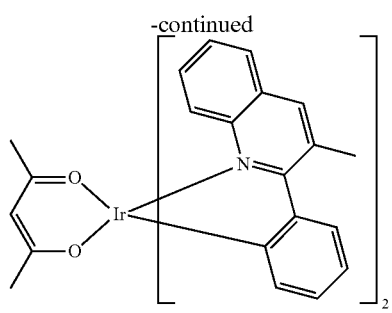
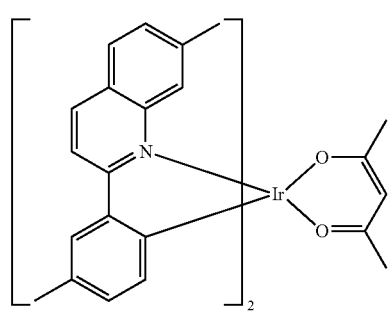
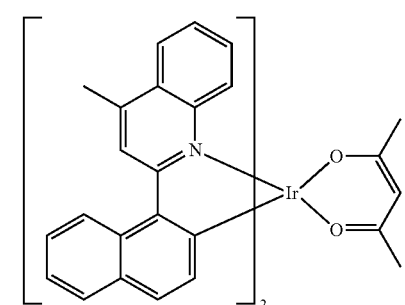
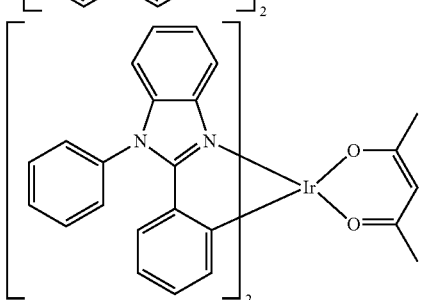
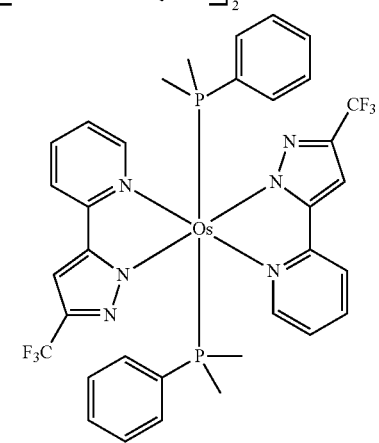
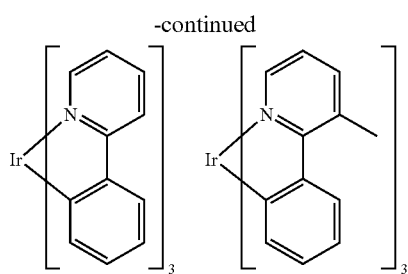
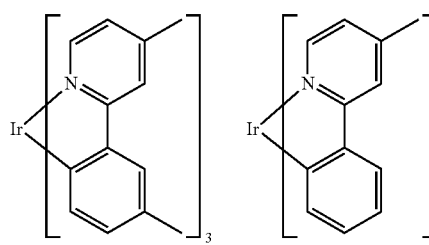
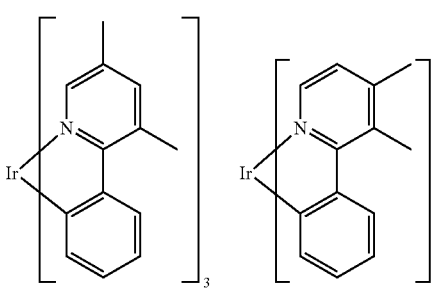
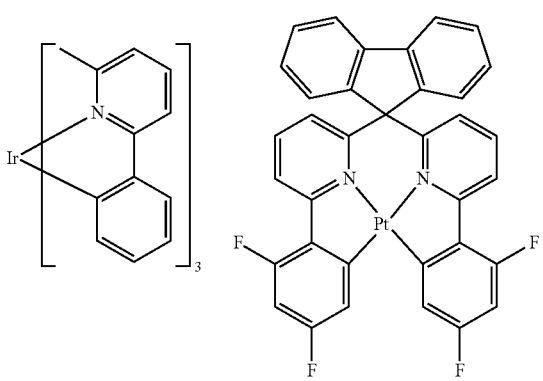
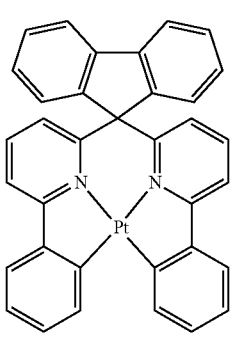

77
-continued
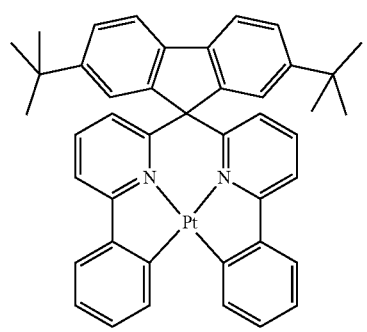
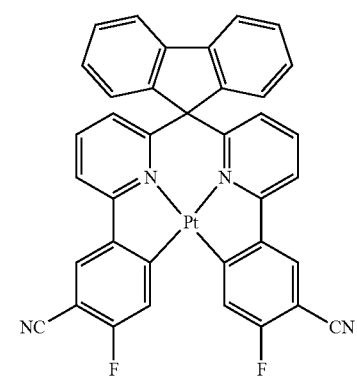
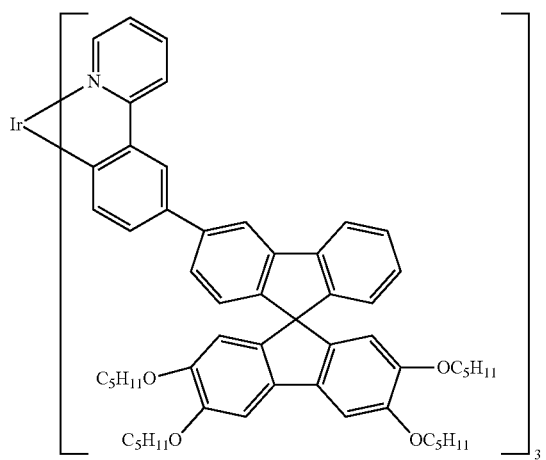
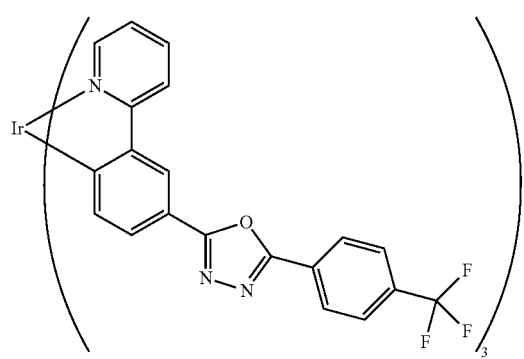
78
-continued
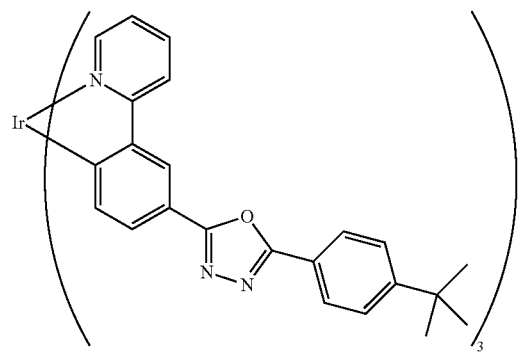
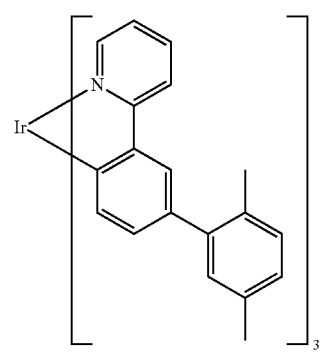
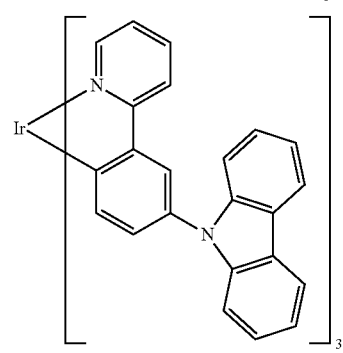
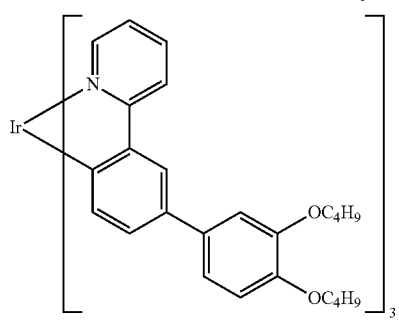
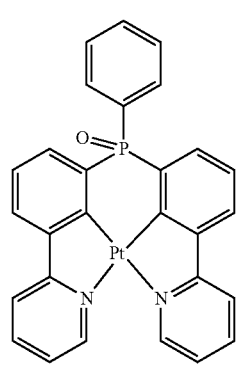

79
-continued
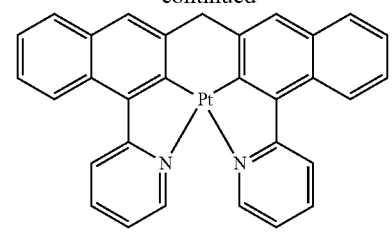
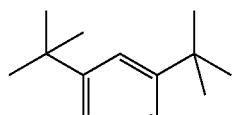
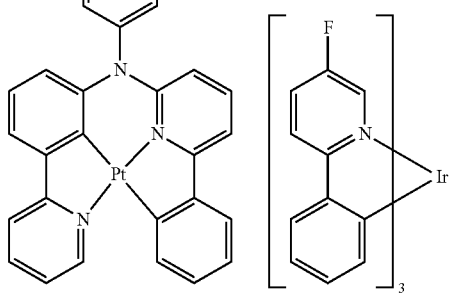
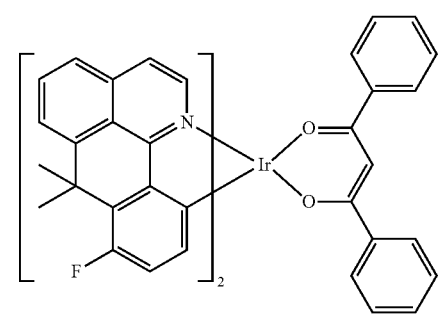
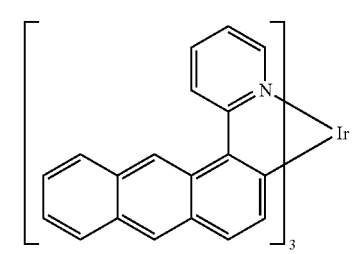
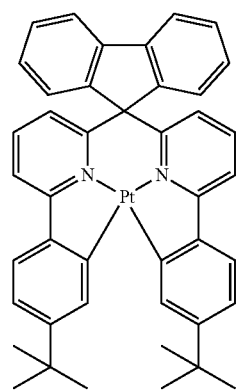
80
-continued
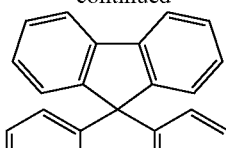
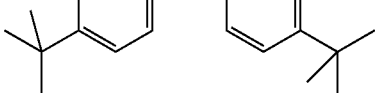
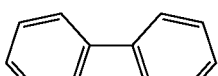
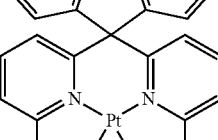
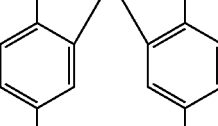
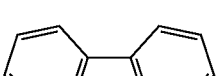
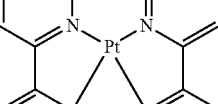
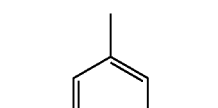
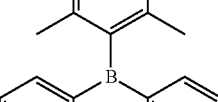
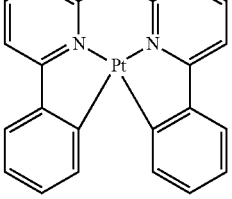
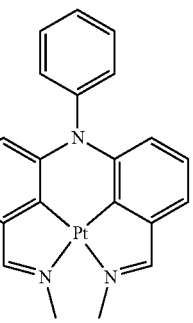

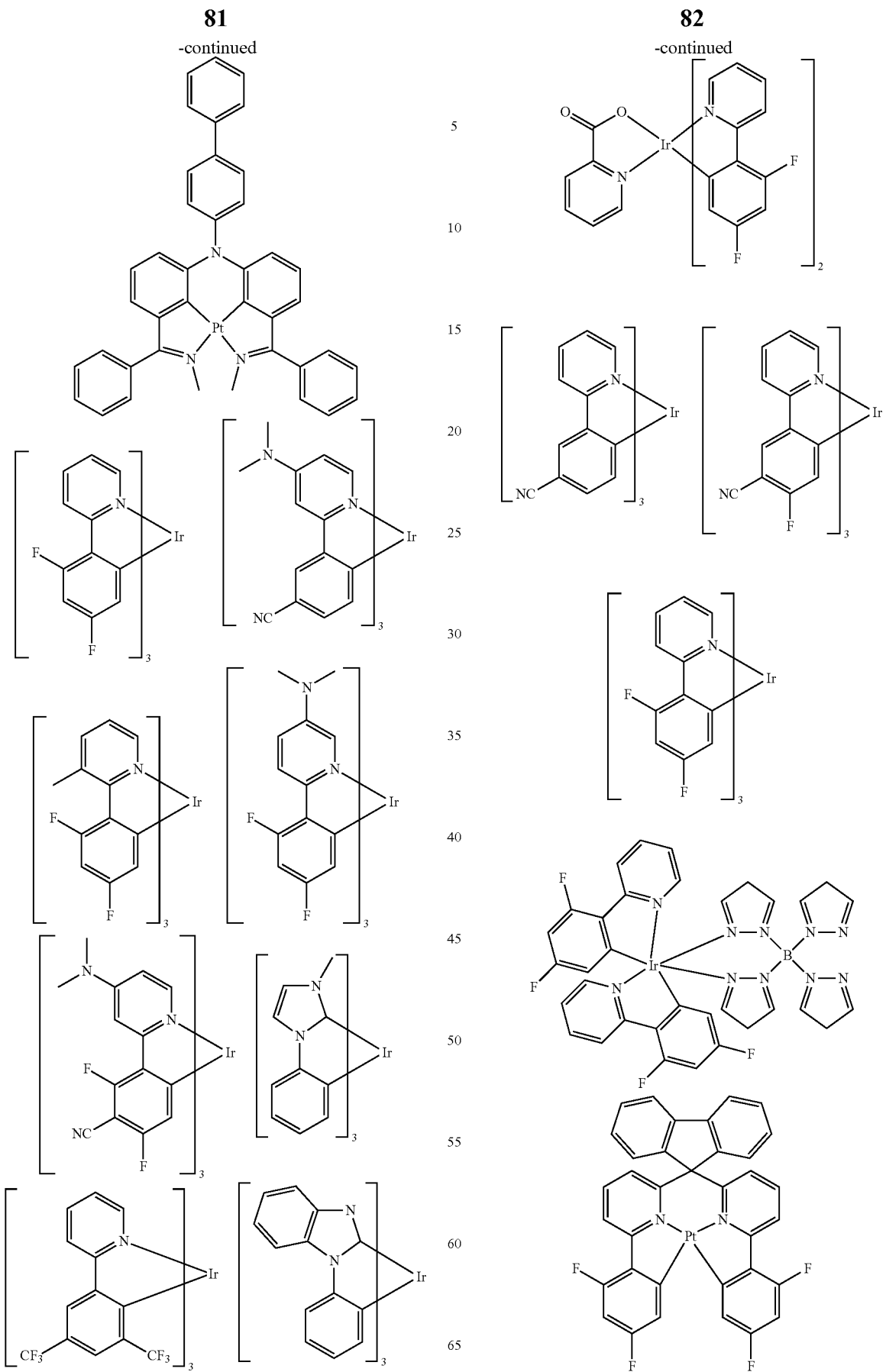

83
-continued
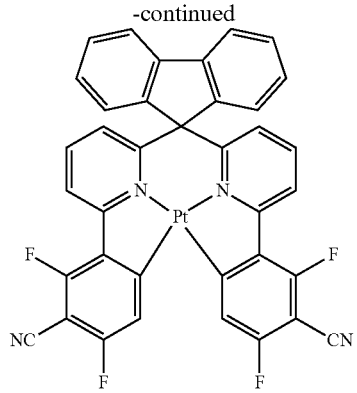
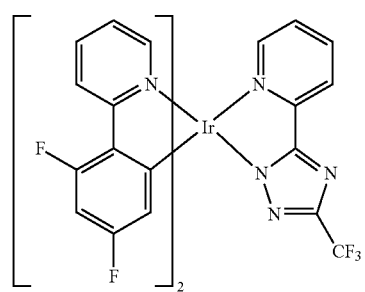
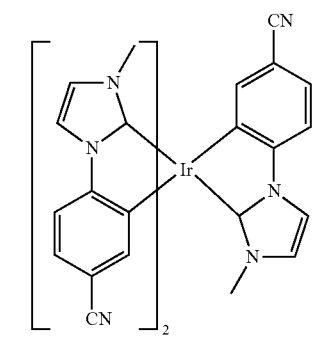
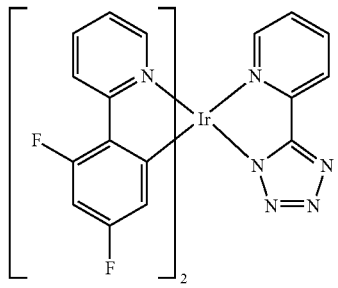
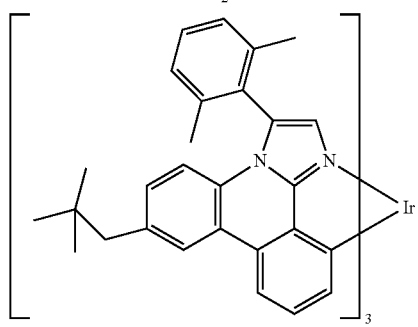
84
-continued
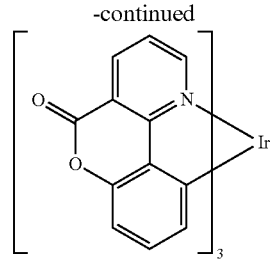
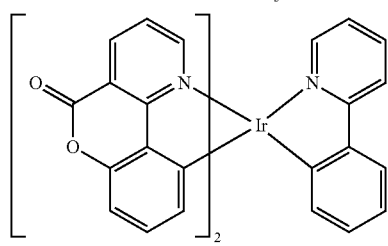
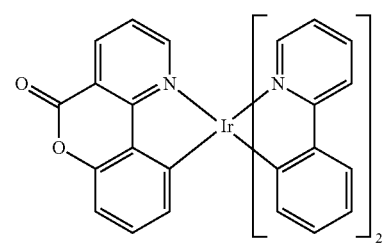
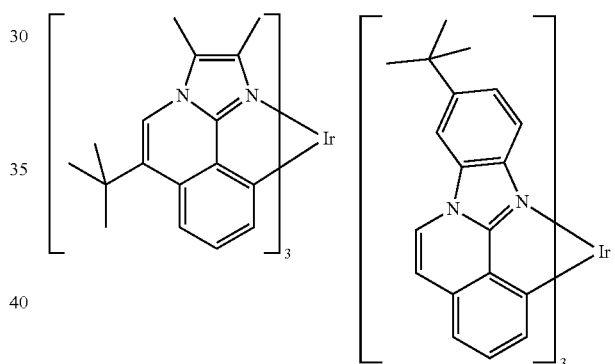
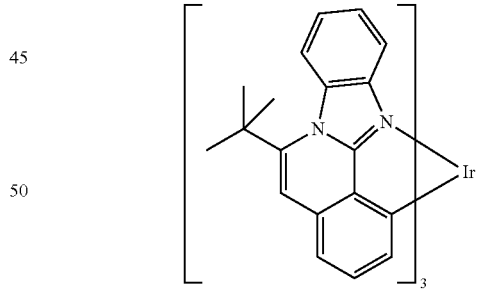
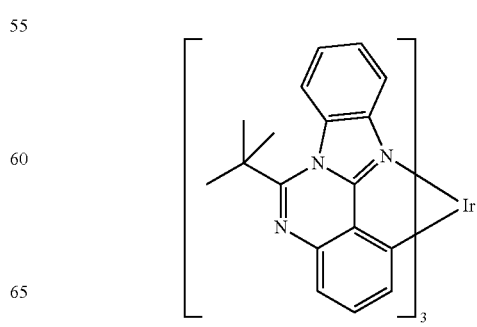

-continued

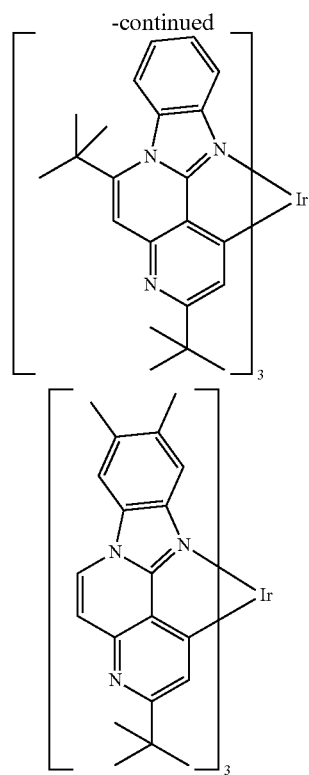

Preferred fluorescent emitting compounds are, aside from the compounds of the formula (I), selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluorenamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522 and the extended benzoindenofluorenes disclosed in WO 2014/111269.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, and the pyrene compounds disclosed in EP 1749809, EP 1905754 and US 2012/0187826.

Preferred matrix materials for phosphorescent emitting compounds are, as well as the compounds of the formula (I), aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art.

Materials used for the electron transport layer may be any materials as used according to the prior art as electron transport materials in the electron transport layer. Especially suitable are aluminum complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

WORKING EXAMPLES

A) Synthesis Examples

A-1) Compounds of the (1) Type

Synthesis of biphenyl-4-yl(9,9-dimethyl-9H-fluoren-2-yl)phenanthren-4-ylamine (1-1)

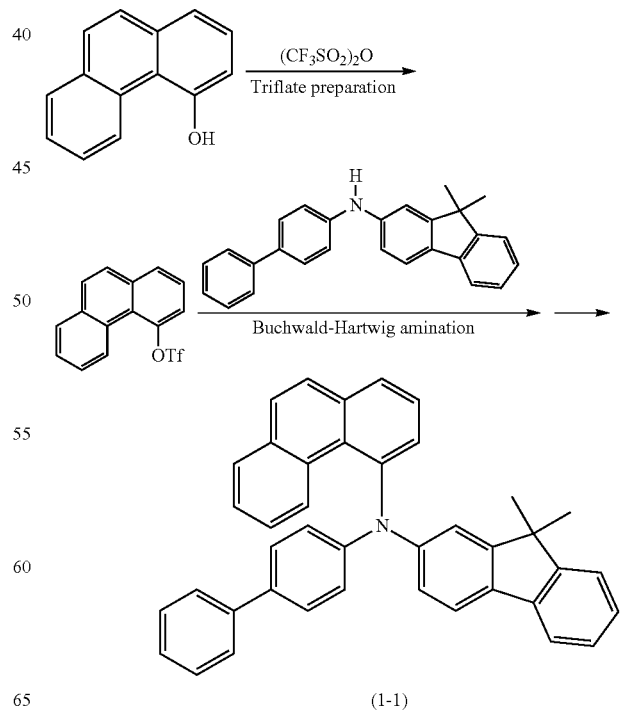

(1-1)

Intermediate: phenanthren-4-yl trifluoromethanesulfonate 20 g (103 mmol) of 4-hydroxyphenanthrene (CAS no.: 7651-86-7, synthesis described in Tetrahedron 2010, 66(12), 2111) and 42.8 mL of pyridine (309 mmol) are dissolved in 130 mL of $CH_2Cl_2$. At 5° C., 21.2 mL (128 mmol) of trifluoromethanesulfonic anhydride are added. The mixture is stirred for a further 5 hours. The mixture is subsequently partitioned between $CH_2Cl_2$ and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 29.4 g (87% of theory).

Biphenyl-4-yl(9,9-dimethyl-9H-fluoren-2-yl) phenanthren-4-ylamine (1-1)

29.4 g of the triflate (90 mmol) and 32.6 g of biphenyl-4-yl(9,9-dimethyl-9H-fluoren-2-yl)amine (90 mmol) are dissolved in 340 mL of toluene. The solution is degassed and saturated with $N_2$. Thereafter, 2.2 g (5.4 mmol) of SPhos and 4.13 g of palladium-dba (4.5 mmol) are added. Subsequently, 17.3 g of sodium tert-butoxide (180 mmol) are added. The reaction mixture is heated to 85° C. under a protective atmosphere for 4 h. The mixture is subsequently partitioned between toluene and water, and the organic phase is washed three times with water, dried over $Na_2SO_4$ and concentrated by rotary evaporation. After the crude product has been filtered through silica gel with toluene, the remaining residue is recrystallized from heptane/toluene and then sublimed under high vacuum. The purity is 99.9%. The yield is 38 g (80% of theory).

Analogously to the above-described synthesis of compound (1-1), the following compounds (1-2) to (1-8) are prepared:

| | Reactant 1 | Reactant 2 | Product | Yield |
|---|---|---|---|---|
| 1-2 | | | | 75% |
| 1-3 | | | | 82% |

-continued

| | Reactant 1 | Reactant 2 | Product | Yield |
|---|---|---|---|---|
| 1-4 | | | | 86% |
| 1-5 | | | | 77% |
| 1-6 | | | | 73% |

| | Reactant 1 | Reactant 2 | Product | Yield |
|---|---|---|---|---|
| 1-7 | | | | 81% |
| 1-8 | | | | 75% |
A-2) Compounds of the (2) Type
Synthesis of biphenyl-4-yl(9,9-dimethyl-9H-fluoren-2-yl)(4-phenanthren-4-ylphenyl)amine (Compound (2-1))
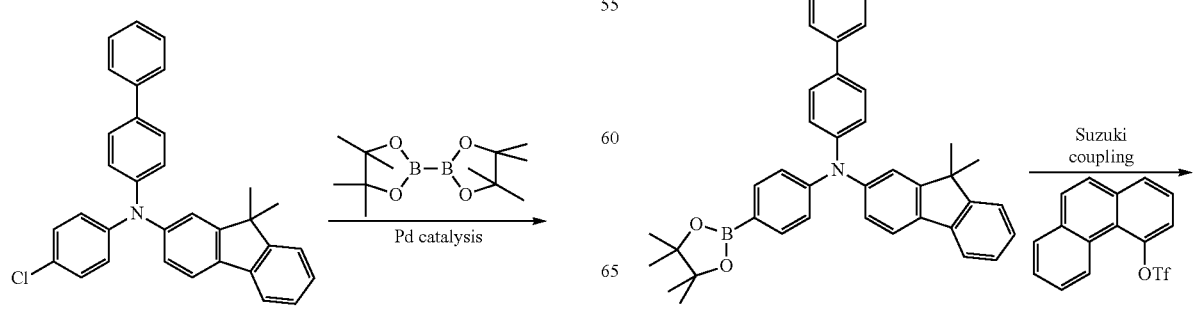

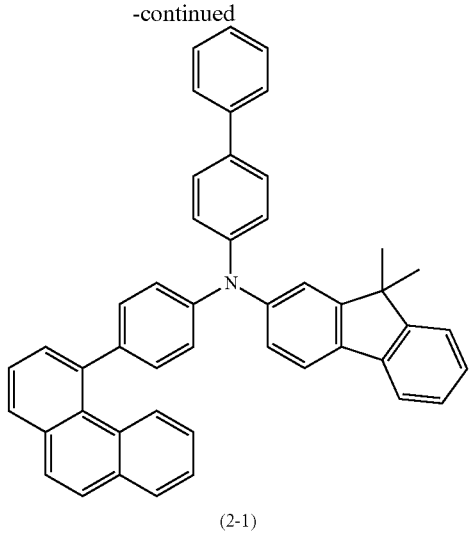

(2-1)

40 g of biphenyl-4-yl(9,9-dimethyl-9H-fluoren-2-yl)amine (111 mmol) and 26.4 g of 4-chloroiodobenzene (111 mmol) are dissolved in 700 mL of toluene. The solution is degassed and saturated with $N_2$. Thereafter, 4.4 mL (4.4 mmol) of a 1 M tri-tert-butylphosphine solution and 0.5 g (2.21 mmol) of palladium(II) acetate are added thereto, and then 15.9 g of sodium tert-butoxide (166 mmol) are added. The reaction mixture is heated to boiling under a protective atmosphere for 5 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene. The yield is 47 g (90% of theory).

Precursor: biphenyl-4-yl(4-chlorophenyl)(9,9-dimethyl-9H-fluoren-2-yl)amine

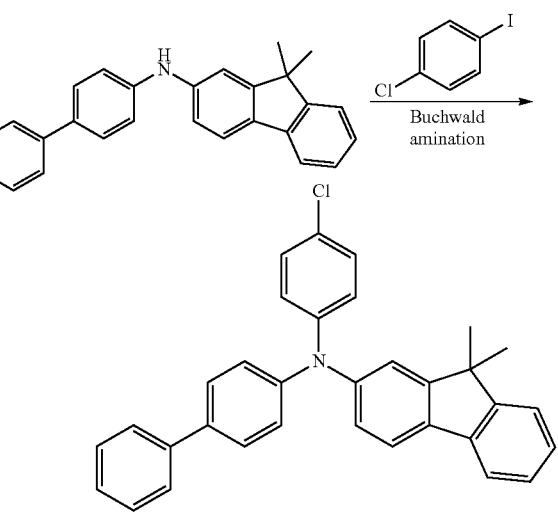

Intermediate: biphenyl-4-yl(9,9-dimethyl-9H-fluoren-2-yl)[4-(4,4,5,5-tetramethyl-[1,3,2]dioxaborolan-2-yl)phenyl]amine 20 g (42 mmol) of biphenyl-4-yl(4-chlorophenyl)(9,9-dimethyl-9H-fluoren-2-yl)amine, 12.5 g (50.8 mmol) of bis(pinacolato)diborane and 12.5 g (127 mmol) of potassium acetate are suspended in 400 mL of dioxane. To this suspension are added 1.04 g (1.27 mmol) of 1,1-bis(diphenylphosphino)ferrocenedichloropalladium(II) complex with DCM. The reaction mixture is heated under reflux for 16 h. After cooling, the organic phase is removed, washed three times with 200 mL of water and then concentrated to dryness. The residue is recrystallized from toluene (21.7 g, 91% yield).

In an analogous manner thereto, the following compounds are prepared:

| Reactant 1 | Product | Yield |
|---|---|---|
| | | 87% |

| Reactant 1 | Product | Yield |
|---|---|---|
| 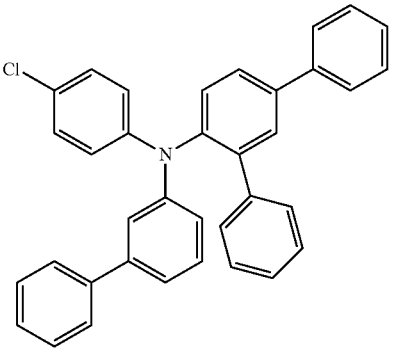 [SMILES: Clc1ccc(N(c2cccc(-c3ccccc3)c2)c2ccc(-c3ccccc3)cc2-c2ccccc2)cc1] | 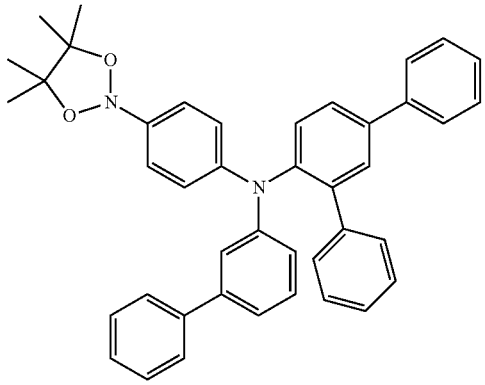 | 94% |
| 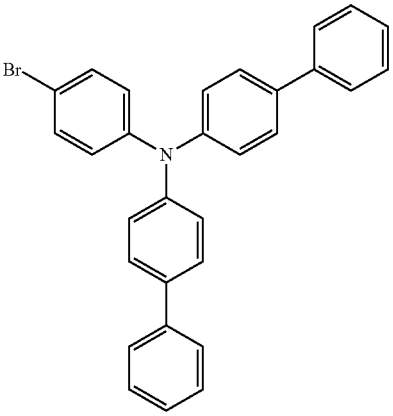 [SMILES: Brc1ccc(N(c2ccc(-c3ccccc3)cc2)c2ccc(-c3ccccc3)cc2)cc1] | 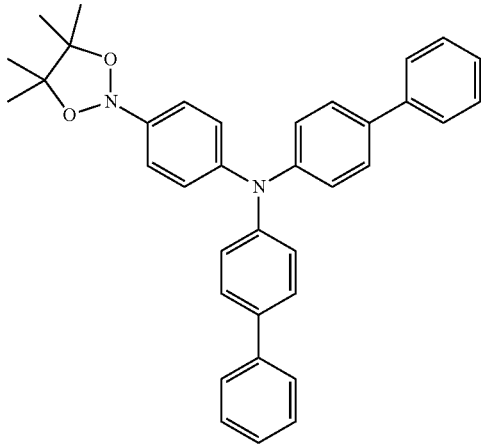 | 82% |
| 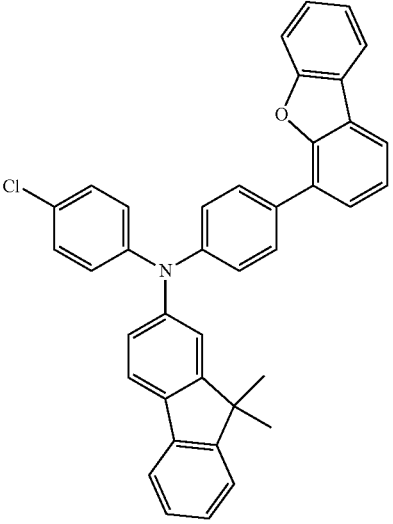 [SMILES: CC1(C)c2ccccc2-c2ccc(N(c3ccc(Cl)cc3)c3ccc(-c4cccc5c4oc4ccccc45)cc3)cc21] | 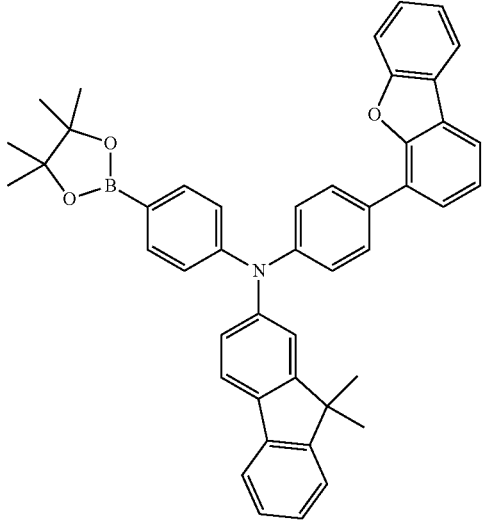 [SMILES: CC1(C)c2ccccc2-c2ccc(N(c3ccc(B4OC(C)(C)C(C)(C)O4)cc3)c3ccc(-c4cccc5c4oc4ccccc45)cc3)cc21] | 89% |

| Reactant 1 | Product | Yield |
|---|---|---|
| (structure: 3-chloro-N-(4-(dibenzothiophen-2-yl)phenyl)-N-(4'-biphenyl-4-yl)aniline) | (structure: corresponding pinacol boronate ester) | 77% |
| (structure: 2-chloro-N-(9,9-dimethyl-9H-fluoren-2-yl)-N-(biphenyl-4-yl)aniline) | (structure: corresponding pinacol boronate ester) | 89% |
| (structure: 7-chloro-9,9-dimethyl-N-(biphenyl-4-yl)-N-(9,9-dimethyl-9H-fluoren-2-yl)-9H-fluoren-2-amine) | (structure: corresponding pinacol boronate ester) | 95% |

Biphenyl-4-yl(9,9-dimethyl-9H-fluoren-2-yl)(4-phenanthren-4-ylphenyl)amine (Compound (2-1))

23 g (40.8 mmol) of biphenyl-4-yl(9,9-dimethyl-9H-fluoren-2-yl)[4-(4,4,5,5-tetramethyl-[1,3,2]dioxaborolan-2-yl)phenyl]amine, 12.1 g (37.1 mmol) of phenanthren-4-yl trifluoromethanesulfonate, 7.78 g of sodium metaborate (55.6 mmol) and 54 μL of hydrazinium hydroxide are suspended in 600 mL of THF. 0.52 g (0.742 mmol) of bis(triphenylphosphine)palladium dichloride is added to this suspension, and the reaction mixture is heated under reflux for 24 h. After cooling, the organic phase is removed, filtered through silica gel, washed three times with 100 mL of water and then concentrated to dryness. After the crude product has been filtered through silica gel with toluene, the remaining residue is recrystallized from heptane/toluene and finally sublimed under high vacuum; purity is 99.9%. The yield is 17 g (75% of theory).

Analogously, the following compounds (2-2) to (2-8) are prepared:

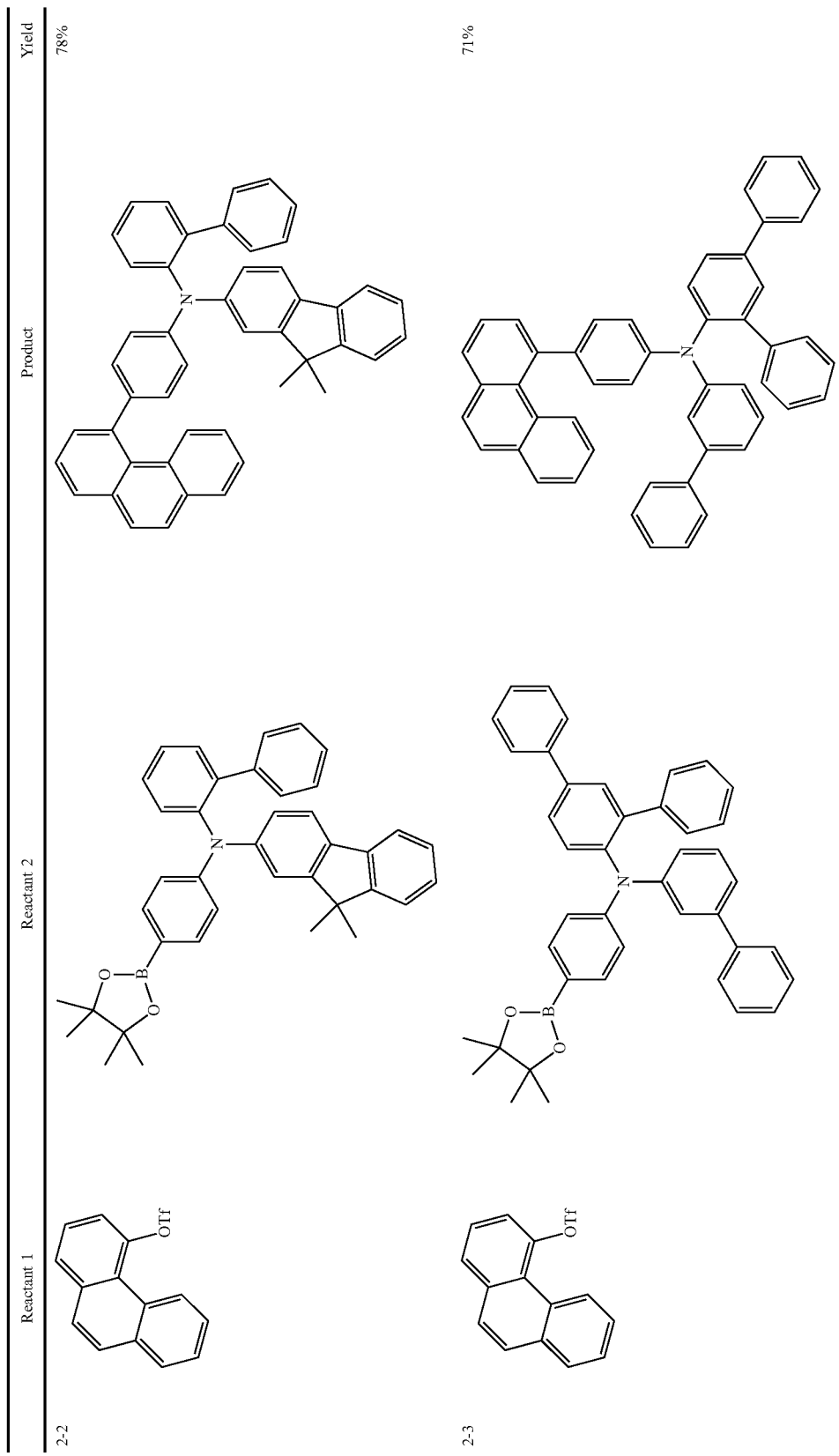

-continued
| Reactant 1 | Reactant 2 | Product | Yield |
|---|---|---|---|
| 2-4 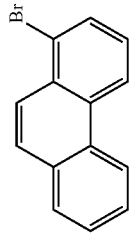 (CAS no.: 51958-51-1) | 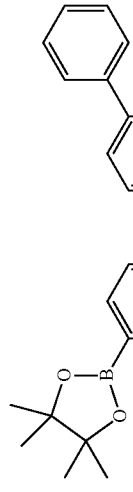 | 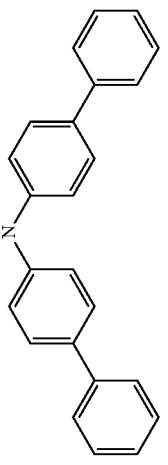 | 82% |
| 2-5 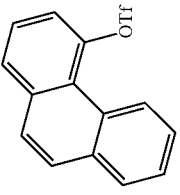 | 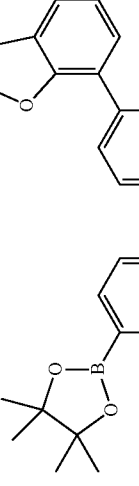 | 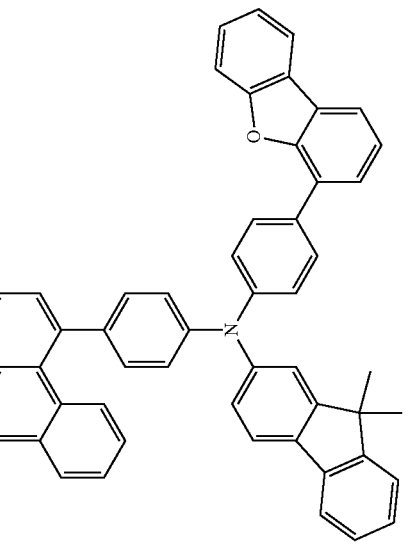 | 89% |

| | Reactant 1 | Reactant 2 | Product | Yield |
|---|---|---|---|---|
| 2-6 | phenanthrenyl-OTf | | | 69% |
| 2-7 | 4-bromophenanthrene (CAS no.: 51958-51-1) | | | 88% |

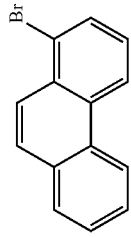

A-3) Compounds of the (3) Type

Synthesis of biphenyl-4-yl(9,9-dimethyl-9H-fluoren-2-yl)phenanthren-1-ylamine (Compound (3-1))

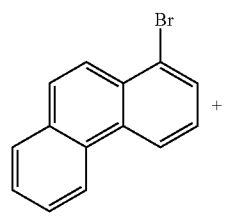

+

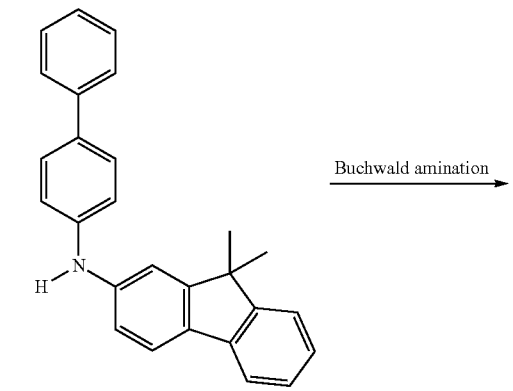

→ Buchwald amination →

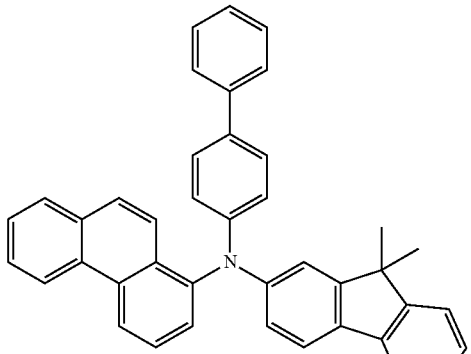

(3-1)

20 g of 1-bromophenanthrene (CAS no.: 51958-51-1) (78 mmol) and 26.7 g of biphenyl-4-yl(9,9-dimethyl-9H-fluoren-2-yl)amine (74 mmol) are dissolved in 500 mL of toluene. The solution is degassed and saturated with $N_2$. Thereafter, 3.1 mL (3.1 mmol) of a tri-tert-butylphosphine solution and 0.35 g (1.56 mmol) of palladium(II) acetate are added thereto. Subsequently, 11.6 g of sodium tert-butoxide (117 mmol) are added. The reaction mixture is heated to boiling under a protective atmosphere for 3 h. The mixture is subsequently partitioned between toluene and water, and the organic phase is washed three times with water and dried over $Na_2SO_4$ and concentrated by rotary evaporation. After the crude product has been filtered through silica gel with toluene, the remaining residue is recrystallized from heptane/toluene and finally sublimed under high vacuum; purity is 99.9% (HPLC). The yield is 33 g (80% of theory).

Analogously, the following compounds (3-2) to (3-6) are prepared:

| Reactant 1 | Reactant 2 | Product | Yield |
|---|---|---|---|
| 3-2 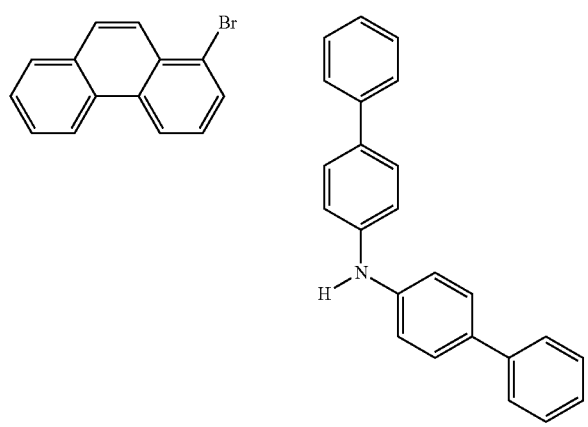 | | 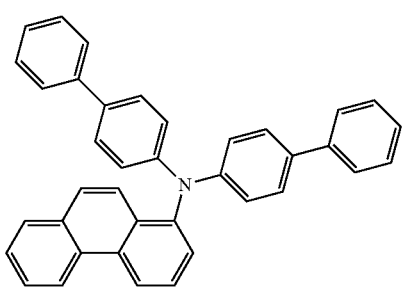 [SMILES: c1ccc(-c2ccc(N(c3ccc(-c4ccccc4)cc3)c3cccc4c3ccc3ccccc34)cc2)cc1] | 65% |

-continued
| Reactant 1 | Reactant 2 | Product | Yield |
|---|---|---|---|
| 3-3 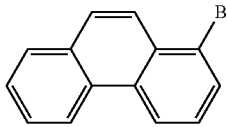 | 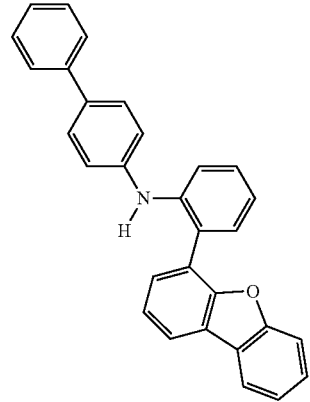 [SMILES: c1ccc(-c2ccc(Nc3ccccc3-c3cccc4c3oc3ccccc34)cc2)cc1] | 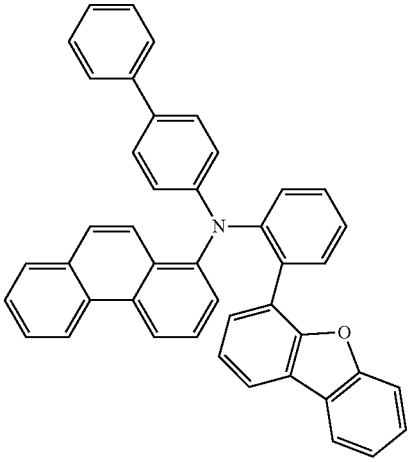 [SMILES: c1ccc(-c2ccc(N(c3ccccc3-c3cccc4c3oc3ccccc34)c3cccc4c3ccc3ccccc34)cc2)cc1] | 75% |
| 3-4 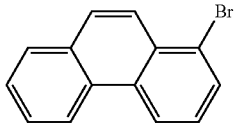 [SMILES: Brc1cccc2c1ccc1ccccc12] | 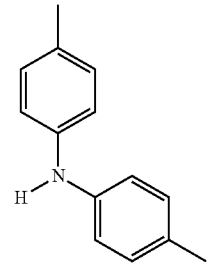 | 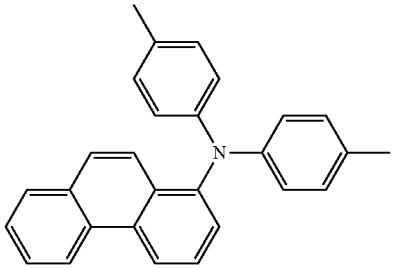 [SMILES: Cc1ccc(N(c2ccc(C)cc2)c2cccc3c2ccc2ccccc23)cc1] | 78% |
| 3-5 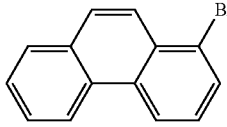 | 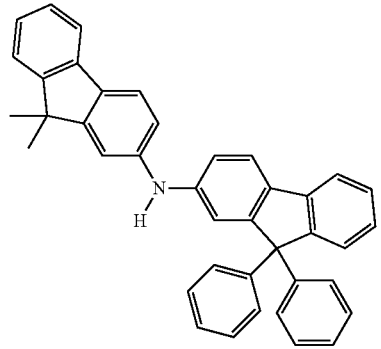 [SMILES: CC1(C)c2ccccc2-c2ccc(Nc3ccc4c(c3)C(c3ccccc3)(c3ccccc3)c3ccccc3-4)cc21] | 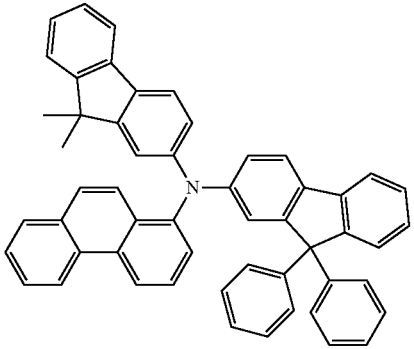 [SMILES: CC1(C)c2ccccc2-c2ccc(N(c3ccc4c(c3)C(c3ccccc3)(c3ccccc3)c3ccccc3-4)c3cccc4c3ccc3ccccc34)cc21] | 81% |
| 3-6 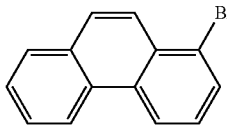 | 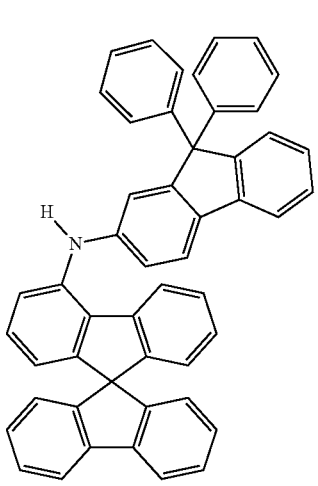 [SMILES: c1ccc(C2(c3ccccc3)c3ccccc3-c3ccc(Nc4cccc5c4-c4ccccc4C54c5ccccc5-c5ccccc54)cc32)cc1] | 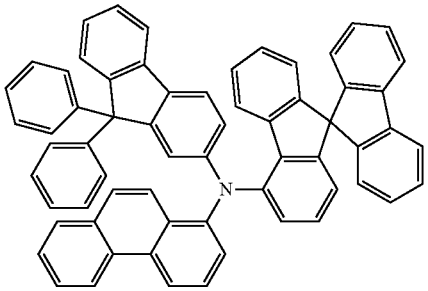 [SMILES: c1ccc(C2(c3ccccc3)c3ccccc3-c3ccc(N(c4cccc5c4-c4ccccc4C54c5ccccc5-c5ccccc54)c4cccc5c4ccc4ccccc45)cc32)cc1] | 69% |

A-4) Compounds of the (4) Type

Synthesis of N*4*-biphenyl-4-yl-N*4*-(9,9-dimethyl-9H-fluoren-2-yl)-N*1*, N*1*-di-p-tolyl-phenanthrene-1,4-diamine (4-1)

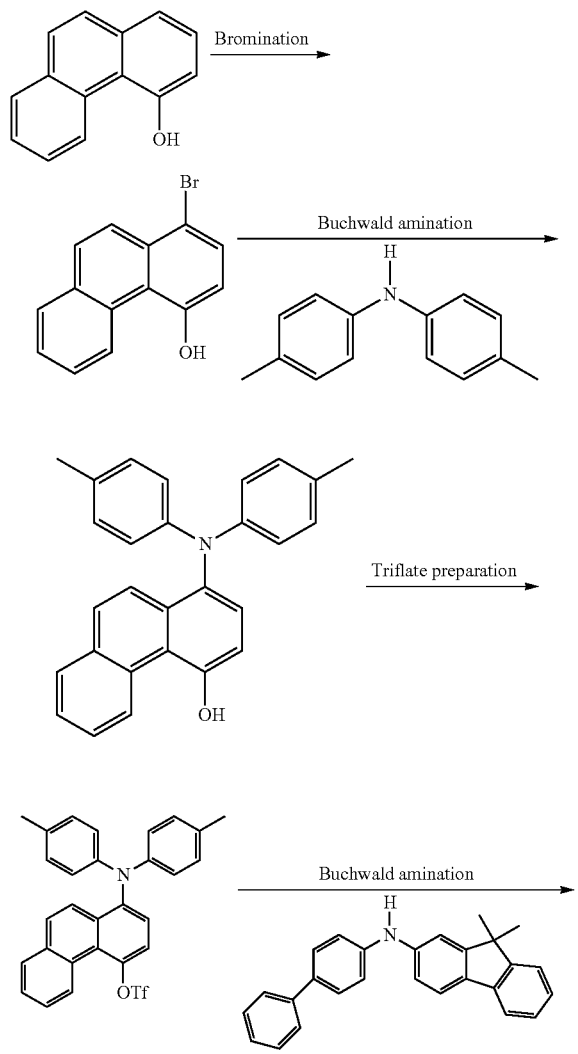

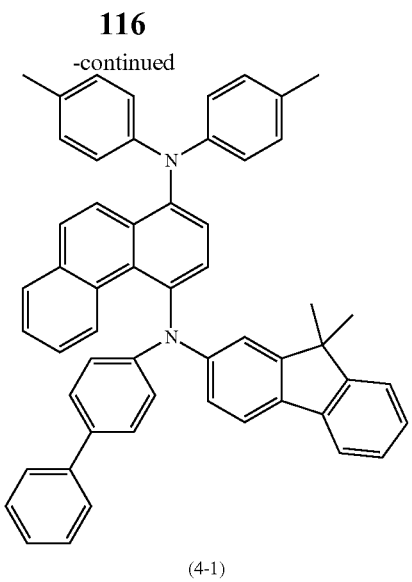

(4-1)

Precursor: 1-bromophenanthren-4-ol 40.0 g (206 mmol) of 4-phenanthrol are initially charged in 500 mL of acetonitrile. Subsequently, a solution of 38.5 g (216 mmol) of NBS in 100 mL of $CH_3CN$ is added dropwise in the dark at −15° C., the mixture is allowed to come to RT and stirring is continued at this temperature for 4 h. Subsequently, 250 mL of water are added to the mixture and extraction is effected with $CH_2Cl_2$. The organic phase is dried over $MgSO_4$ and the solvents are removed under reduced pressure. The product is subjected to extractive stirring with hot hexane and filtered off with suction.

Yield: 42.5 g (154 mmol), 75% of theory

Intermediate: 1-(di-p-tolylamino)phenanthren-4-ol

Analogously to the synthesis described above under A-3), the following compounds are also prepared:

| Reactant 1 | Reactant 2 | Product | Yield |
|---|---|---|---|
| ![Br-phenanthrenol] | ![di-p-tolylamine] | ![product] | 76% |

-continued
| Reactant 1 | Reactant 2 | Product | Yield |
|---|---|---|---|
| 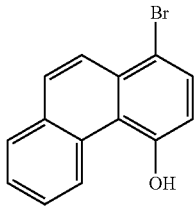 [SMILES: Oc1ccc(Br)c2ccc3ccccc3c12] | 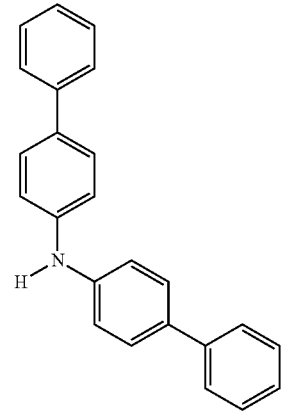 [SMILES: c1ccc(-c2ccc(Nc3ccc(-c4ccccc4)cc3)cc2)cc1] | 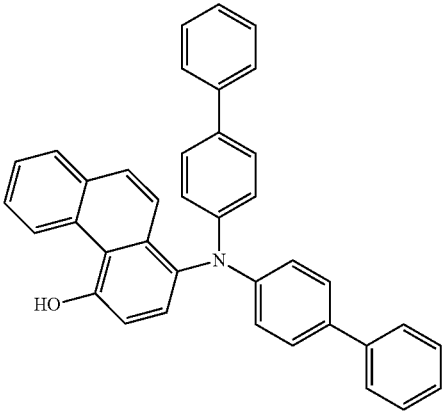 [SMILES: Oc1ccc(N(c2ccc(-c3ccccc3)cc2)c2ccc(-c3ccccc3)cc2)c2ccc3ccccc3c12] | 69% |
| 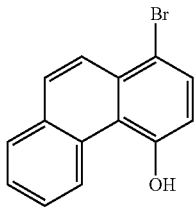 [SMILES: Oc1ccc(Br)c2ccc3ccccc3c12] | 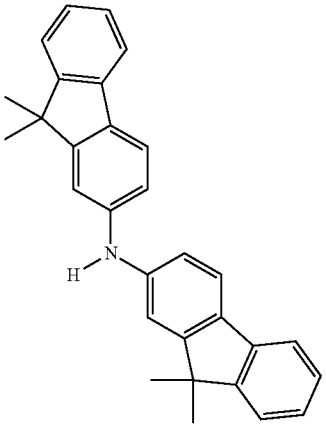 [SMILES: CC1(C)c2ccccc2-c2ccc(Nc3ccc4c(c3)C(C)(C)c3ccccc3-4)cc21] | 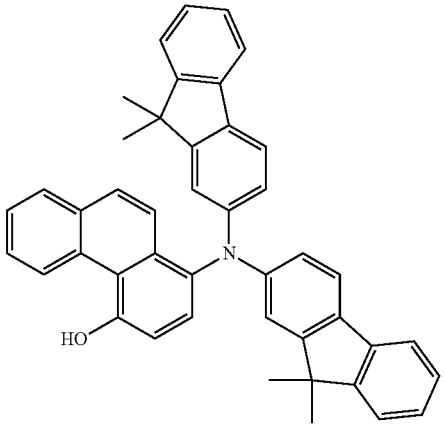 [SMILES: CC1(C)c2ccccc2-c2ccc(N(c3ccc4c(c3)C(C)(C)c3ccccc3-4)c3ccc(O)c4c3ccc3ccccc34)cc21] | 78% |
Analogously to the synthesis of the phenanthren-4-yl trifluoromethanesulfonate intermediate described, the following compounds are also prepared:
| Reactant 1 | Product | Yield |
|---|---|---|
| 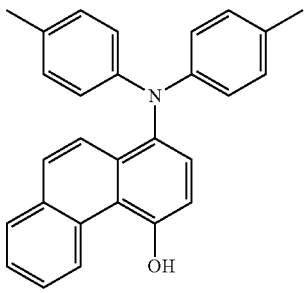 | 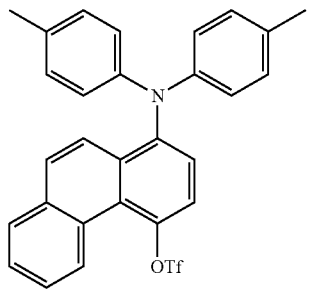 | 86% |

| Reactant 1 | Product | Yield |
|---|---|---|
| [structure: 4-hydroxyphenanthrene with N(biphenyl)(biphenyl) substituent] | [structure: 4-OTf phenanthrene with N(biphenyl)(biphenyl) substituent] | 89% |
| [structure: 4-hydroxyphenanthrene with N(9,9-dimethylfluoren-2-yl)₂ substituent] | [structure: 4-OTf phenanthrene with N(9,9-dimethylfluoren-2-yl)₂ substituent] | 93% |

Analogously to the manner described above for compounds of the formula (1-1), the following compounds (4-2) to (4-4) are prepared:

| | Reactant 1 | Reactant 2 | Product | Yield |
|---|---|---|---|---|
| 4-2 | [structure: phenanthrene with N(p-tolyl)₂ and OTf] | [structure: 9,9-dimethylfluorenyl-NH-biphenyl] | [structure: phenanthrene bis-amine product] | 68% |

-continued
| | Reactant 1 | Reactant 2 | Product | Yield |
|---|---|---|---|---|
| 4-3 | | | | 61% |
| 4-4 | | | | 69% |
A-5) Compounds of the (5) Type
Bis(9,9-dimethyl-9H-fluoren-2-yl)(4-phenylphenanthren-1-yl)amine (5-1)
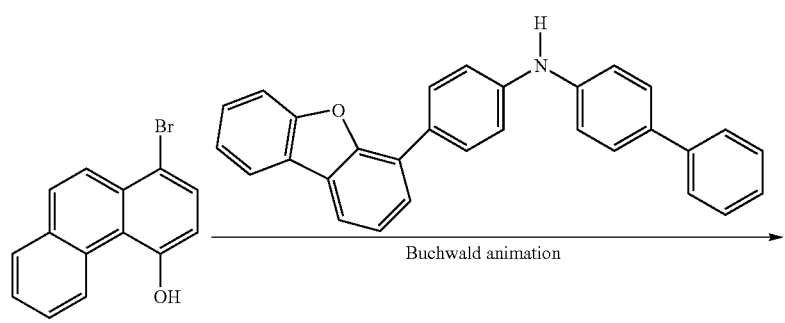

-continued
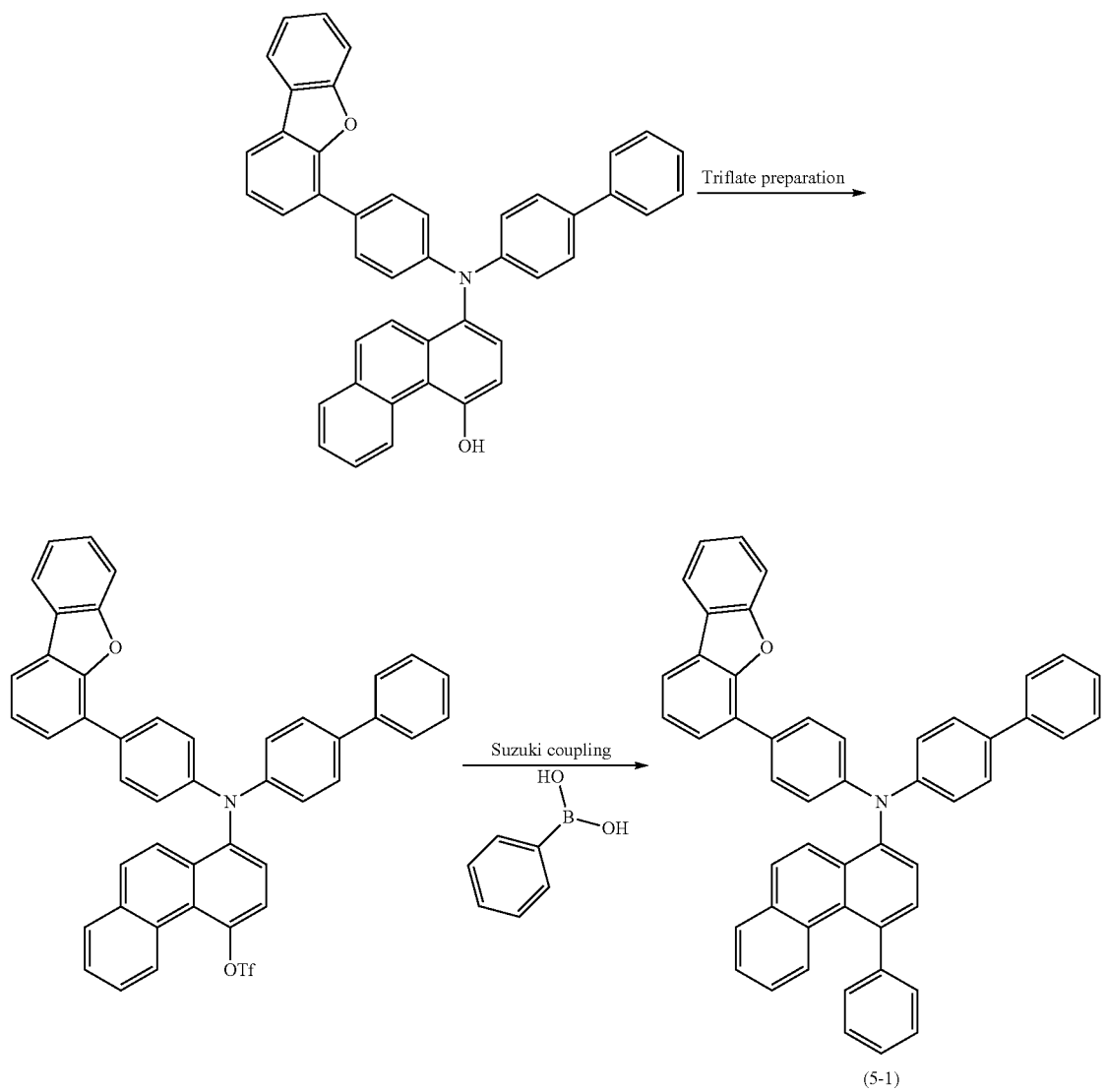
Analogously to the manner described above under (2-1), the following compounds (5-2) to (5-4) are also prepared:
| | Reactant 1 | Reactant 2 | Product | Yield |
|---|---|---|---|---|
| 5-2 | | | | 68% |

-continued
| | Reactant 1 | Reactant 2 | Product | Yield |
|---|---|---|---|---|
| 5-3 | 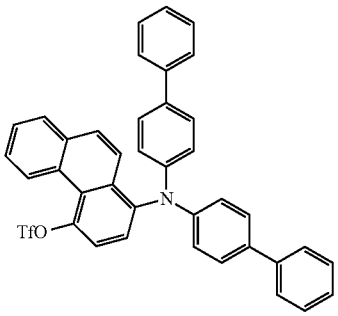 [SMILES: O=S(=O)(Oc1ccc(N(c2ccc(-c3ccccc3)cc2)c2ccc(-c3ccccc3)cc2)c2ccc3ccccc3c12)C(F)(F)F] | 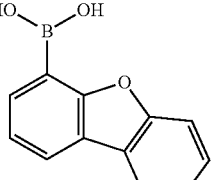 | 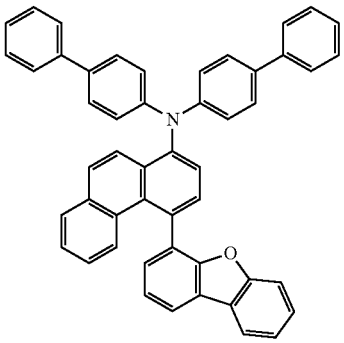 [SMILES: c1ccc(-c2ccc(N(c3ccc(-c4ccccc4)cc3)c3ccc(-c4cccc5c4oc4ccccc45)c4c3ccc3ccccc34)cc2)cc1] | 61% |
| 5-4 | 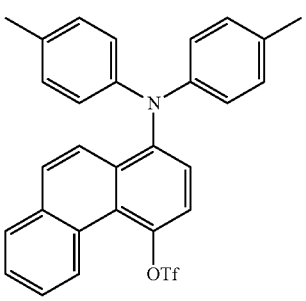 | 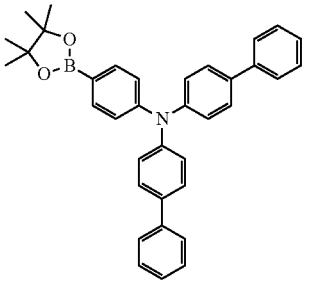 [SMILES: CC1(C)OB(c2ccc(N(c3ccc(-c4ccccc4)cc3)c3ccc(-c4ccccc4)cc3)cc2)OC1(C)C] | 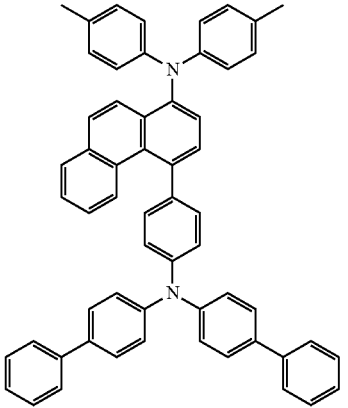 [SMILES: Cc1ccc(N(c2ccc(C)cc2)c2ccc(-c3ccc(N(c4ccc(-c5ccccc5)cc4)c4ccc(-c5ccccc5)cc4)cc3)c3c2ccc2ccccc23)cc1] | 69% |
A-6) Compounds of the (6) Type
Biphenyl-4-yl{1-[4-(bis(biphenyl-4-yl)amino)phenyl]phenanthren-4-yl}(9,9-dimethyl-9H-fluoren-2-yl)amine (6-1)
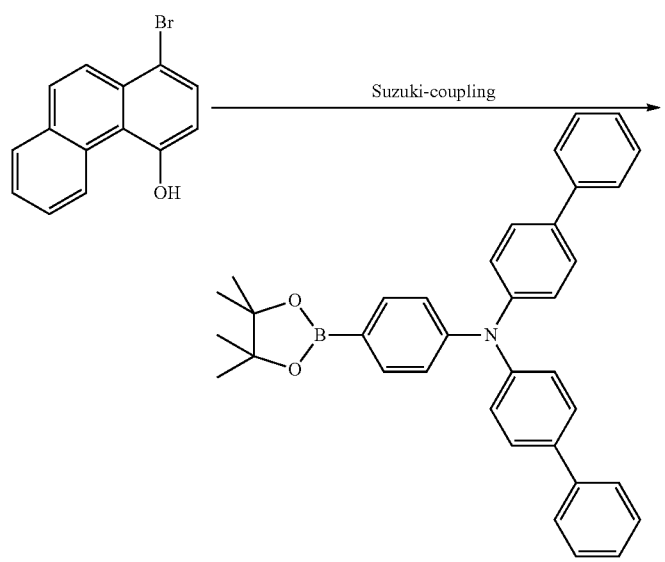

-continued
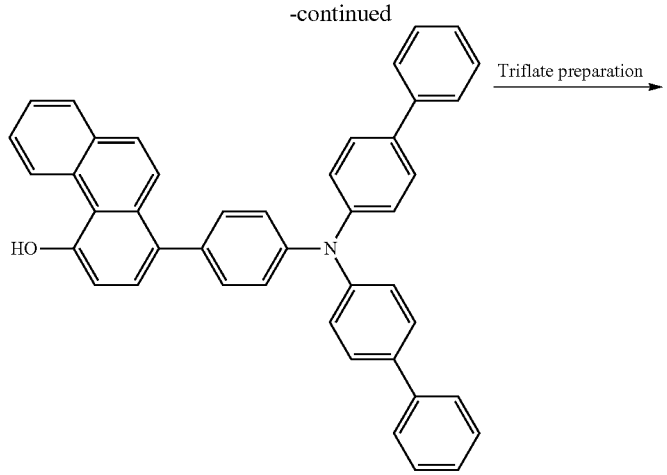
Triflate preparation →
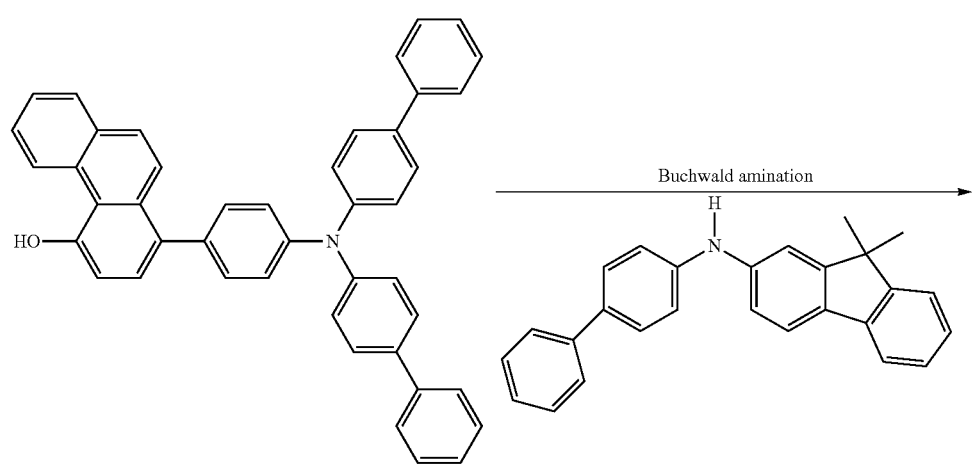
Buchwald amination →
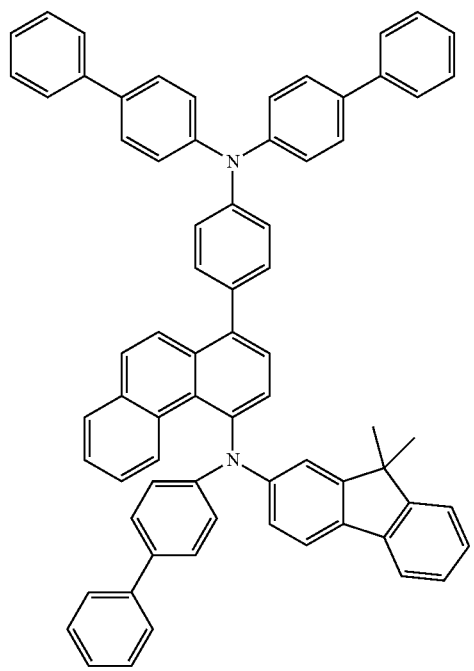
(6-1)

Analogously to the synthesis described above under A-2), the following compounds are also prepared:
| Reactant 1 | Reactant 2 | Product | Yield |
|---|---|---|---|
| 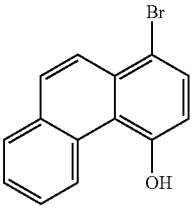 [SMILES: Oc1ccc(Br)c2ccc3ccccc3c12] | 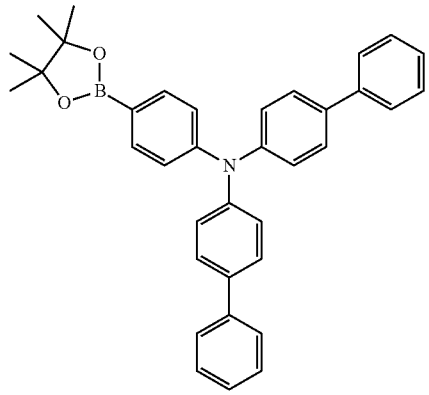 [SMILES: CC1(C)OB(c2ccc(N(c3ccc(-c4ccccc4)cc3)c3ccc(-c4ccccc4)cc3)cc2)OC1(C)C] | 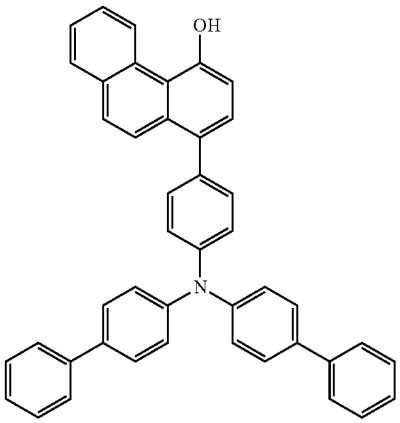 [SMILES: Oc1ccc(-c2ccc(N(c3ccc(-c4ccccc4)cc3)c3ccc(-c4ccccc4)cc3)cc2)c2ccc3ccccc3c12] | 82% |
| 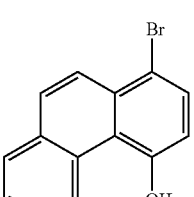 | 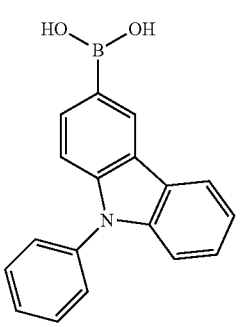 [SMILES: OB(O)c1ccc2c(c1)c1ccccc1n2-c1ccccc1] | 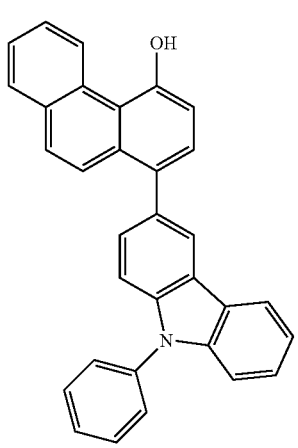 [SMILES: Oc1ccc(-c2ccc3c(c2)c2ccccc2n3-c2ccccc2)c2ccc3ccccc3c12] | 85% |
| 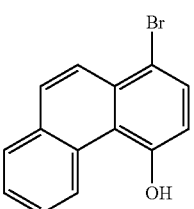 | 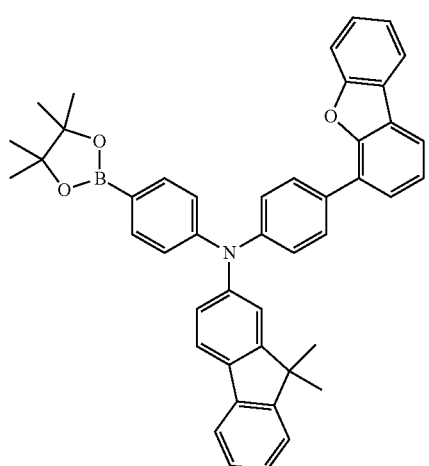 | 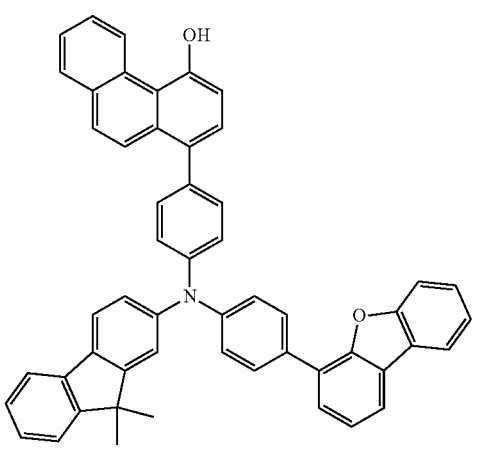 [SMILES: CC1(C)c2ccccc2-c2ccc(N(c3ccc(-c4ccc(O)c5c4ccc4ccccc45)cc3)c3ccc(-c4cccc5c4oc4ccccc45)cc3)cc21] | 69% |

Analogously to the synthesis of the phenanthren-4-yl trifluoromethanesulfonate intermediate described, the following compounds are also prepared:

| Reactant 1 | Product | Yield |
|---|---|---|
| | | 81% |
| | | 93% |
| | | 89% |

Analogously to the synthesis described above for (1-1), the following compounds (6-2) to (6-4) are prepared:

| | Reactant 1 | Reactant 2 | Product | Yield |
|---|---|---|---|---|
| 6-2 | | | | 58% |
| 6-3 | | | | 52% |
| 6-4 | | | | 63% |

B) Device Examples

OLEDs of the invention and OLEDs according to the prior art are produced by a general method according to WO 04/058911, which is adapted to the circumstances described here (e.g. materials).

In the inventive examples I1-I9 which follow and in reference examples C1-C4, the data of various OLEDs are presented. Substrates used are glass plates coated with structured ITO (indium tin oxide) of thickness 50 nm. The OLEDs have the following layer structure: substrate/p-doped hole transport layer (HIL1)/hole transport layer (HTL)/p-doped hole transport layer (HIL2)/hole transport layer (EBL)/emission layer (EML)/electron transport layer (ETL)/electron injection layer (EIL) and finally a cathode. In each of examples C3, C4 and I4-I9, the layers HIL2 and EBL are omitted. The cathode is formed by an aluminum layer of thickness 100 nm. The materials required for production of the OLEDs are shown in table 1, and the various component structures in table 2.

All materials are applied by thermal vapor deposition in a vacuum chamber. In this case, the emission layer always consists of at least one matrix material (host material) and an emitting dopant (emitting compound) which is added to the matrix material(s) in a particular proportion by volume by co-evaporation. Details given in such a form as H1:SEB (5%) mean here that the material H1 is present in the layer in a proportion by volume of 95% and SEB in a proportion by volume of 5%. In an analogous manner, the electron transport layers or the hole injection layers may also consist of a mixture of two or more materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian radiation characteristics, and also the lifetime are determined. The electroluminescence spectra are determined at a luminance of 1000 cd/m$^2$, and the CIE 1931 x and y color coordinates are calculated therefrom. The parameter EQE @ 10 mA/cm$^2$ refers to the external quantum efficiency at a current density of 10 mA/cm$^2$. LD80 @ 60 mA/cm$^2$ is the lifetime before the OLED, given a starting brightness at constant current of 60 mA/cm$^2$, has fallen to 80% of the starting intensity.

TABLE 1

Structures of the materials used

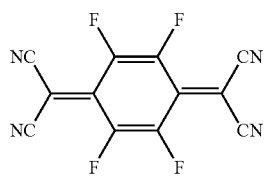 [SMILES: N#CC(C#N)=c1c(F)c(F)c(=C(C#N)C#N)c(F)c1F]

F4TCNQ

TABLE 1-continued

Structures of the materials used

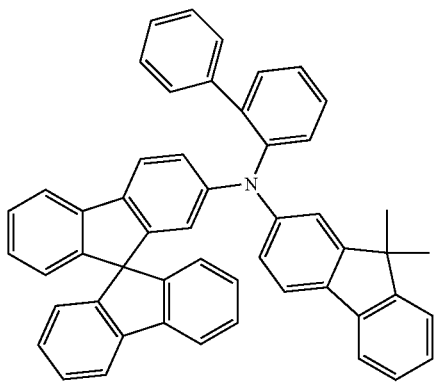 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HIM

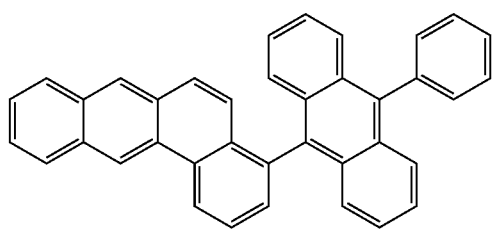 [SMILES: c1ccc(-c2c3ccccc3c(-c3cccc4c3ccc3cc5ccccc5cc34)c3ccccc23)cc1]

H1

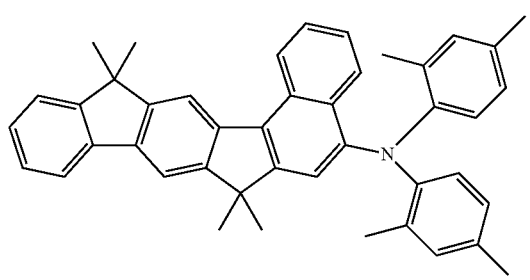 [SMILES: Cc1ccc(N(c2ccc(C)cc2C)c2cc3c(c4ccccc24)-c2cc4c(cc2C3(C)C)-c2ccccc2C4(C)C)c(C)c1]

SEB

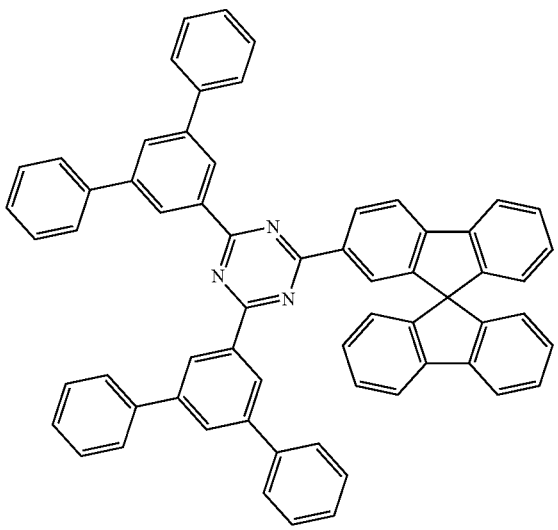 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETM

TABLE 1-continued
Structures of the materials used
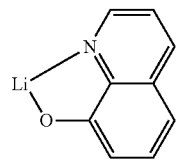
LiQ
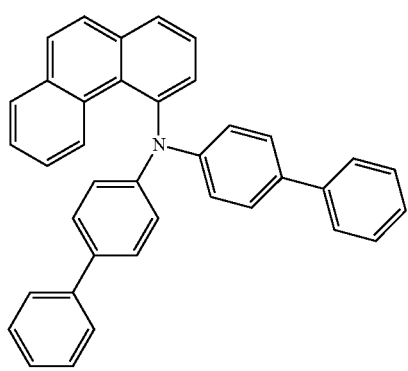 [SMILES: c1ccc(-c2ccc(N(c3ccc(-c4ccccc4)cc3)c3cccc4ccc5ccccc5c34)cc2)cc1]
HTM1
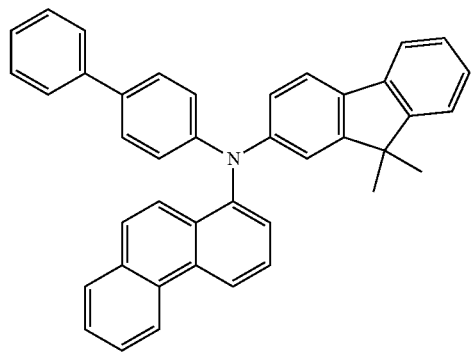 [SMILES: CC1(C)c2ccccc2-c2ccc(N(c3ccc(-c4ccccc4)cc3)c3cccc4c3ccc3ccccc34)cc21]
HTM2
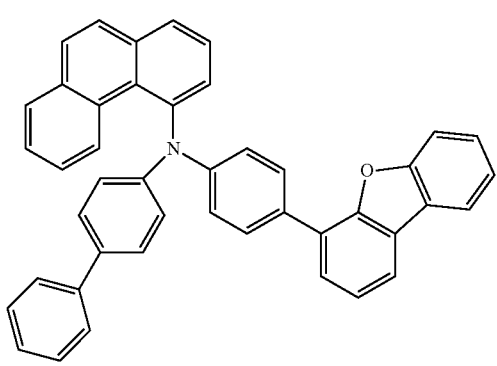 [SMILES: c1ccc(-c2ccc(N(c3ccc(-c4cccc5c4oc4ccccc45)cc3)c3cccc4ccc5ccccc5c34)cc2)cc1]
HTM3
TABLE 1-continued
Structures of the materials used
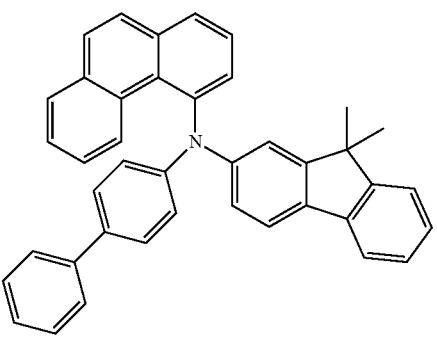 [SMILES: CC1(C)c2ccccc2-c2ccc(N(c3ccc(-c4ccccc4)cc3)c3cccc4ccc5ccccc5c34)cc21]
HTM4
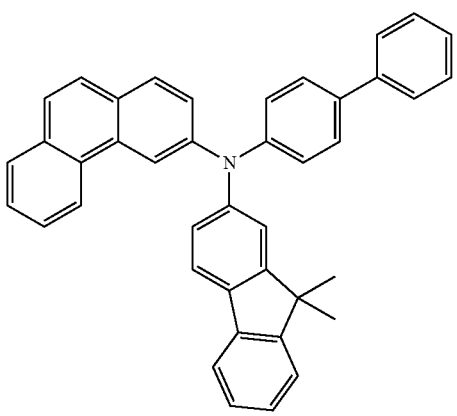 [SMILES: CC1(C)c2ccccc2-c2ccc(N(c3ccc(-c4ccccc4)cc3)c3ccc4ccc5ccccc5c4c3)cc21]
HTMC1
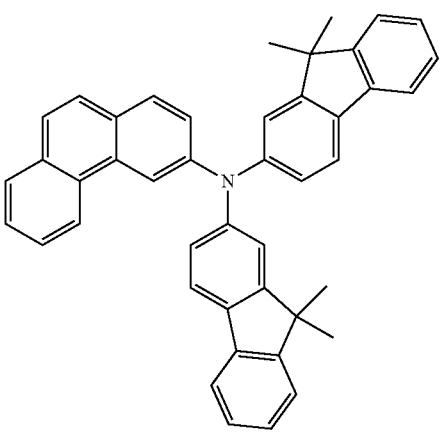 [SMILES: CC1(C)c2ccccc2-c2ccc(N(c3ccc4c(c3)C(C)(C)c3ccccc3-4)c3ccc4ccc5ccccc5c4c3)cc21]
HTMC2

TABLE 1-continued

Structures of the materials used

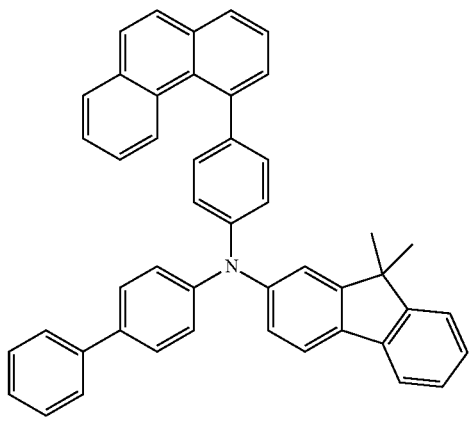 [SMILES: CC1(C)c2ccccc2-c2ccc(N(c3ccc(-c4ccccc4)cc3)c3ccc(-c4cccc5ccc6ccccc6c45)cc3)cc21]

HTM5

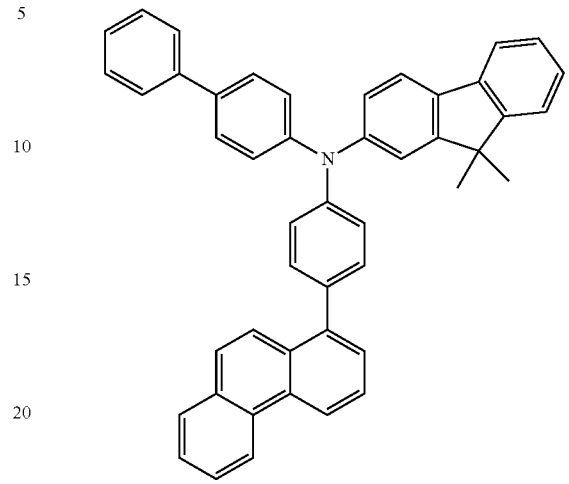

HTM6

TABLE 2

Structure of the OLEDs

| Exp. | HIL1 Thickness/nm | HTL Thickness/nm | HIL2 Thickness/nm | EBL Thickness/nm | EML Thickness/nm | ETL Thickness/nm | EIL Thickness/nm |
|---|---|---|---|---|---|---|---|
| C1 | HIM: F4TCNQ(5%) 20 nm | HIM 155 nm | HTMC1: F4TCNQ(5%) 20 nm | HTMC1 20 nm | H1: SEB(5%) 20 nm | ETM: LiQ(50%) 30 nm | LiQ 1 nm |
| C2 | HIM: F4TCNQ(5%) 20 nm | HIM 155 nm | HTMC2: F4TCNQ(5%) 20 nm | HTMC2 20 nm | H1: SEB(5%) 20 nm | ETM: LiQ(50%) 30 nm | LiQ 1 nm |
| I1 | HIM: F4TCNQ(5%) 20 nm | HIM 155 nm | HTM1: F4TCNQ(5%) 20 nm | HTM1 20 nm | H1: SEB1(5%) 20 nm | ETM: LiQ(50%) 30 nm | LiQ 1 nm |
| I2 | HIM: F4TCNQ(5%) 20 nm | HIM 155 nm | HTM2: F4TCNQ(5%) 20 nm | HTM2 20 nm | H1: SEB1(5%) 20 nm | ETM: LiQ(50%) 30 nm | LiQ 1 nm |
| I3 | HIM: F4TCNQ(5%) 20 nm | HIM 155 nm | HTM3: F4TCNQ(5%) 20 nm | HTM3 20 nm | H1: SEB1(5%) 20 nm | ETM: LiQ(50%) 30 nm | LiQ 1 nm |
| C3 | HTMC1: F4TCNQ(5%) 20 nm | HTMC1 180 nm | — | — | H1: SEB1(5%) 20 nm | ETM: LiQ(50%) 30 nm | LiQ 1 nm |
| C4 | HTMC2: F4TCNQ(5%) 20 nm | HTMC2 180 nm | — | — | H1: SEB1(5%) 20 nm | ETM: LiQ(50%) 30 nm | LiQ 1 nm |
| I4 | HTM4: F4TCNQ(5%) 20 nm | HTM4 180 nm | — | — | H1: SEB1(5%) 20 nm | ETM: LiQ(50%) 30 nm | LiQ 1 nm |
| I5 | HTM3: F4TCNQ(5%) 20 nm | HTM3 180 nm | — | — | H1: SEB1(5%) 20 nm | ETM: LiQ(50%) 30 nm | LiQ 1 nm |
| I6 | HTM2: F4TCNQ(5%) 20 nm | HTM2 180 nm | — | — | H1: SEB1(5%) 20 nm | ETM: LiQ(50%) 30 nm | LiQ 1 nm |
| I7 | HTM1: F4TCNQ(5%) 20 nm | HTM1 180 nm | — | — | H1: SEB1(5%) 20 nm | ETM: LiQ(50%) 30 nm | LiQ 1 nm |
| I8 | HTM5: F4TCNQ(5%) 20 nm | HTM5 180 nm | — | — | H1: SEB1(5%) 20 nm | ETM: LiQ(50%) 30 nm | LiQ 1 nm |
| I9 | HTM6: F4TCNQ(5%) 20 nm | HTM6 180 nm | — | — | H1: SEB1(5%) 20 nm | ETM: LiQ(50%) 30 nm | LiQ 1 nm |

Example 1

In example 1, three inventive substances (HTM1, HTM2 and HTM3) and two reference substances (HTMC1, HTMC2) are compared in an OLED having a blue-fluorescing emitting layer. The compounds are each used in hole-transporting layers of the OLED.

The reference sample C1, containing a 3-phenanthrene compound, is compared with two components of the invention containing a 4-phenanthrene (I1) or a 1-phenanthrene compound (I2). The lifetime LD80 at 60 mA/cm$^2$ is much better in the case of the inventive samples I1 (357 h) and I2 (381 h) than the reference sample C1 (128 h).

The external quantum efficiency at 10 mA/cm$^2$ of the inventive compound formed from sample I3 (of a 4-phenanthrene compound) is much better at 7.7% than that of the reference sample C2 at only 6.6%. The reference sample C2 contains a 3-phenanthrene compound.

Example 2

In the case of OLEDs having a blue-fluorescing emitting layer (in a reduced design; direct injection of the holes from the HTL into the EML), the reference samples C3 (6.8%) and C4 (4.2%) have lower quantum efficiency at 10 mA/cm$^2$ than the inventive samples I4 (7.9%) and I5 (7.7%). The lifetime (80%) at 60 mA/cm$^2$ of the inventive samples I6 (356 h) and I7 (218 h) is also greater than in the case of the references C3 (106 h) and C4 (43 h). In this example too, the reference samples contain 3-phenanthrene compounds. The inventive samples I4, I5, I6 and I7 contain 1-phenanthrene compounds or 4-phenanthrene compounds.

Example 3

In addition, two components I8 and I9 comprising the inventive compounds HTM5 and HTM6 are produced. These two compounds are characterized in that they have a phenyl group between the phenanthrene group and the diarylamino group. The components are produced with a reduced design like those of example 2. For components I8 and I9, external quantum efficiencies of 7.3% and 8.1% respectively are measured.

The invention claimed is:

1. A compound containing a phenanthrene group of the formulae (I-1) or (I-2):

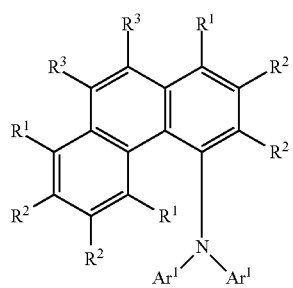

Formula (I-1)

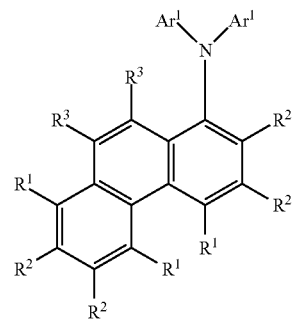

Formula (I-2)

where the symbols that occur are as follows:

$R^1$ is the same or different at each instance and is selected from H, D, F, C(=O)R$^6$, CN, Si(R$^6$)$_3$, P(=O)(R$^6$)$_2$, OR$^6$, S(=O)R$^6$, S(=O)$_2$R$^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and may be substituted by one or more R$^6$ radicals, and heteroaromatic ring systems which have 5 to 40 aromatic ring atoms and may be substituted by one or more R$^6$ radicals, where the alkyl, alkoxy, alkenyl and alkynyl groups may each be substituted by one or more R$^6$ radicals and where one or more CH$_2$ groups in the alkyl, alkoxy, alkenyl and alkynyl groups may be replaced by —R$^6$C=CR$^6$—, —C≡C—, Si(R$^6$)$_2$, C=O, C=NR$^6$, —C(=O)O—, —C(=O)NR$^6$—, NR$^6$, P(=O)(R$^6$), —O—, —S—, SO or SO$_2$, $R^2$, $R^3$ are the same or different at each instance and are selected from H, D, F, C(=O)R$^6$, CN, Si(R$^6$)$_3$, P(=O)(R$^6$)$_2$, OR$^6$, S(=O)R$^6$, S(=O)$_2$R$^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and is optionally substituted by one or more R$^6$ radicals, and heteroaromatic ring systems which have 5 to 40 aromatic ring atoms and is optionally substituted by one or more R$^6$ radicals, where the alkyl, alkoxy, alkenyl and alkynyl groups may each be substituted by one or more R$^6$ radicals, and where one or more CH$_2$ groups in the alkyl, alkoxy, alkenyl and alkynyl groups is optionally replaced by —R$^6$C=CR$^6$—, —C≡C—, Si(R$^6$)$_2$, C=O, C=NR$^6$, —C(=O)O—, —C(=O)NR$^6$—, NR$^6$, P(=O)(R$^6$), —O—, —S—, SO or SO$_2$, $R^6$ is the same or different at each instance and is selected from H, D, F, C(=O)R$^7$, CN, Si(R$^7$)$_3$, P(=O)(R$^7$)$_2$, OR$^7$, S(=O)R$^7$, S(=O)$_2$R$^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems which have 6 to 40 aromatic ring atoms and is optionally substituted by one or more R$^7$ radicals, and heteroaromatic ring systems which have 5 to 40 aromatic ring atoms and is optionally substituted by one or more R$^7$ radicals, where the alkyl, alkoxy, alkenyl and alkynyl groups may each be substituted by one or more $R^7$ radicals, where one or more $CH_2$ groups in the alkyl, alkoxy, alkenyl and alkynyl groups is optionally replaced by —$R^7C$=$CR^7$—, —C≡C—, $Si(R^7)_2$, C=O, C=$NR^7$, —C(=O)O—, —C(=O)$NR^7$—, $NR^7$, P(=O)($R^7$), —O—, —S—, SO or $SO_2$;

$R^7$ is the same or different at each instance and is selected from H, D, F, CN and aliphatic, aromatic or heteroaromatic organic radicals having 1 to 20 carbon atoms, in which one or more hydrogen atoms may also be replaced by D, F or CN;

$Ar^1$ is selected, identically or differently, from benzene, naphthalene, fluoranthene, biphenyl, terphenyl, quaterphenyl, fluorene, spirobifluorene, furan, benzofuran, isobenzofuran, dibenzofuran, thiophene, benzothiophene, isobenzothiophene, dibenzothiophene, indole, isoindole, carbazole, indolocarbazole, indenocarbazole, pyridine, quinoline, isoquinoline, acridine, phenanthridine, benzimidazole, pyrimidine, pyrazine and triazine, each optionally substituted by one or more R4 radicals;

$R^4$ are the same or different at each instance and are selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, where the alkyl and alkoxy groups mentioned may each be substituted by one or more $R^6$ radicals and where one or more $CH_2$ groups in the alkyl and alkoxy groups mentioned may be replaced by —C≡C—, —$R^6C$=$CR^6$—, $Si(R^6)_2$, C=O, C=$NR^6$, —$NR^6$—, —O—, —S—, —C(=O)O— or —C(=O)$NR^6$—; or benzene, naphthalene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, each of which may be substituted by one or more $R^6$ radicals.

2. The compound as claimed in claim 1, wherein two $Ar^1$ groups bonded to the same nitrogen atom are not the same.

3. The compound as claimed in claim 1, wherein $R^6$ is the same or different at each instance and is selected from H, D, F, CN, $Si(R^7)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and is optionally substituted by one or more $R^7$ radicals, and heteroaromatic ring systems which have 5 to 24 aromatic ring atoms and is optionally substituted by one or more $R^7$ radicals, where the alkyl and alkoxy groups may each be substituted by one or more $R^7$ radicals and where one or more $CH_2$ groups in the alkyl and alkoxy groups is optionally replaced by —C≡C—, —$R^7C$=$CR^7$—, $Si(R^7)_2$, C=O, C=$NR^7$, —$NR^7$—, —O—, —S—, —C(=O)O— or —C(=O)$NR^7$—.

4. A process for preparing the compound as claimed in claim 1, which comprises reacting a phenanthrene compound substituted by a leaving group in the 1 and/or 4 position in a coupling reaction with a diarylamino compound or with a triarylamino compound substituted by a leaving group.

5. An oligomer, polymer or dendrimer containing one or more compounds as claimed in claim 1, wherein the bond(s) to the polymer, oligomer or dendrimer is optionally localized at any positions substituted by $R^1$, $R^2$, $R^3$, $R^4$, $R^6$ or $R^7$ in formula (I).

6. A formulation comprising at least one compound as claimed in claim 1 and at least one solvent.

7. An electronic device selected from organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs), comprising at least one compound as claimed in claim 1.

8. An organic electroluminescent device comprising cathode, anode and at least one organic layer comprising at least one compound as claimed in claim 1.

9. An organic electroluminescent device which comprises the compound as claimed in claim 1 as hole transport material in a hole transport layer, an electron blocker layer or a hole injection layer, or as emitting compound in an emitting layer, or as matrix compound together with one or more emitting compounds in an emitting layer.

10. The compound as claimed in claim 1, wherein $Ar^1$ is selected, identically or differently on each occurrence, from formulae ($Ar^1$-1) to ($Ar^1$-59)

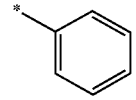

Formula ($Ar^1$-1)

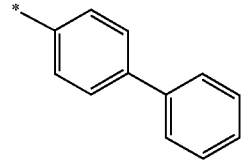

Formula ($Ar^1$-2)

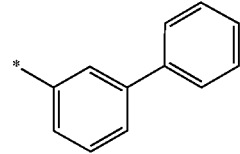

Formula ($Ar^1$-3)

Formula (Ar¹-4)
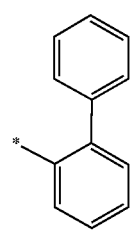
Formula (Ar¹-5)
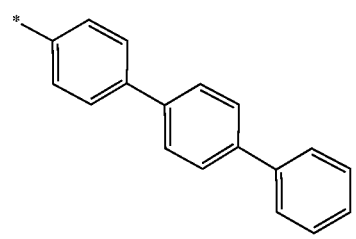
Formula (Ar¹-6)
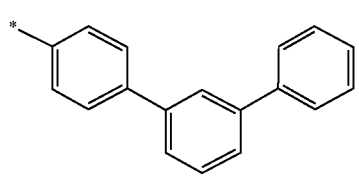
Formula (Ar¹-7)
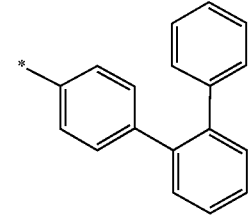
Formula (Ar¹-8)
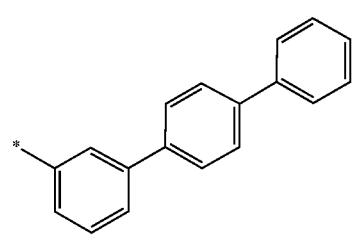
Formula (Ar¹-9)
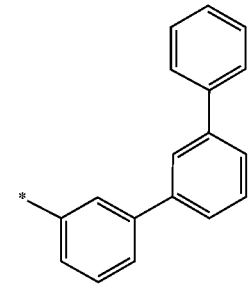
Formula (Ar¹-10)
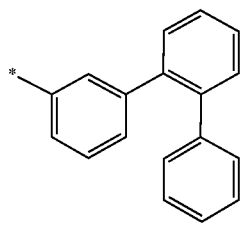
Formula (Ar¹-11)
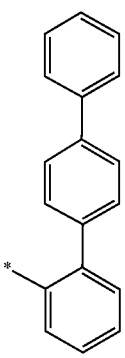
Formula (Ar¹-12)
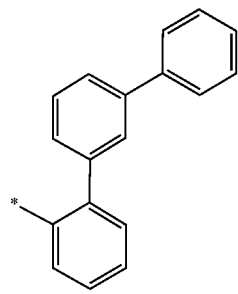
Formula (Ar¹-13)
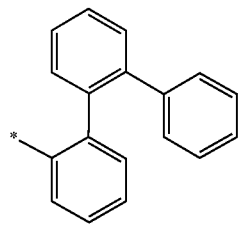
Formula (Ar¹-14)
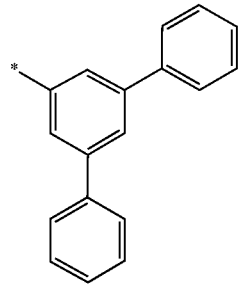

Formula (Ar¹-15)
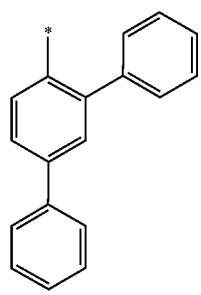
Formula (Ar¹-16)
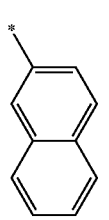
Formula (Ar¹-17)
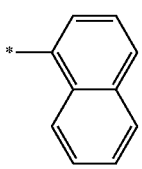
Formula (Ar¹-18)
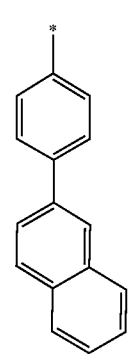
Formula (Ar¹-19)
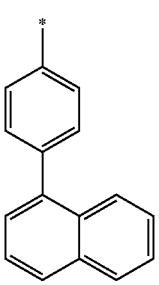
Formula (Ar¹-20)
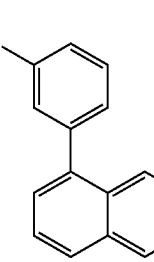
Formula (Ar¹-21)
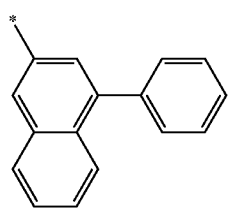
Formula (Ar¹-22)
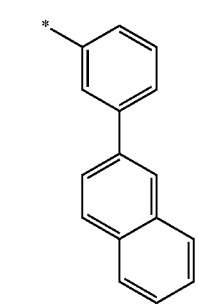
Formula (Ar¹-23)
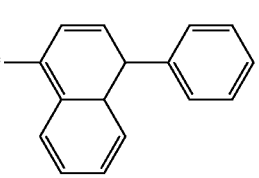
Formula (Ar¹-24)
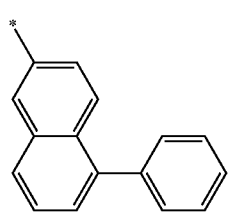
Formula (Ar¹-25)
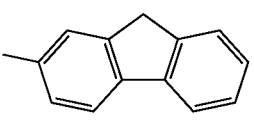
Formula (Ar¹-26)
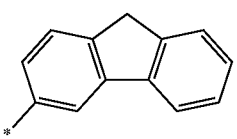
Formula (Ar¹-27)
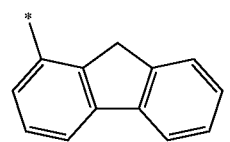
Formula (Ar¹-28)
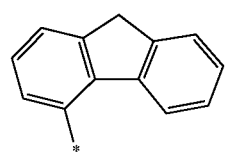

Formula (Ar¹-29)
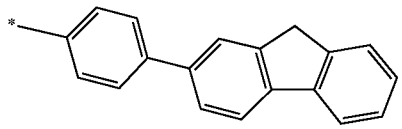
Formula (Ar¹-30)
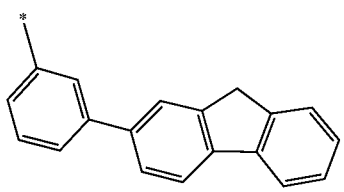
Formula (Ar¹-31)
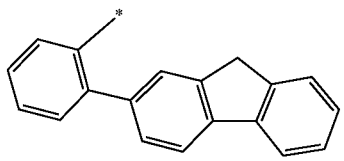
Formula (Ar¹-32)
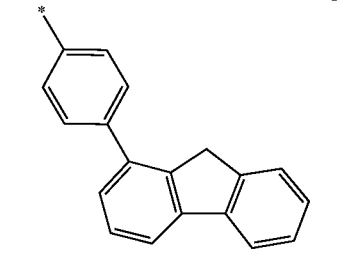
Formula (Ar¹-33)
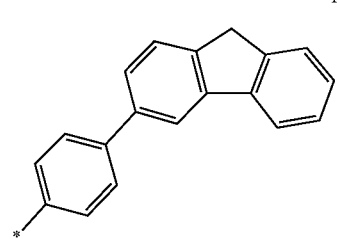
Formula (Ar¹-34)
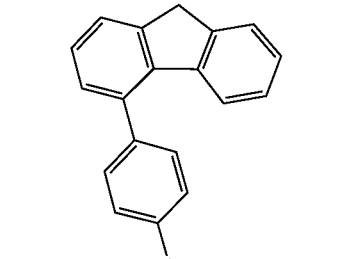
Formula (Ar¹-35)
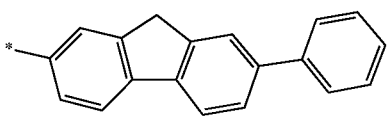
Formula (Ar¹-36)
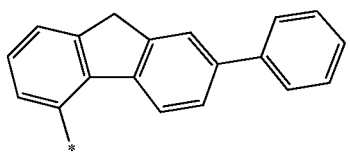
Formula (Ar¹-37)
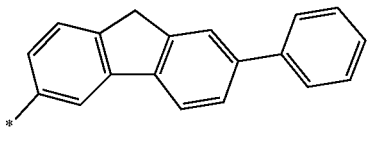
Formula (Ar¹-38)
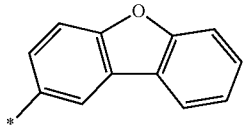
Formula (Ar¹-39)
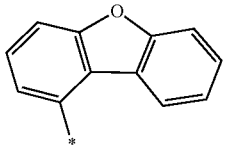
Formula (Ar¹-40)
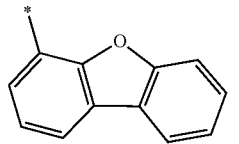
Formula (Ar¹-41)
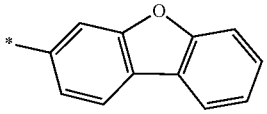
Formula (Ar¹-42)
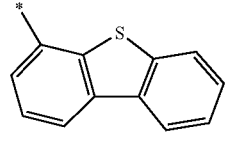
Formula (Ar¹-43)
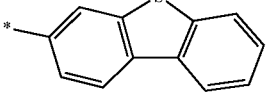
Formula (Ar¹-44)
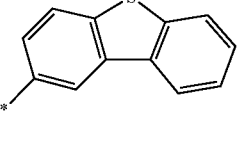
Formula (Ar¹-45)
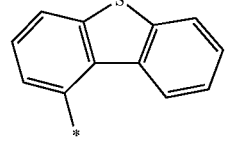

Formula (Ar¹-46)
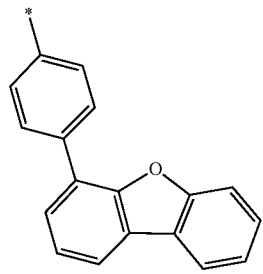
Formula (Ar¹-47)
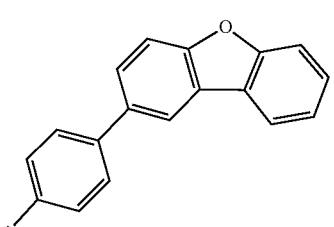
Formula (Ar¹-48)
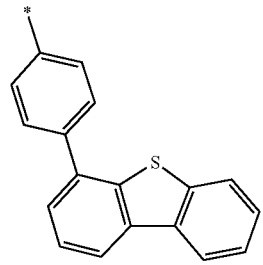
Formula (Ar¹-49)
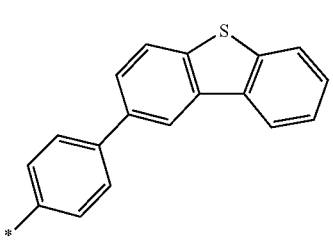
Formula (Ar¹-50)
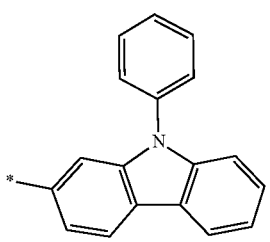
Formula (Ar¹-51)
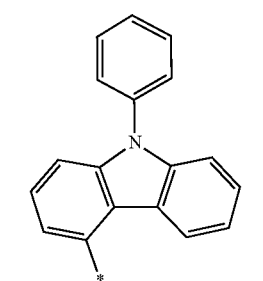
Formula (Ar¹-52)
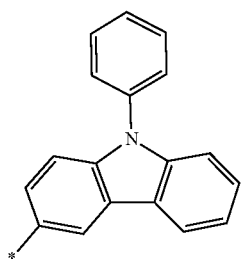
Formula (Ar¹-53)
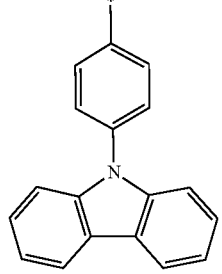
Formula (Ar¹-54)
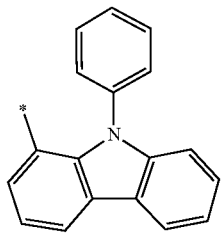
Formula (Ar¹-55)
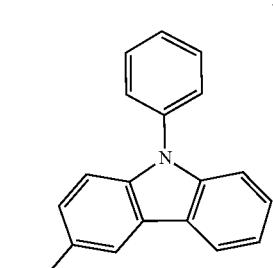
Formula (Ar¹-56)
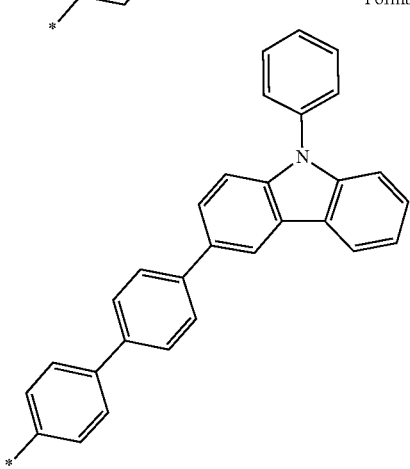

153

-continued

Formula (Ar¹-57)

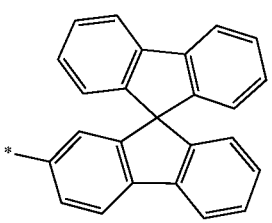

Formula (Ar¹-58)

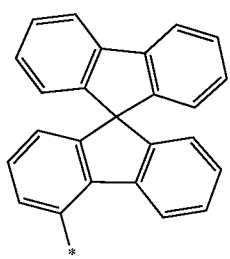

Formula (Ar¹-59)

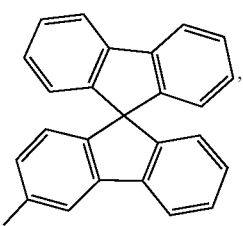

where the bond marked with * in each case represents the bond to the nitrogen atom, and where the formulae may bear R4 radicals at their unoccupied positions.

11. The compound as claimed in claim 1, wherein the compound contains, aside from the phenanthrene group depicted in formulae (I-1) or (I-2), no further fused aryl group having more than 10 aromatic ring atoms.

12. The compound as claimed in claim 1, wherein
R¹ is the same or different at each instance and is selected from H, D, F, CN, Si(R⁶)₃, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more R⁶ radicals, heteroaromatic ring systems which have 5 to 24 aromatic ring atoms and may be substituted by one or more R⁶ radicals, groups of the formula (A), as defined above, and groups of the formula (B), where the alkyl and alkoxy groups may each be substituted by one or more R⁶ radicals and where one or more CH₂ groups in the alkyl and alkoxy groups may be replaced by —C≡C—, —R⁶C═CR⁶—, Si(R⁶)₂, C═O, C═NR⁶, —NR⁶—, —O—, —S—, —C(═O)O— or —C(═O)NR⁶—;

and R², R³ are the same or different at each instance and are selected from H, D, F, CN, Si(R⁶)₃, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more R⁶ radicals, and heteroaromatic ring systems which have 5 to 24 aromatic ring atoms and may be substituted by one or more R⁶ radicals, where the alkyl and alkoxy groups may each be substituted by one or more R⁶ radicals and where one or more CH₂ groups

154 in the alkyl and alkoxy groups may be replaced by —C≡C—, —R⁶C═CR⁶—, Si(R⁶)₂, C═O, C═NR⁶, —NR⁶—, —O—, —S—, —C(═O)O— or —C(═O)NR⁶—.

13. The compound as claimed in claim 1, wherein Ar¹ is selected, identically or differently on each occurrence, from formulae (Ar¹-1) to (Ar¹-59)

Formula (Ar¹-1)

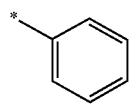

Formula (Ar¹-2)

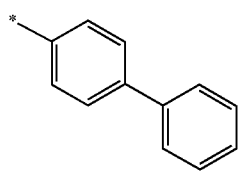

Formula (Ar¹-3)

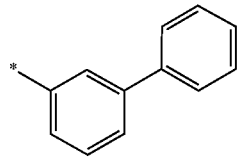

Formula (Ar¹-4)

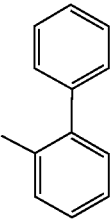

Formula (Ar¹-5)

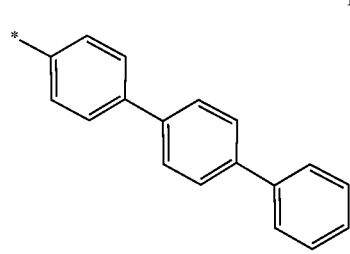

Formula (Ar¹-6)

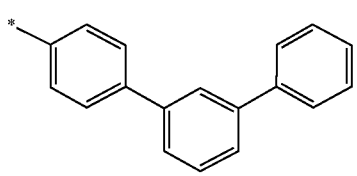

Formula (Ar¹-7)

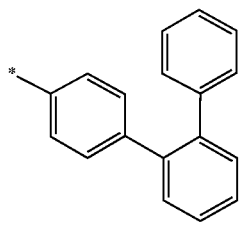

Formula (Ar¹-8)
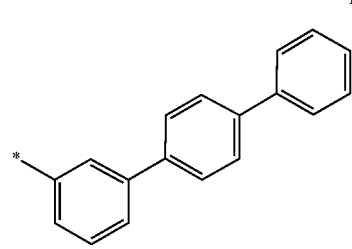
Formula (Ar¹-9)
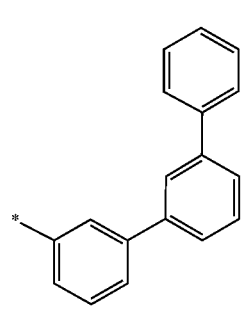
Formula (Ar¹-10)
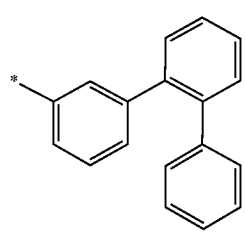
Formula (Ar¹-11)
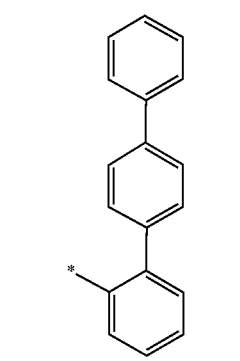
Formula (Ar¹-12)
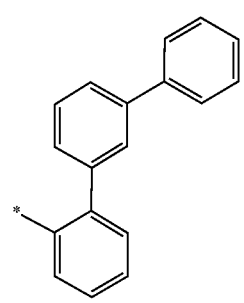
Formula (Ar¹-13)
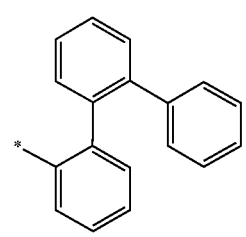
Formula (Ar¹-14)
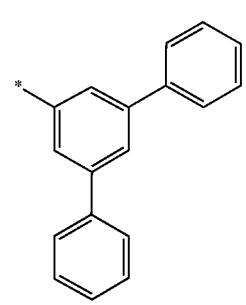
Formula (Ar¹-15)
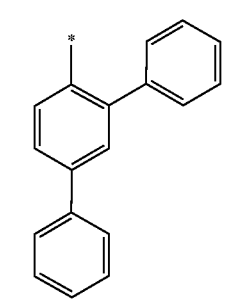
Formula (Ar¹-16)
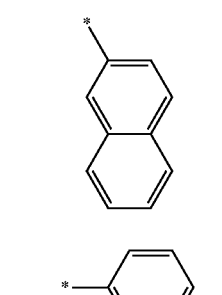
Formula (Ar¹-17)
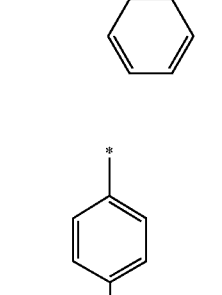
Formula (Ar¹-18)
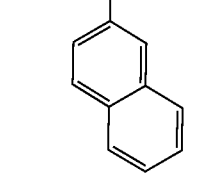

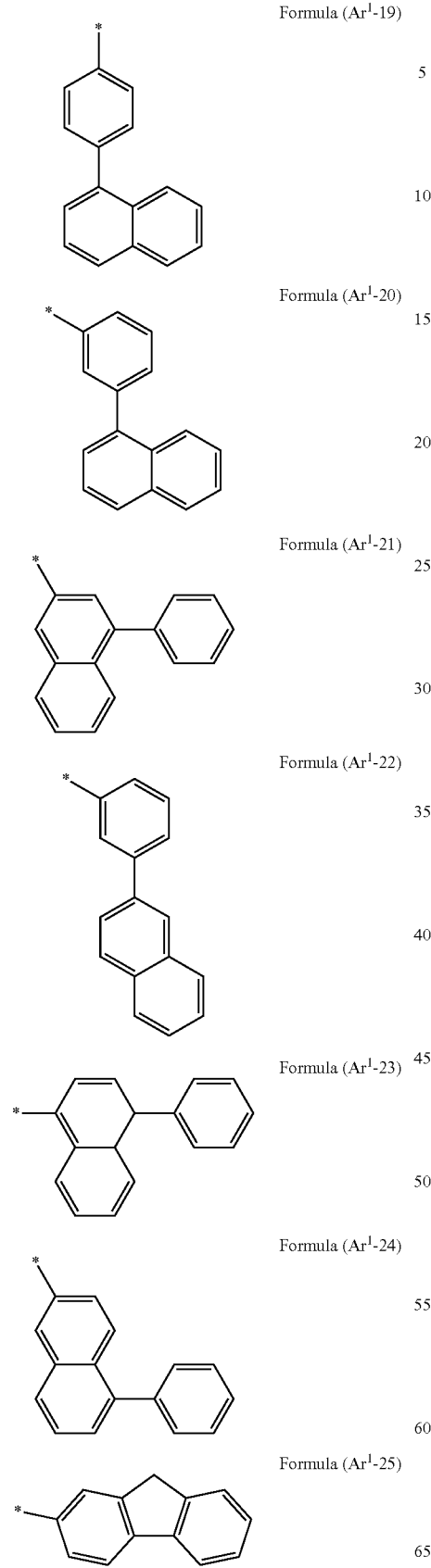
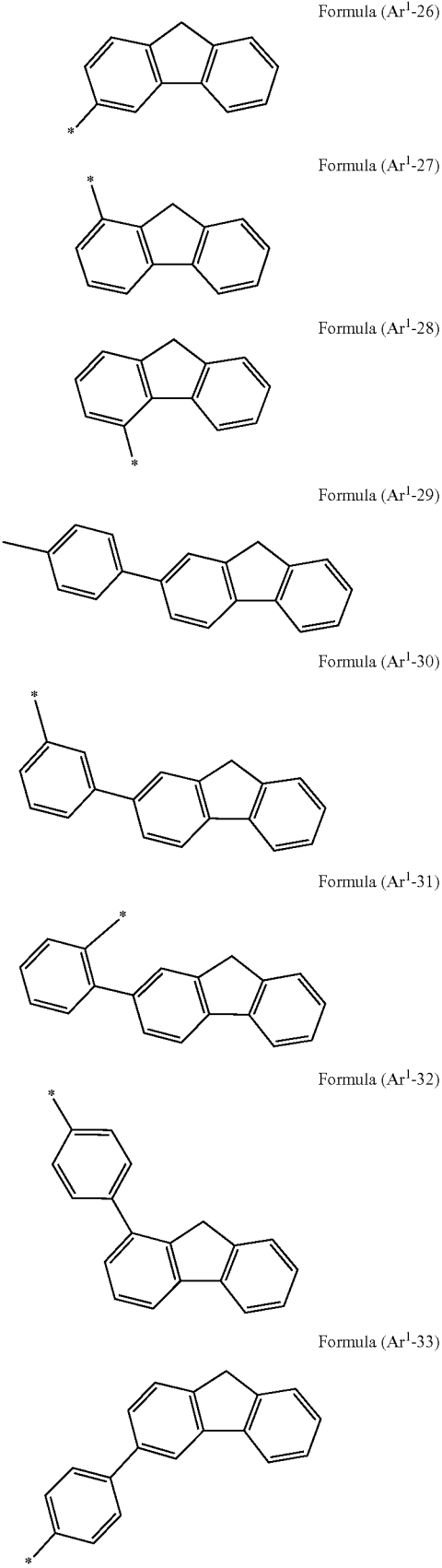

Formula (Ar¹-34)
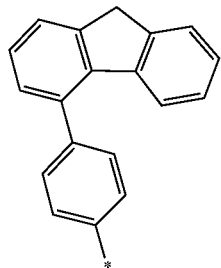
Formula (Ar¹-35)
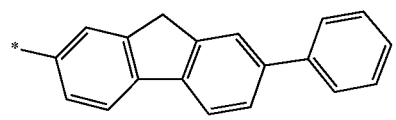
Formula (Ar¹-36)
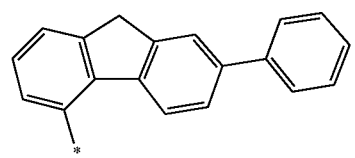
Formula (Ar¹-37)
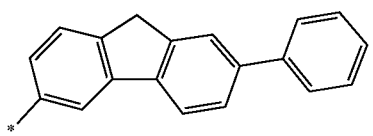
Formula (Ar¹-38)
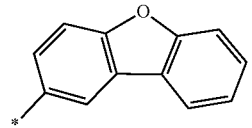
Formula (Ar¹-39)
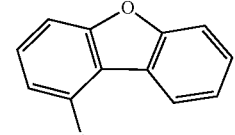
Formula (Ar¹-40)
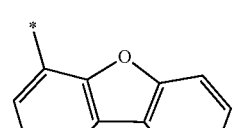
Formula (Ar¹-41)
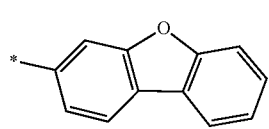
Formula (Ar¹-42)
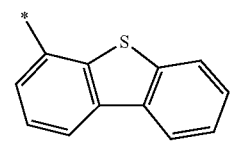
Formula (Ar¹-43)
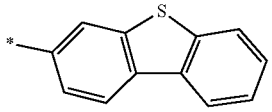
Formula (Ar¹-44)
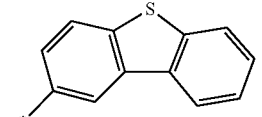
Formula (Ar¹-45)
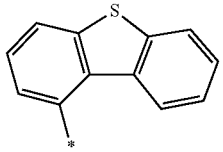
Formula (Ar¹-46)
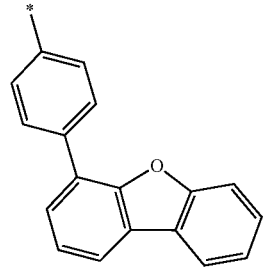
Formula (Ar¹-47)
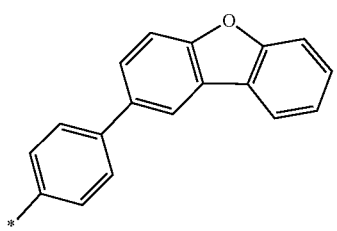
Formula (Ar¹-48)
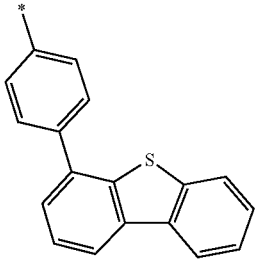
Formula (Ar¹-49)
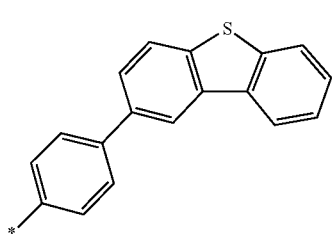

Formula (Ar¹-50)
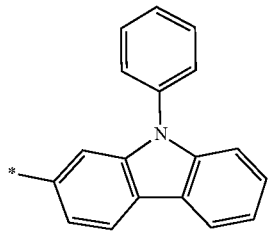
Formula (Ar¹-51)
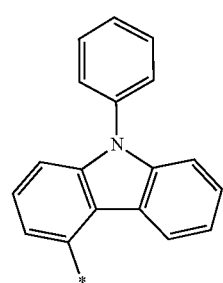
Formula (Ar¹-52)
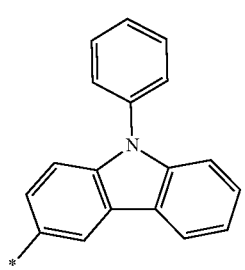
Formula (Ar¹-53)
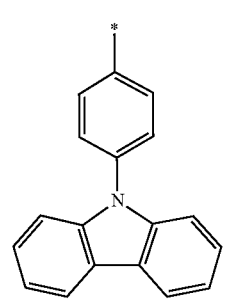
Formula (Ar¹-54)
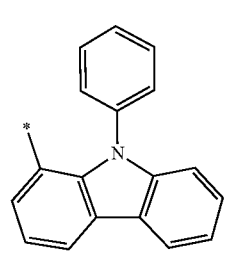
Formula (Ar¹-55)
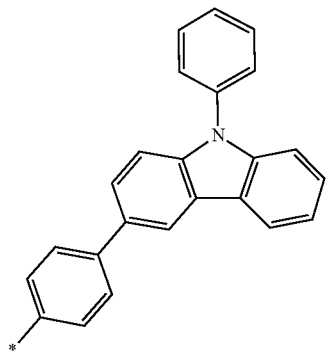
Formula (Ar¹-56)
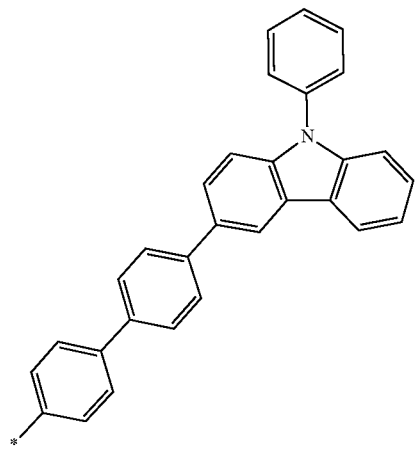
Formula (Ar¹-57)
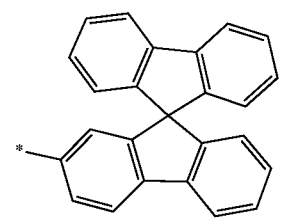
Formula (Ar¹-58)
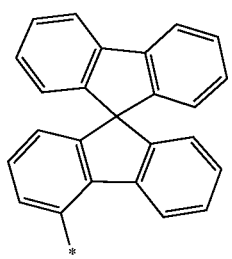
Formula (Ar¹-59)
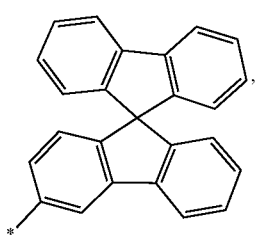

where the bond marked with * in each case represents the bond to the nitrogen atom, and where the formulae may bear R4 radicals at their unoccupied positions;

wherein the compound contains, aside from the phenanthrene group depicted in formulae (I-1) or (I-2), no further fused aryl group having more than 10 aromatic ring atoms;

wherein $R^1$ is the same or different at each instance and is selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^6$ radicals, heteroaromatic ring systems which have 5 to 24 aromatic ring atoms and may be substituted by one or more $R^6$ radicals, groups of the formula (A), as defined above, and groups of the formula (B), where the alkyl and alkoxy groups may each be substituted by one or more $R^6$ radicals and where one or more $CH_2$ groups in the alkyl and alkoxy groups may be replaced by —C≡C—, —$R^6$C=C$R^6$—, $Si(R^6)_2$, C=O, C=N$R^6$, —N$R^6$—, —O—, —S—, —C(=O)O— or —C(=O)N$R^6$—;

and $R^2$, $R^3$ are the same or different at each instance and are selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and may be substituted by one or more $R^6$ radicals, and heteroaromatic ring systems which have 5 to 24 aromatic ring atoms and may be substituted by one or more $R^6$ radicals, where the alkyl and alkoxy groups may each be substituted by one or more $R^6$ radicals and where one or more $CH_2$ groups in the alkyl and alkoxy groups may be replaced by —C≡C—, —$R^6$C=C$R^6$—, $Si(R^6)_2$, C=O, C=N$R^6$, —N$R^6$—, —O—, —S—, —C(=O)O— or —C(=O)N$R^6$—, wherein $R^4$ are the same or different at each instance and are selected from H, D, F, CN, $Si(R^6)_3$, straight-chain alkyl or alkoxy groups having 1 to 20 carbon atoms, branched or cyclic alkyl or alkoxy groups having 3 to 20 carbon atoms, where the alkyl and alkoxy groups mentioned may each be substituted by one or more $R^6$ radicals and where one or more $CH_2$ groups in the alkyl and alkoxy groups mentioned may be replaced by —C≡C—, —$R^6$C=C$R^6$—, $Si(R^6)_2$, C=O, C=N$R^6$, —N$R^6$—, —O—, —S—, —C(=O)O— or —C(=O)N$R^6$—; or benzene, naphthalene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, each of which may be substituted by one or more $R^6$ radicals;

and wherein $R^6$ is the same or different at each instance and is selected from H, D, F, CN, $Si(R^7)_3$, straight-chain alkyl or alkoxy groups having 1 to 20 carbon atoms, branched or cyclic alkyl or alkoxy groups having 3 to 20 carbon atoms, aromatic ring systems which have 6 to 24 aromatic ring atoms and is optionally substituted by one or more $R^7$ radicals, and heteroaromatic ring systems which have 5 to 24 aromatic ring atoms and is optionally substituted by one or more $R^7$ radicals, where the alkyl and alkoxy groups may each be substituted by one or more $R^7$ radicals and where one or more $CH_2$ groups in the alkyl and alkoxy groups is optionally replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—.

\* \* \* \* \*